US010238720B2

(12) United States Patent
Matthiessen et al.

(10) Patent No.: US 10,238,720 B2
(45) Date of Patent: *Mar. 26, 2019

(54) STABILIZED LIQUID AND LYOPHILIZED ADAMTS13 FORMULATIONS

(71) Applicants: BAXALTA INCORPORATED, Bannockburn, IL (US); BAXALTA GMBH, Zug (CH)

(72) Inventors: Peter Matthiessen, Vienna (AT); Peter L. Turecek, Klosterneuburg (AT); Hans-Peter Schwarz, Vienna (AT)

(73) Assignees: Baxalta Incorporated, Bannockburn, IL (US); Baxalta GmbH, Zug (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/908,213

(22) Filed: Feb. 28, 2018

(65) Prior Publication Data

US 2018/0207245 A1 Jul. 26, 2018

Related U.S. Application Data

(60) Continuation of application No. 15/400,526, filed on Jan. 6, 2017, now Pat. No. 9,937,244, which is a division of application No. 15/145,755, filed on May 3, 2016, now Pat. No. 9,572,778, which is a division of application No. 14/088,169, filed on Nov. 22, 2013, now Pat. No. 9,351,935, which is a continuation of application No. 12/887,424, filed on Sep. 21, 2010, now Pat. No. 8,623,352.

(60) Provisional application No. 61/244,353, filed on Sep. 21, 2009.

(51) Int. Cl.

| A61K 38/00 | (2006.01) |
| A61K 38/48 | (2006.01) |
| A61K 9/08 | (2006.01) |
| A61K 9/19 | (2006.01) |
| A61K 47/02 | (2006.01) |
| A61K 47/10 | (2017.01) |
| A61K 47/18 | (2017.01) |
| A61K 47/26 | (2006.01) |
| A61K 47/22 | (2006.01) |
| A61K 9/00 | (2006.01) |

(52) U.S. Cl.
CPC ............ *A61K 38/4886* (2013.01); *A61K 9/08* (2013.01); *A61K 9/19* (2013.01); *A61K 47/02* (2013.01); *A61K 47/10* (2013.01); *A61K 47/183* (2013.01); *A61K 47/22* (2013.01); *A61K 47/26* (2013.01); *C12Y 304/24087* (2013.01); *A61K 9/0019* (2013.01)

(58) Field of Classification Search
CPC .................. A61K 9/19; A61K 47/02
See application file for complete search history.

(56) References Cited

U.S. PATENT DOCUMENTS

| 6,926,894 | B2 | 8/2005 | Laemmle et al. |
| 7,037,858 | B2 | 5/2006 | Ginsburg et al. |
| 7,112,666 | B2 | 9/2006 | Soejima et al. |
| 7,361,748 | B2 | 4/2008 | Soejima et al. |
| 7,501,117 | B2 | 3/2009 | Laemmle et al. |
| 7,517,522 | B2 | 4/2009 | Ginsburg et al. |
| 7,780,831 | B2 | 8/2010 | Gabriel |
| 8,623,352 | B2 | 1/2014 | Matthiessen et al. |
| 2005/0266528 | A1 | 12/2005 | Laemmle et al. |
| 2006/0205661 | A1 | 9/2006 | Besman et al. |
| 2006/0233784 | A1 | 10/2006 | Ginsburg et al. |
| 2007/0015703 | A1 | 1/2007 | Wagner et al. |
| 2007/0280924 | A1 | 12/2007 | Daniels et al. |
| 2008/0176312 | A1 | 7/2008 | Laemmle et al. |
| 2009/0017467 | A1 | 1/2009 | Laemmle et al. |

FOREIGN PATENT DOCUMENTS

| JP | 2001-227610 A | 8/2001 |
| JP | 2007-174978 A | 7/2007 |
| WO | WO 02/42441 A2 | 6/2002 |
| WO | WO 02/42441 A3 | 6/2002 |
| WO | WO 02/088366 A1 | 11/2002 |
| WO | WO 03/018492 A2 | 2/2003 |
| WO | WO 03/018492 A3 | 2/2003 |

OTHER PUBLICATIONS

Anderson, P.J. et al., "Characterization of Optimal Reaction Conditions for ADAMTS13 at Physiological PH," Blood, Nov. 16, 2003, p. 783a, Abstract No. 2895. vol. 102, No. 11.
Anderson, P.J. et al., "Zinc and Calcium Ions Cooperatively Modulate ADAMTS13 Activity," The Journal of Biological Chemistry, Jan. 13, 2006, pp. 850-857, vol. 281, No. 2.
Chauhan, A.K. et al., "ADAMTS13: a new link between thrombosis and inflammation," J. Exp. Med., Aug. 11, 2008, pp. 2065-2074, vol. 205, No. 9.
Dent, J.A. et al., "Heterogeneity of Plasma von Willebrand Factor Multimers Resulting from Proteolysis of the Constituent Subunit," J. Clin. Invest., Sep. 1991, pp. 774-782, vol. 88.
Dent, J.A. et al., "Identification of a cleavage site directing the immunochemical detection of molecular abnormalities in type IIA von Willebrand factor," Proc. Natl. Acad. Sci. USA, Aug. 1990, pp. 6306-6310, vol. 87.
Di Stasio. E. et al., "Mechanistic Studies on ADAMTS13 Catalysis," Biophysical Journal, Sep. 2008, pp. 2450-2461, vol. 95, No. 5.
Donadelli, R. et al., "Size regulation of von Willebrand factor-mediated platelet thrombi by ADAMTS13 in flowing blood," Blood, Mar. 1, 2006, pp. 1943-1950, vol. 107, No. 5.

(Continued)

Primary Examiner — Ruth A Davis
(74) Attorney, Agent, or Firm — Troutman Sanders LLP

(57) ABSTRACT

The present invention relates to formulations of ADAMTS13 with enhanced or desirable properties. As such, the invention provides liquid and lyophilized formulations of ADAMTS13 that are suitable for pharmaceutical administration. Among other aspects, the present invention also provides methods of treating various diseases and conditions related to VWF and/or ADAMTS13 dysfunction in a subject. Also provided herein are kits comprising ADAMTS13 formulations useful for the treatment of various diseases and conditions.

30 Claims, 58 Drawing Sheets

(56) References Cited

OTHER PUBLICATIONS

Fontana, S. et al., "Plasma Therapy in Thrombotic Thrombocytopenic Purpura: Review of the Literature and the Bern Experience in Subgroups of Patients With Severe Acquired ADAMTS-13 Deficiency," *Seminars in Hematology*, Jan. 2004, pp. 48-59, vol. 41, No. 1.

Fujikawa, K. et al., "Purification of human von Willebrand factor-cleaving protease and its identification as a new member of the metalloproteinase family," *Blood*, Sep. 15, 2001, pp. 1662-1666, vol. 98, No. 6.

Furlan, M. et al., "Deficiency of von Willebrand factor-cleaving protease in familial and acquired thrombic thrombocytopenic purpura," *Bailliere's Clinical Haematology*, Jun. 1998, pp. 509-514, vol. 11, No. 2.

Furlan, M. et al., "Deficient Activity of von Willebrand Factor—Cleaving Protease in Chronic Relapsing Thrombotic Thrombocytopenic Purpura," *Blood*, May 1, 1997, pp. 3097-3103, vol. 89, No. 9.

Furlan, M. et al., "Partial Purification and Characterization of a Protease From Human Plasma Cleaving von Willebrand Factor to Fragments Produced by in Vivo Proteolysis," *Blood*, May 15, 1998, pp. 4223-4234, vol. 87, No. 10.

Furlan. M. et al., "Triplet structure of von Willebrand factor reflects proteolytic degradation of high molecular weight multimers," *Proc. Natl. Acad. Sci. USA*, Aug. 1993, pp. 7503-7507, vol. 90.

Gao, W. et al., "The C-Terminal α-Helix von Willebrand Factor Domain A2 Interacts with ADAMTS13 C-Terminal Domains to Regulate Substrate Cleavage," *Blood*, Nov. 16, 2005, p. 123a. Abstract No. 410, vol. 106, No. 11.

Gardner, M.D. et al., "A functional calcium-binding site in the metalloprotease domain of ADAMTS13," *Blood*, Jan. 29, 2009, vol. 113, No. 5, pp. 1149-1158.

Gerritsen, H.E. et al., "Partial amino acid sequence of purified von Willebrand factor-cleaving protease," *Blood*, Sep. 15, 2001, pp. 1654-1661, vol. 98, No. 6.

International Search Report dated Oct. 12, 2011, for International Patent Application No. PCT/US2010/049723, 4 pages.

Jones, G.C., "ADAMTS Proteinases: Potential Therapeutic Targets?" *Current Pharmaceutical Biotechnology*, 2006, pp. 25-31, vol. 7, No. 1.

Kokame, K. et al., "FRETS-VWF73, a first fluorogenic substrate for ADAMTS13 assay," *British Journal of Haematology*, 2005, pp. 93-100, vol. 129, Blackwell Publishing Ltd.

Larkin, D. et al., "Server *Plasmodium faiciparum* Malaria is Associated with Circulating Ultra-Large von Willebrand Multimers and ADAMTS13 Inhibition," *Plos Pathogens*, Mar. 2009, pp. 1-8, vol. 5, No. 3.

Levy, G.G. et al., "Mutations in a member of the ADAMTS gene family cause thrombotic thrombocytopenic purpura," *Nature*, Oct. 4, 2001, pp. 488-494, vol. 413.

Moake, J.L, "Von Willebrand Factor, ADAMTS-13, and Thrombotic Thrombocytopenic Purpura," *Seminars in Hematology*, Jan. 2004, pp. 4-14, vol. 41, No. 1.

Moake, J.L., "Thrombotic Thrombocytopenic Purpura and the Hemolytic Uremic Syndrome," *Arch Pathol Lab Med*, Nov. 2002, pp. 1430-1433, vol. 126.

Nicholson, A.C. et al., "Functional evolution of ADAMTS genes: Evidence from analyses of phylogeny and gene organization," *BMC Evolutionary Biology*, Feb. 4, 2005, 13 pages, vol. 5, No. 11.

Rayes, J. et al., "Effect of von Willebrand disease type 2B and type 2M mutations on the susceptibility of von Willebrand factor to ADAMTS-13," *Journal of Thrombosis and Haemostasis*, 2007, pp. 321-328, vol. 5.

Scheiflinger, F. et al., "Nonneutralizing IgM and IgG antibodies to van Willebrand factor-cleaving protease (ADAMTS-13) in a patient with thrombotic thrombocytopenic purpura," *Blood*, Nov. 1, 2003, pp. 3241-3243, vol. 102, No. 9.

Soejima, K. et al., "A Novel Human Metalloprotease Synthesized in the Liver and Secreted into the Blood: Possibly, the von Willebrand Factor-Cleaving Protease?" *J. Biochem.*, 2001, pp. 475-480, vol. 130, No. 4.

Tsai, H-M. et al., "Antibodies to von Willebrand Factor-Cleaving Protease in Acute Thrombotic Thrombocytopenic Purpura," *The New England Journal of Medicine*, Nov. 26, 1998, pp. 1585-1594, vol. 339, No. 22.

Tsai, H-M. et al., "Endothelial Cell-Derived High Molecular Weight von Willebrand Factor is Converted into the Plasma Multimer Pattern by Granulocyte Proteases," *Biochemical and Biophysical Research Communications*, Feb. 15, 1989, pp. 980-985, vol. 158, No. 3.

Tsai, H-M. et al., "Proteolytic Cleavage of Recombinant Type 2A von Willebrand Factor Mutants R834W and R834Q: Inhibition by Doxycycline and by Monoclonal Antibody VP-1," *Blood*, Mar. 15, 1997, pp. 1954-1962, vol. 89, No. 6.

Tsai, H-M., "Deficiency of ADAMTS-13 in thrombotic and thrombocytopenic purpura," *Journal of Thrombosis and Haemostasis*, 2003, pp. 2038-2040, vol. 1.

Tsai, H-M., "Physiologic Cleavage of von Willebrand Factor by a Plasma Protease is Dependent of its Conformation and Requires Calcium Ion," *Blood*, May 15, 1996, pp. 4235-4244, vol. 87, No. 10.

Tsai, H-M., "Von Willebrand factor, ADAMTS13, and thrombotic thrombocytopenic purpura," *J Mol Med*, 2002, pp. 639-647, vol. 80.

U.S. Appl. No. 09/721,254, filed Nov. 22, 2000, for Bernhard Lammle.

U.S. Appl. No. 60/312,834, filed Aug. 16, 2001, for David Ginsburg et al.

U.S. Appl. No. 60/729,323, filed Oct. 21, 2005, for Denisa Wagner.

Yagi, H. et al., "Recombinant ADAMTS13 Rapidly and Preferentially Cleaves Unusually-Large von Willebrand Factor Multimers in the Plasmas with Upshaw Shulman Syndrome under High Shear-Stress," *Blood*, Nov. 2002, p. 685a, Abstract No. 2699, vol. 100, No. 11.

Zheng, X. et al., "Structure of von Willebrand Factor-cleaving Protease (ADAMTS13), a Metalloprotease involved in Thrombotic Thrombocytopenic Purpura," *The Journal of Biological Chemistry*, Nov. 2, 2001, pp. 41059-41063, vol. 276, No. 44.

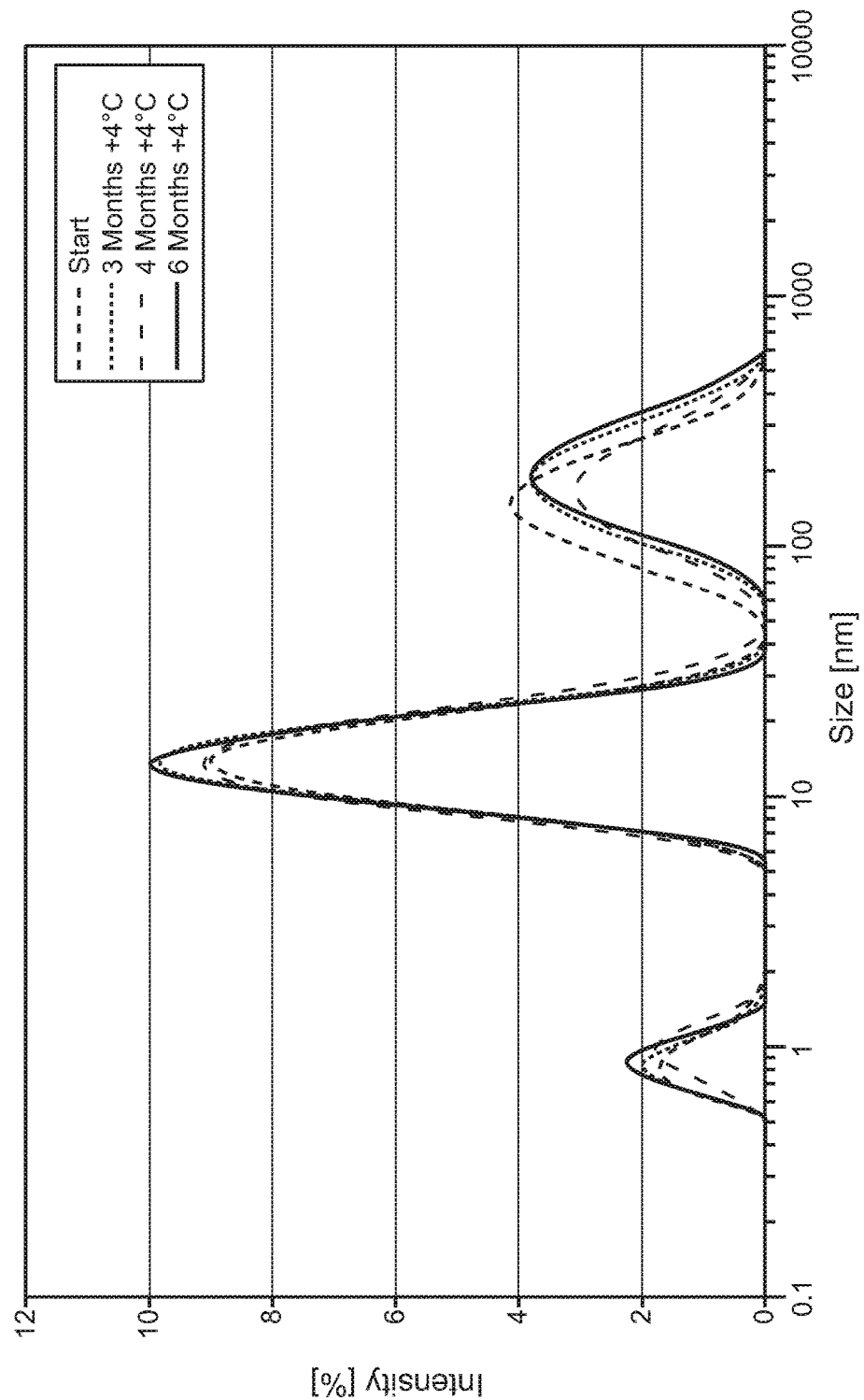

STABILIZED LIQUID AND LYOPHILIZED ADAMTS13 FORMULATIONS

CROSS-REFERENCES TO RELATED APPLICATIONS

The present application is a continuation of U.S. patent application Ser. No. 15/400,526, filed Jan. 6, 2017, which is a divisional of U.S. patent application Ser. No. 15/145,755, filed May 3, 2016, now U.S. Pat. No. 9,572,778, issued Feb. 21, 2017, which is a divisional of U.S. patent application Ser. No. 14/088,169, filed Nov. 22, 2013, now U.S. Pat. No. 9,351,935, issued May 31, 2016, which is a continuation of U.S. patent application Ser. No. 12/887,424 filed Sep. 21, 2010, now U.S. Pat. No. 8,623,352, issued Jan. 7, 2014, which claims the benefit of U.S. Provisional Application No. 61/244,353 filed Sep. 21, 2009, which are expressly incorporated herein by reference in their entireties for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The ADAMTS (a disintegrin and metalloproteinase with thrombospondin type I motifs) proteins are a family of metalloproteinases containing number of conserved domains, including a zinc-dependant catalytic domain, a cystein-rich domain, a disintegrin-like domain, and at least one, and in most cases multiple, thrombospondin type I repeats (for review, see Nicholson et al., BMC Evol Biol. 2005 Feb. 4; 5(1):11). These proteins, which are evolutionarily related to the ADAM and MMP families of metalloproteinases (Jones G C, Curr Pharm Biotechnol. 2006 February; 7(1):25-31), are secreted enzymes that have been linked to a number of diseases and conditions including thrombotic thrombocytopenic purpura (TTP) (Moake J L, Semin Hematol. 2004 January; 41(1):4-14), connective tissue disorders, cancers, inflammation (Nicholson et al.), and severe *plasmodium falciparum* malaria (Larkin et al., PLoS Pathog. 2009 March; 5(3):e1000349). Because of these associations, the ADAMTS enzymes have been recognized as potential therapeutic targets for a number of pathologies (Jones G C, Curr Pharm Biotechnol. 2006 February; 7(1): 25-31).

One ADAMTS family member, ADAMTS13, cleaves von Willebrand factor (vWF) between residues Tyr 1605 and Met 1606. Loss of ADAMTS13 activity has been linked to a number of conditions, such as TTP (Moake J L, Semin Hematol. 2004 January; 41(1):4-14), acute and chronic inflammation (Chauhan et al., J Exp Med. 2008 Sep. 1; 205(9):2065-74), and most recently, severe *plasmodium falciparum* malaria (Larkin et al., PLoS Pathog. 2009 March; 5(3): e1000349).

Thrombotic thrombocytopenic purpura (TTP) is a disorder characterized by thrombotic microangiopathy, thrombocytopenia and microvascular thrombosis that can cause various degrees of tissue ischemia and infarction. Clinically, TTP patients are diagnosed by symptoms such as thrombocytopenia, schistocytes (fragments of erythrocytes) and elevated levels of lactate dehydrogenase (Moake J L. Thrombotic microangiopathies. N Engl J Med. 2002; 347: 589-600; Moake J L. von Willebrand factor, ADAMTS-13, and thrombotic thrombocytopenic purpura. Semin Hematol. 2004; 41:4-14; Sadler J E, Moake J L, Miyata T, George J N. Recent advances in thrombotic thrombocytopenic purpura. Hematology (Am Soc Hematol Educ Program). 2004: 407-423; Sadler J E. New concepts in von Willebrand disease. Annu Rev Med. 2005; 56:173-191).

In 1982, Moake et al. found unusually large von Willebrand factor (UL-vWF) multimers in the plasma of the patients with chronic relapsing TTP (Moake J L, Rudy C K, Troll J H, Weinstein M J, Colannino N M, Azocar J, Seder R H, Hong S L, Deykin D. Unusually large plasma factor VIII:von Willebrand factor multimers in chronic relapsing thrombotic thrombocytopenic purpura. N Engl J Med. 1982; 307:1432-1435). The link between UL-vWF and TTP gained support with independent findings by Furlan et al. and Tsai and Lian that most patients suffering from TTP are deficient in a plasma metalloprotease, now known to be ADAMTS13, that cleaves vWF (Furlan M, Robles R, Solenthaler M, Wassmer M, Sandoz P, Laemmle B. Deficient activity of von Willebrand factor-cleaving protease in chronic relapsing thrombotic thrombocytopenic purpura. Blood. 1997; 89:3097-3103; Tsai H M, Sussman, I I, Ginsburg D, Lankhof H, Sixma J J, Nagel R L. Proteolytic cleavage of recombinant type 2A von Willebrand factor mutants R834W and R834Q: inhibition by doxycycline and by monoclonal antibody VP-1. Blood. 1997; 89:1954-1962; Tsai H M, Lian E C. Antibodies to von Willebrand factor-cleaving protease in acute thrombotic thrombocytopenic purpura. N Engl J Med. 1998; 339:1585-1594).

The ADAMTS13 protease is a 190 kDa glycosylated protein produced predominantly by the liver (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. Nature. 2001; 413: 488-494; Fujikawa K, Suzuki H, McMullen B, Chung D. Purification of human von Willebrand factor-cleaving protease and its identification as a new member of the metalloproteinase family. Blood. 2001; 98:1662-1666; Zheng X, Chung D, Takayama T K, Maj ems E M, Sadler J E, Fujikawa K. Structure of von Willebrand factor-cleaving protease (ADAMTS13), a metalloprotease involved in thrombotic thrombocytopenic purpura. J Biol Chem. 2001; 276:41059-41063; Soejima K, Mimura N, Hirashima M, Maeda H, Hamamoto T, Nakagaki T, Nozaki C. A novel human metalloprotease synthesized in the liver and secreted into the blood: possibly, the von Willebrand factor-cleaving protease; J Biochem (Tokyo). 2001; 130:475-480; Gerritsen H E, Robles R, Lammle B, Furlan M. Partial amino acid sequence of purified von Willebrand factor-cleaving protease. Blood. 2001; 98:1654-1661).

Mutations in the ADAMTS13 gene have been shown to cause TTP (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. Nature. 2001; 413:488-494). Idiopathic TTP, often caused by autoantibodies inhibiting ADAMTS-13 activity, is a more common disorder that occurs in adults and older children and can recur at regular intervals in 11-36% of patients (Tsai H M, Lian E C. Antibodies to von Willebrand factor-cleaving protease in acute thrombotic thrombocytopenic purpura. N Engl J Med. 1998; 339:1585-1594; Furlan M, Lammle B. Deficiency of von Willebrand factor-cleaving protease in familial and acquired thrombotic thrombocytopenic purpura. Baillieres Clin Haematol. 1998; 11:509-514).

Non neutralizing autoantibodies could also inhibit ADAMTS activity by inducing clearance from circulation (Scheiflinger F, Knobl P, Trattner B, Plaimauer B, Mohr G, Dockal M, Dorner F, Rieger M. Nonneutralizing IgM and IgG antibodies to von Willebrand factor-cleaving protease (ADAMTS-13) in a patient with thrombotic thrombocytopenic purpura. Blood. 2003; 102:3241-3243). Plasma ADAMTS13 activity in healthy adults ranges from 50% to 178% (Moake J L. Thrombotic thrombocytopenic purpura and the hemolytic uremic syndrome. Arch Pathol Lab Med. 2002; 126:1430-1433). In most patients with familial or acquired TTP, plasma ADAMTS13 activity is absent or less than 5% of the normal. Without treatment the mortality rate exceeds 90%, but plasma therapy has reduced mortality to about 20% (Moake J L. Thrombotic thrombocytopenic purpura and the hemolytic uremic syndrome. Arch Pathol Lab Med. 2002; 126:1430-1433).

vWF synthesized in megakaryocytes and endothelial cells is stored in platelet-granules and Weibel-Palade bodies, respectively, as ultra large vWF (UL-vWF) (Moake J L, Rudy C K, Troll J H, Weinstein M J, Colannino N M, Azocar J, Seder R H, Hong S L, Deykin D. Unusually large plasma factor VIII:von Willebrand factor multimers in chronic relapsing thrombotic thrombocytopenic purpura. N Engl J Med. 1982; 307:1432-1435; Wagner D D, Olmsted J B, Marder V J. Immunolocalization of von Willebrand protein in Weibel-Palade bodies of human endothelial cells. J Cell Biol. 1982; 95:355-360; Wagner D D, Bonfanti R. von Willebrand factor and the endothelium. Mayo Clin Proc. 1991; 66:621-627; Sporn L A, Marder V J, Wagner D D. von Willebrand factor released from Weibel-Palade bodies binds more avidly to extracellular matrix than that secreted constitutively. Blood. 1987; 69:1531-1534; Tsai H M, Nagel R L, Hatcher V B, Sussman, I I. Endothelial cell-derived high molecular weight von Willebrand factor is converted into the plasma multimer pattern by granulocyte proteases. Biochem Biophys Res Commun. 1989; 158:980-985; Tsai H M, Nagel R L, Hatcher V B, Sussman, I I. Multimeric composition of endothelial cell-derived von Willebrand factor. Blood. 1989; 73:2074-2076). Once secreted from endothelial cells, these UL-vWF multimers are cleaved by ADAMTS13 in circulation into a series of smaller multimers at specific cleavage sites within the vWF molecule (Tsai H M, Nagel R L, Hatcher V B, Sussman, I I. Endothelial cell-derived high molecular weight von Willebrand factor is converted into the plasma multimer pattern by granulocyte proteases. Biochem Biophys Res Commun. 1989; 158:980-985; Dent J A, Galbusera M, Ruggeri Z M. Heterogeneity of plasma von Willebrand factor multimers resulting from proteolysis of the constituent subunit. J Clin Invest. 1991; 88:774-782; Furlan M, Robles R, Affolter D, Meyer D, Baillod P, Lammle B. Triplet structure of von Willebrand factor reflects proteolytic degradation of high molecular weight multimers. Proc Natl Acad Sci USA. 1993; 90:7503-7507).

ADAMTS13 cleaves at the Tyr842-Met843 bond in the central A2 domain of the mature vWF subunit and requires zinc or calcium for activity (Dent J A, Berkowitz S D, Ware J, Kasper C K, Ruggeri Z M. Identification of a cleavage site directing the immunochemical detection of molecular abnormalities in type IIA von Willebrand factor. Proc Natl Acad Sci USA. 1990; 87:6306-6310). vWF exists in "ball-of-yarn" and filamentous form as seen by electron microscopy (Slayter H, Loscalzo J, Bockenstedt P, Handin R I. Native conformation of human von Willebrand protein. Analysis by electron microscopy and quasi-elastic light scattering. J Biol. Chem. 1985; 260:8559-8563). Furthermore, atomic force microscopy confirms that vWF exits in a globular conformation under static conditions and an unfolded filamentous state after exposure to shear stress (Siedlecki C A, Lestini B J, Kottke-Marchant K K, Eppell S J, Wilson D L, Marchant R E. Shear-dependent changes in the three-dimensional structure of human von Willebrand factor. Blood. 1996; 88:2939-2950). This could occur also in vivo when one end of the vWF filament is anchored to a surface.

Thrombi of TTP patients consist of little fibrin and mainly of vWF and platelets, suggesting vWF-mediated platelet aggregation as a cause of thrombosis (Asada Y, Sumiyoshi A, Hayashi T, Suzumiya J, Kaketani K. Immunohistochemistry of vascular lesion in thrombotic thrombocytopenic purpura, with special reference to factor VIII related antigen. Thromb Res. 1985; 38:469-479). Patients with relapsing TTP have ultra-large multimers in the plasma. The UL-vWF multimers accumulate over time because the persistence of the inhibitor (Anti-ADAMTS13 Ab) decreases ADAMTS13 activity. The UL-vWF multimers are hyperactive and unfold as a result of shear stress causing platelet aggregation, resulting in intravascular thrombosis (Tsai H M. Von Willebrand factor, ADAMTS13, and thrombotic thrombocytopenic purpura. J Mol Med. 2002; 80:639-647; Tsai H M. Deficiency of ADAMTS-13 in thrombotic and thrombocytopenic purpura. J Thromb Haemost. 2003; 1:2038-2040; discussion 2040-2035).

It is believed that the presence of hyper-reactive UL-vWF multimers in the plasma due to ADAMTS13 deficiency could be associated with an increased risk of arterial thrombosis linked to coronary heart disease.

Accordingly, there is a need in the art for pharmaceutical formulations of ADAMTS13 proteins suitable for the treatment of various diseases and conditions associated with ADAMTS13 and VWF dysfunction. The present invention provides, among other aspects, ADAMTS13 formulations suitable for pharmaceutical administration, as well as methods of treating subjects with diseases or conditions associated with ADAMTS13 and VWF dysfunction.

BRIEF SUMMARY OF THE INVENTION

In one aspect, the present invention provides formulations of ADAMTS13 (A13) suitable for pharmaceutical administration. Advantageously, in some embodiments, the invention provides A13 formulations that may be stored for extended periods of time without loosing activity or becoming overly aggregated. In certain embodiments, the formulations of the invention may be stored for at least 6 months at temperatures up to at least about 37° C.

In one aspect, the present invention provides a stabilized formulation of ADAMTS13 (A13) comprising (a) 0.05 mg/ml to 10.0 mg/ml ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0.

In a related aspect, the present invention provides a stabilized lyophilized formulation of ADAMTS13 (A13), wherein the formulation is lyophilized from a liquid formulation comprising (a) 0.05 mg/ml to 10.0 mg/ml ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0.

In one aspect of the invention, recombinant ADAMTS13 (rA13) formulations suitable for pharmaceutical administration are provided. In some embodiments, the formulations provided herein have high specific activities and are stable upon storage for extended periods of time.

In another aspect of the invention, formulations are provided that have reduced dimerization or aggregation of A13 and rA13. In certain embodiments, the formulations provided herein retard the formation of A13 and rA13 dimers and aggregation when stored for extended periods of time. In some embodiments, these formulations are suitable for pharmaceutical administration.

In one aspect, the present invention relates to a method of treating or preventing a disorder associated with the formation and/or presence of one or more thrombus and to a method of disintegrating one or more thrombus in a patient in need thereof. Examples of disorders associated with the formation and/or the presence of one or more thrombus are hereditary thrombotic thrombocytopenic purpura (TTP), acquired TTP, arterial thrombosis, acute myocardial infarction (AMI), stroke, sepsis, and disseminated intravascular coagulation (DIC). In one embodiment, the methods of treating or preventing include the administration of an A13 or rA13 formulation provided herein.

In another aspect, the present invention provides methods of treating or preventing an infarction in a patient in need thereof. In certain embodiments, methods are provided for treating or preventing a disease or condition associated with an infarction, including without limitation, myocardial infarction (heart attack), pulmonary embolism, cerebrovascular events such as stroke, peripheral artery occlusive disease (such as gangrene), antiphospholipid syndrome, sepsis, giant-cell arteritis (GCA), hernia, and volvulus. In one embodiment, the methods of treating or preventing include the administration of an A13 or rA13 formulation provided herein.

In one aspect, the present invention provides methods of formulating A13 or rA13 with high stability and/or high specific activities. In certain embodiments, the methods are useful for formulating solutions and lyophilisates that can be stored for extended periods of time at temperatures up to at least about 37° C. without loosing high specific activities desirable for pharmaceutical administration.

In another aspect, kits for the pharmaceutical administration of A13 or rA13 are provided herein. The kits of the invention, in certain embodiments, may comprise liquid or lyophilized formulations that may be stored for extended periods of time.

sodium citrate. Solutions were stored at 4° C. or 37° C. for 6 months. Lyophilized formulations were reconstituted with sterile water and the purity of all samples were determined by reverse phase-HPLC analysis.

Figure 11:
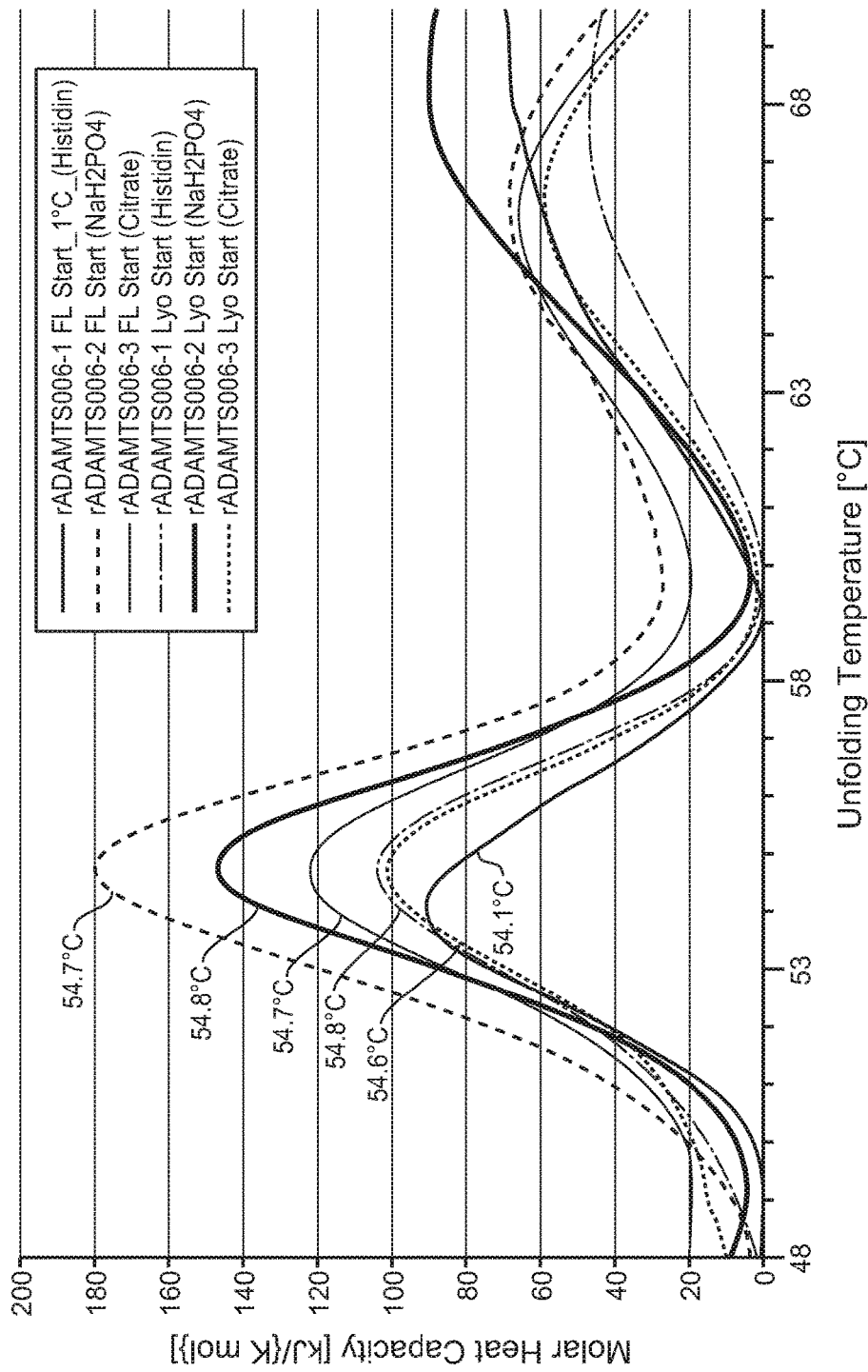

FIG. 11. Recombinant ADAMTS13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3) sodium citrate. Samples of the solution formulations were also lyophilized and reconstituted with sterile water. Solution and reconstituted lyophilized formulations were characterized by differential scanning calorimetry analysis.

Figure 12:
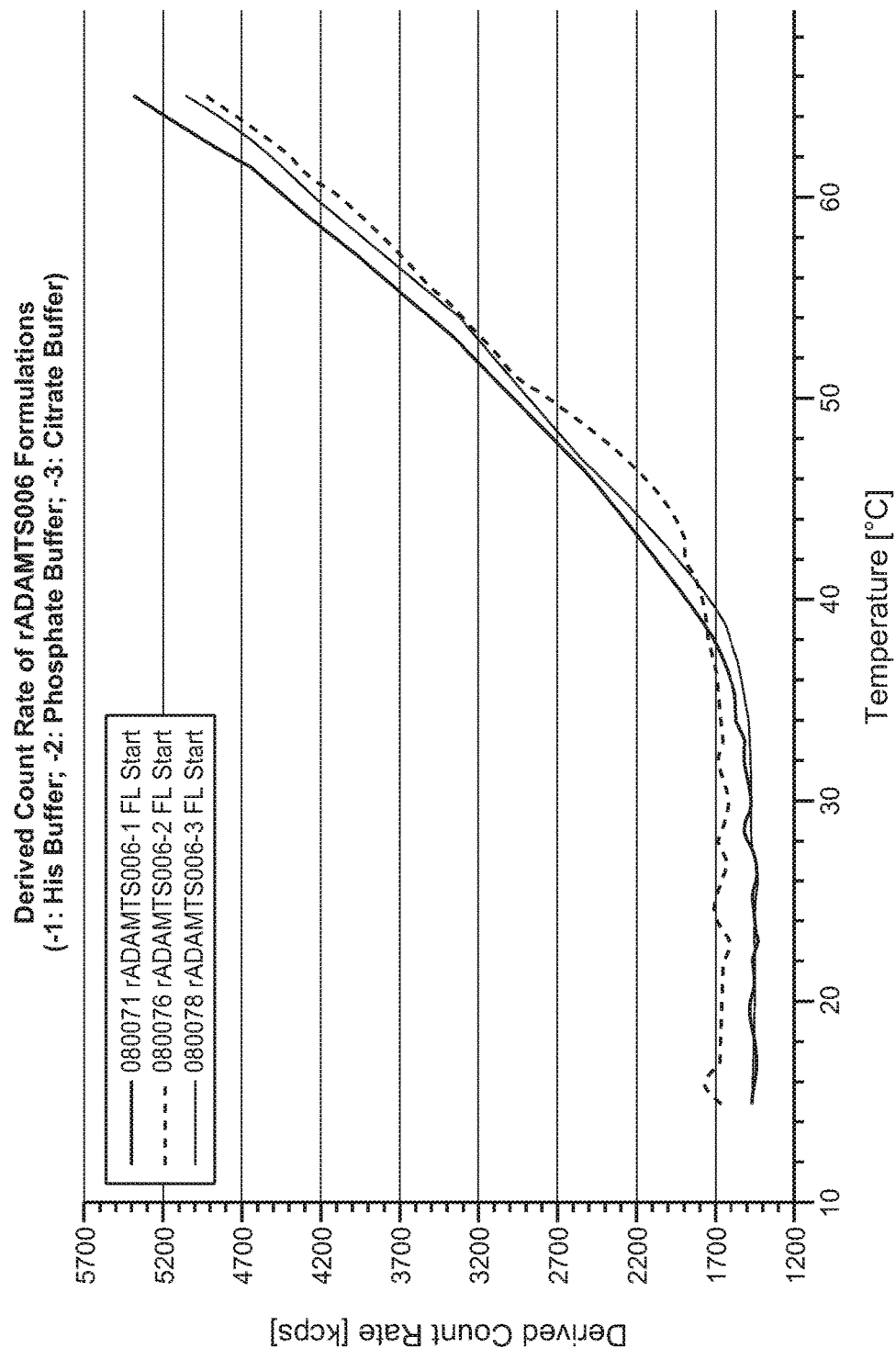

FIG. 12. Recombinant ADAMTS13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3) sodium citrate. The z-average diameter of the ADAMTS13 in the formulations was characterized by dynamic light scattering analysis.

Figure 13A:
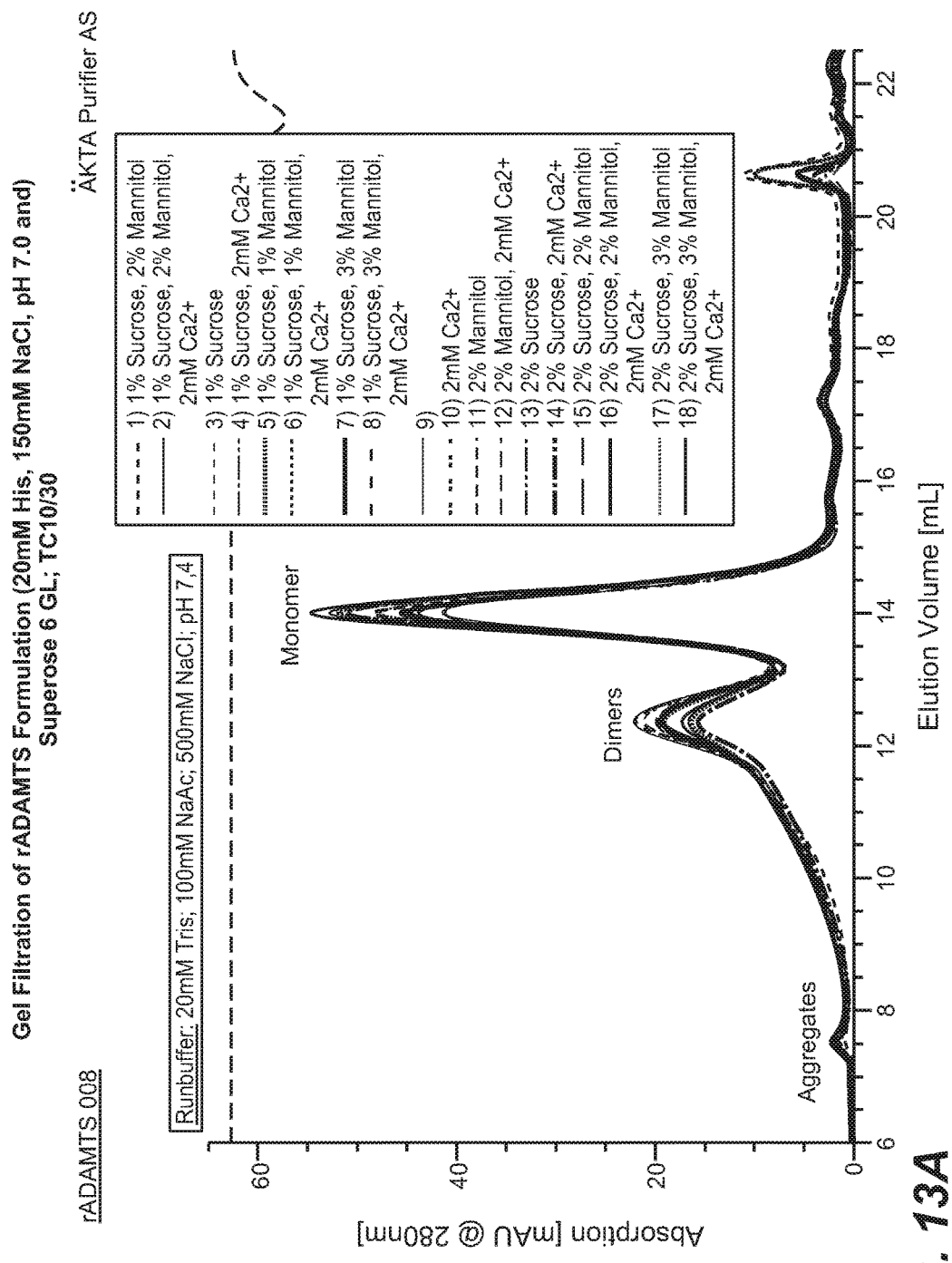
Figure 13B:
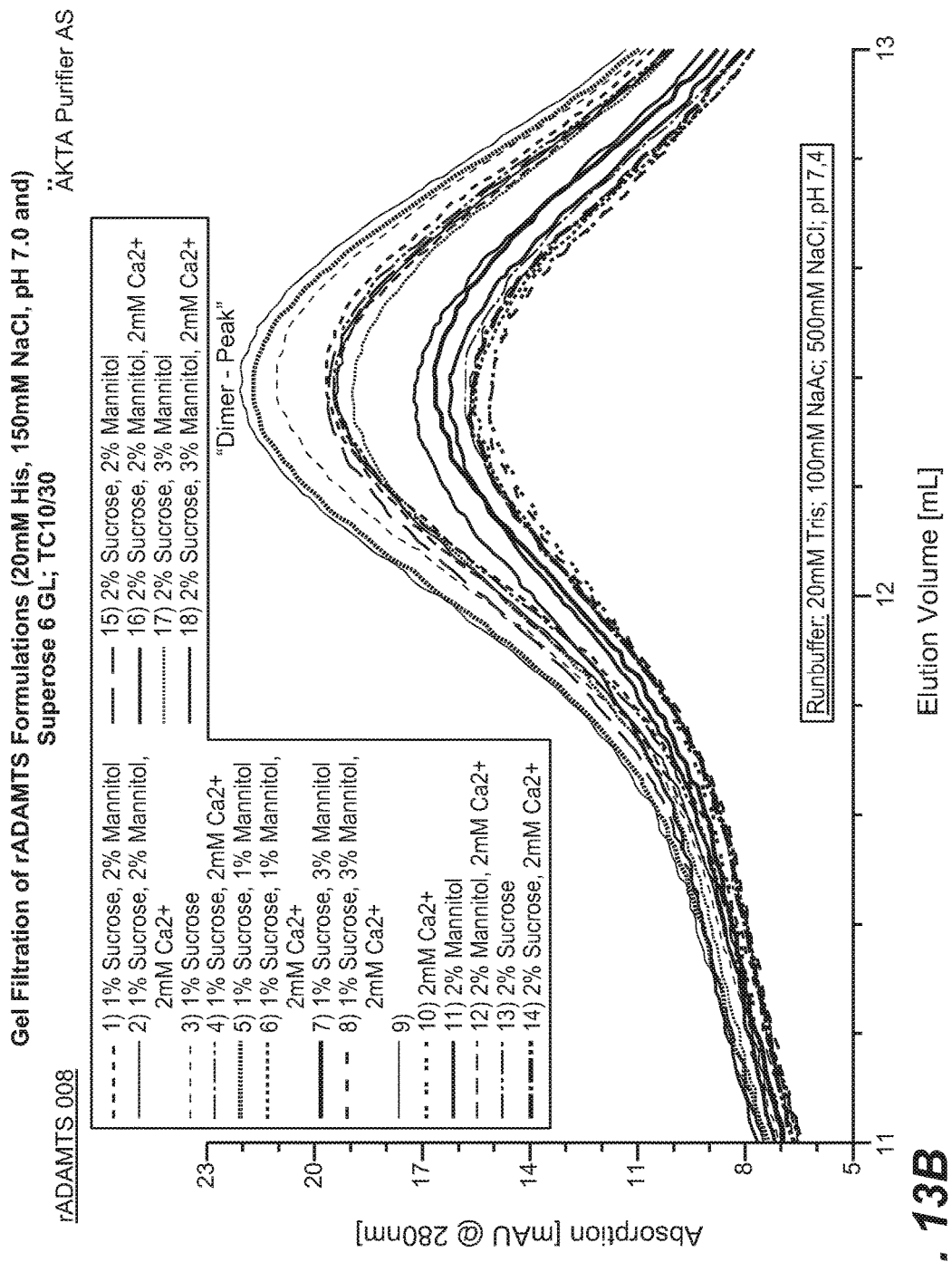

FIGS. 13A and 13B. Recombinant ADAMTS13 was formulated in buffer containing 150 mM NaCl, 0%-2% sucrose, 0%-3% mannitol, 0 mM-2 mM calcium, 0.05% polysorbate 80, and 20 mM histidine at pH 7.0 and analyzed by gel filtration. The full chromatograph is shown in panel (A), a zoomed section of the dimer-peak is shown in panel (B).

Figure 14:
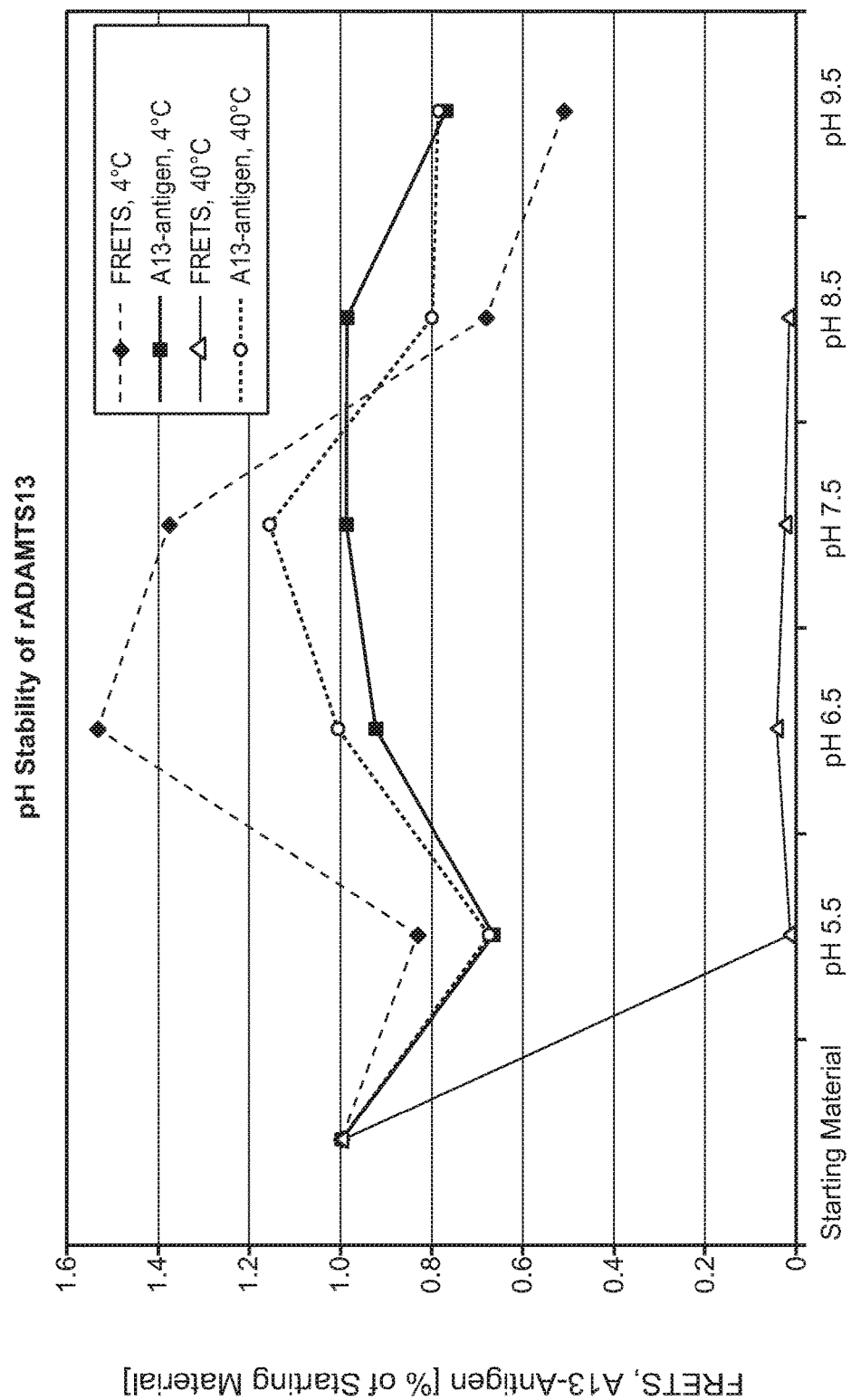

FIG. 14. Recombinant ADAMTS13 was formulated in buffer containing 150 mM NaCl and 20 mM histidine at pH 5.5, 6.5, 7.5, 8.5, and 9.5. Formulations were stored at 4° C. or 40° C. for 24 hours. FRETS-VWF73 activity and ADAMTS13 protein concentration as measured by ELISA, were then determined for the indicated pH formulations.

Figure 15:
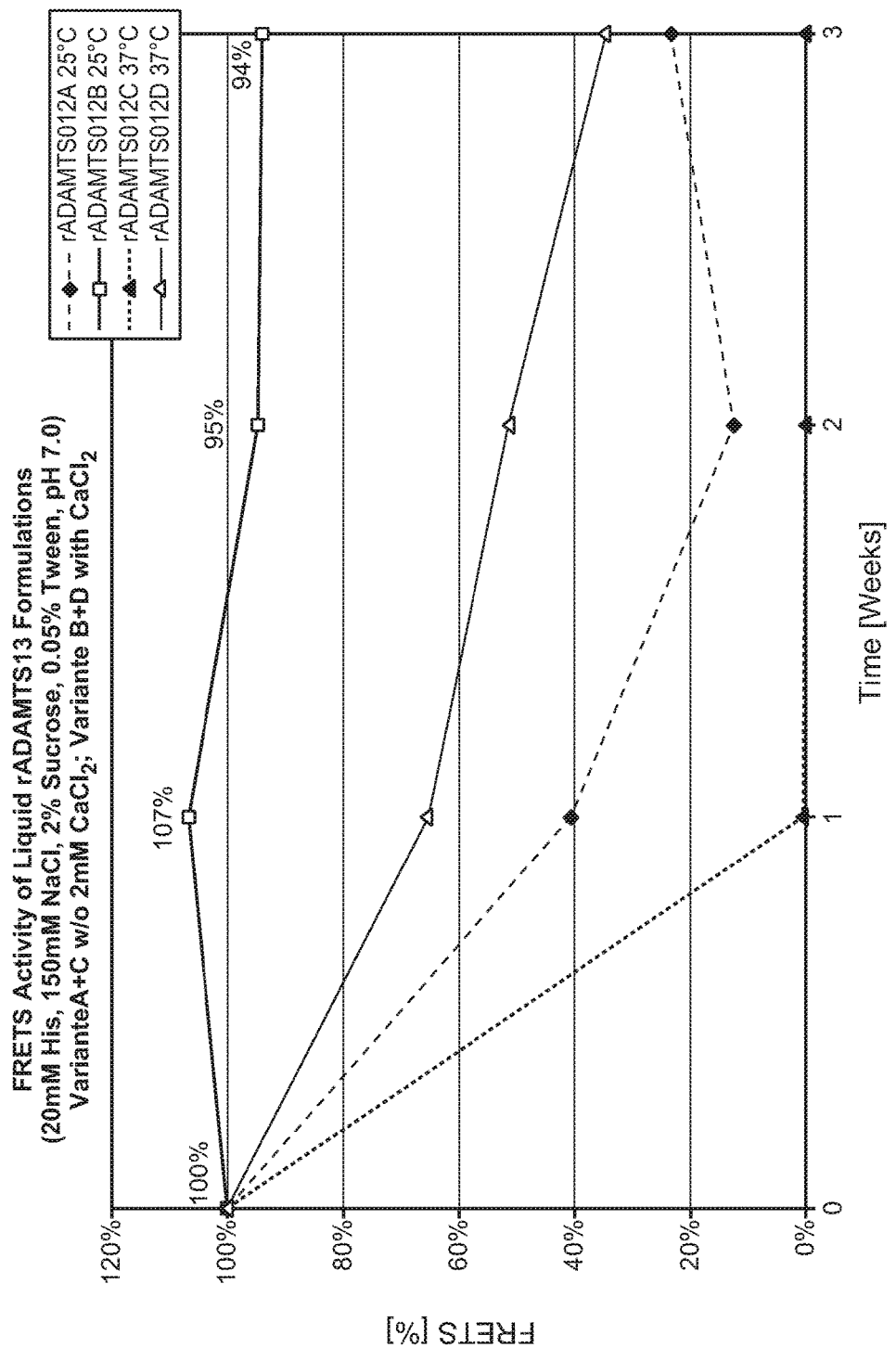

FIG. 15. Recombinant ADAMTS13 was formulated in buffer containing 150 mM NaCl, 2% sucrose, 0.05% polysorbate 80, and 20 mM histidine at pH 7.0 with (12B and D) and without (12A and C) 2 mM $CaCl_2$. The liquid formulations were stored at either 25° C. (12A and B) or 37° C. (12C and D) for three weeks. Enzyme stability was measured by FRETS-VWF73 assay at the indicated time points.

Figure 16A:
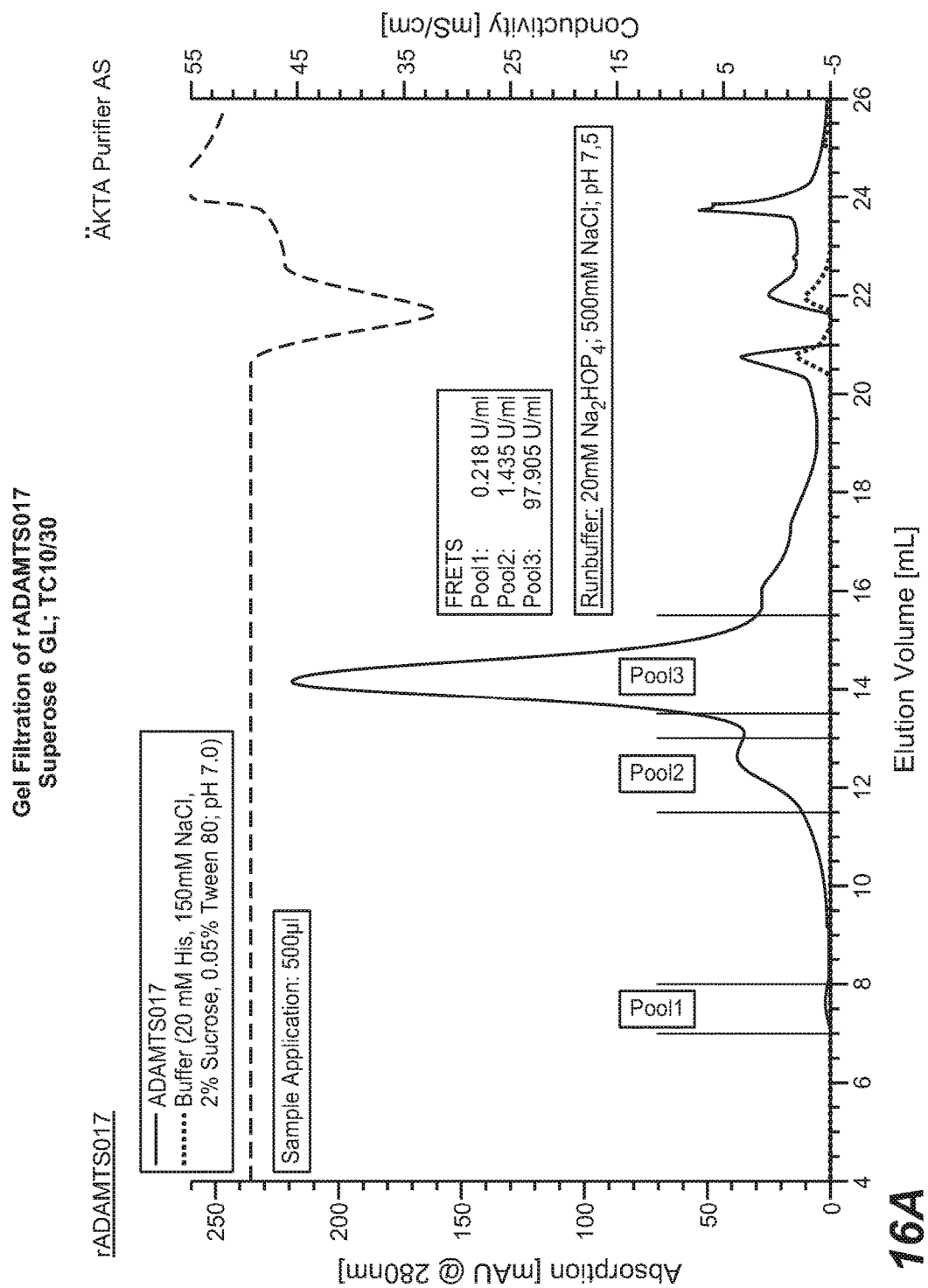
Figure 16B:
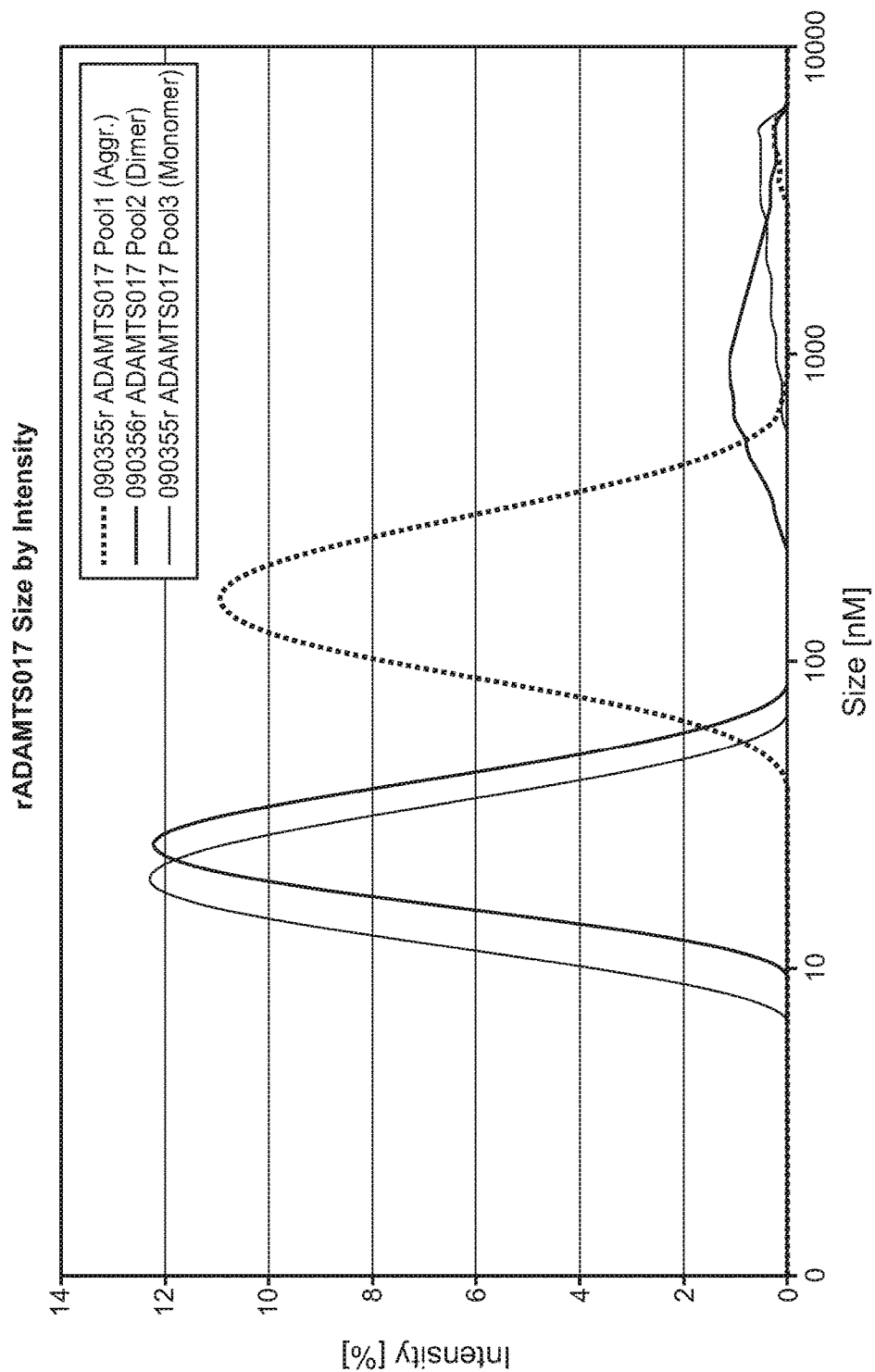

FIGS. 16A and 16B. (A) Recombinant ADAMTS13 was loaded onto a Superose 6 GL gel filtration column equilibrated with a buffer containing 20 mM $Na_2HPO_4$ (pH 7.5) and 500 mM NaCl, and molecular species were separated by size and shape. Three elution pools were created corresponding to aggregated A13 (Pool 1), dimeric A13 (Pool 2), and monomeric A13 (Pool 3). The FRETS-VWF73 activity of each pool was then determined. (B) The oligomeric state and polydispersity of the pooled fractions was further assessed by dynamic light scattering analysis.

FIGS. 17A-17F. Recombinant ADAMTS13 was formulated in buffer containing 2% sucrose, 0.05% polysorbate 80, 20 mM histidine at pH 7.0, and NaCl at (A) 0 mM, (B) 30 mM, (C) 60 mM, (D) 90 mM, (E) 120 mM, or (F) 150 mM. The formulated ADAMTS13 compositions were then lyophilized and visually inspected for the appearance of the resulting lyocake.

Figure 18:
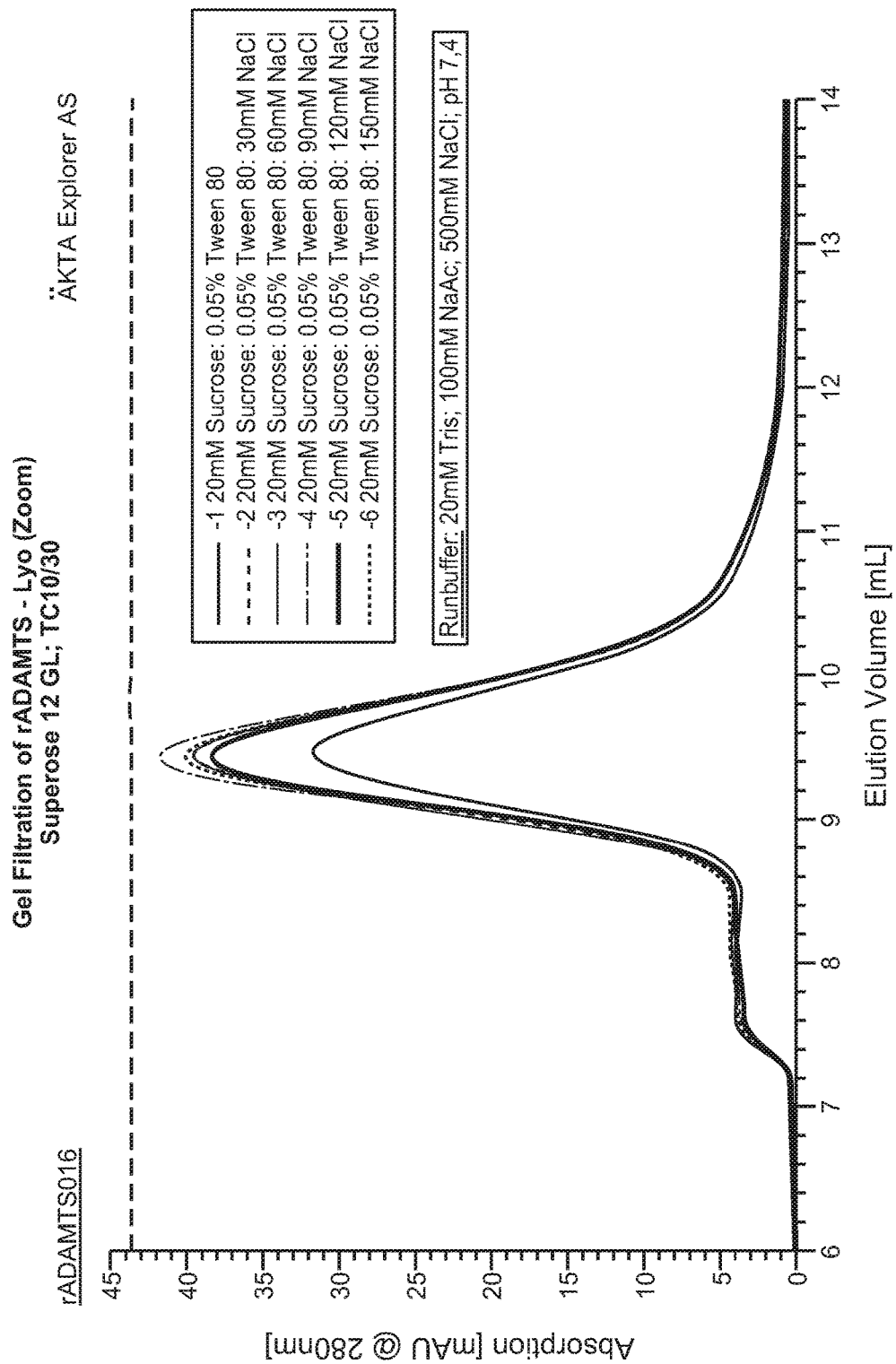

FIG. 18. Recombinant ADAMTS13 lyocakes produced from formulations containing from 0 to 150 mM NaCl were reconstituted in water. The aggregation states of the reconstituted ADAMTS13 proteins were determined by gel filtration analysis.

Figure 19:
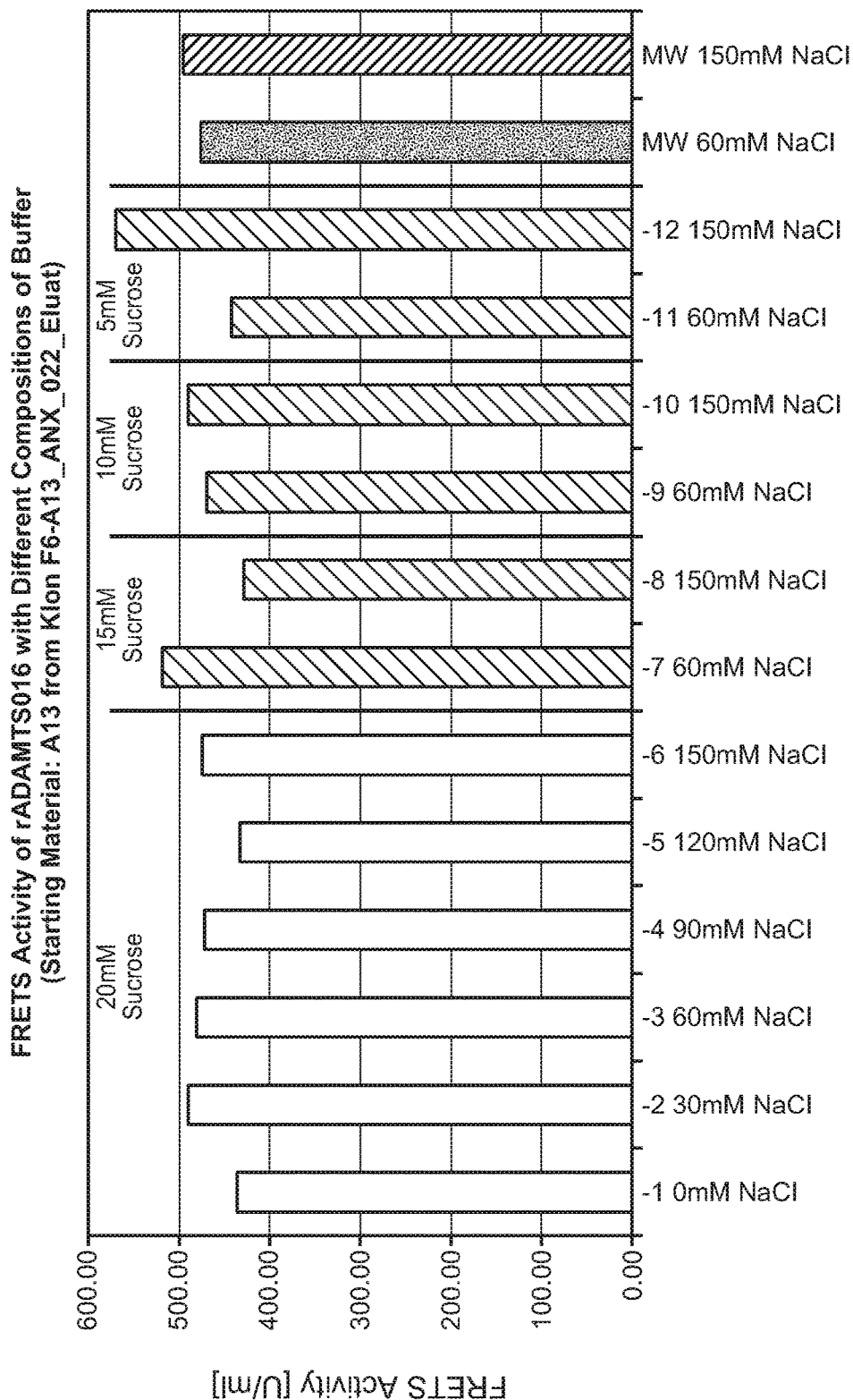

FIG. 19. Recombinant ADAMTS13 was formulated in buffer containing 0.05% polysorbate 80, 20 mM histidine at pH 7.0, sucrose at a concentration from 5 mM to 20 mM, and NaCl at a concentration from 0 to 150 mM. The activity of the ADAMTS13 protein in each formulation was determined by FRETS-VWF73 assay.

Figure 20A:
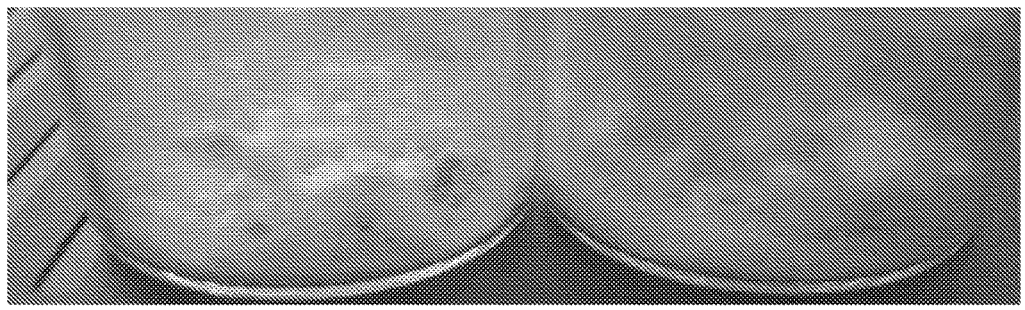
Figure 20B:
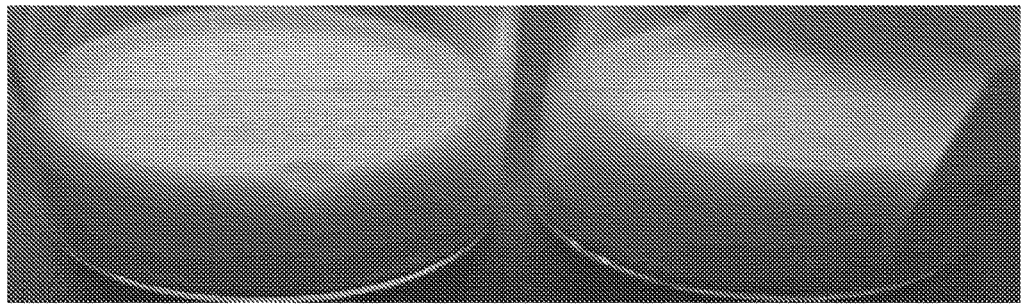

FIGS. 20A and 20B. High salt and a low salt buffers were lyophilized. The high salt buffer (A) contained 20 mM histidine (pH 7.0), 150 mM NaCl, 2% sucrose, 0.05% polysorbate 80, and 2 mM $CaCl_2$, while the low salt buffer (B) contained 20 mM histidine (pH 7.0), 30 mM NaCl, 1% sucrose, 3% mannitol, 0.05% polysorbate 80, and 2 mM $CaCl_2$. The two formulations were then lyophilized under standard conditions and the resulting lyocakes were then visually inspected.

Figure 21A:
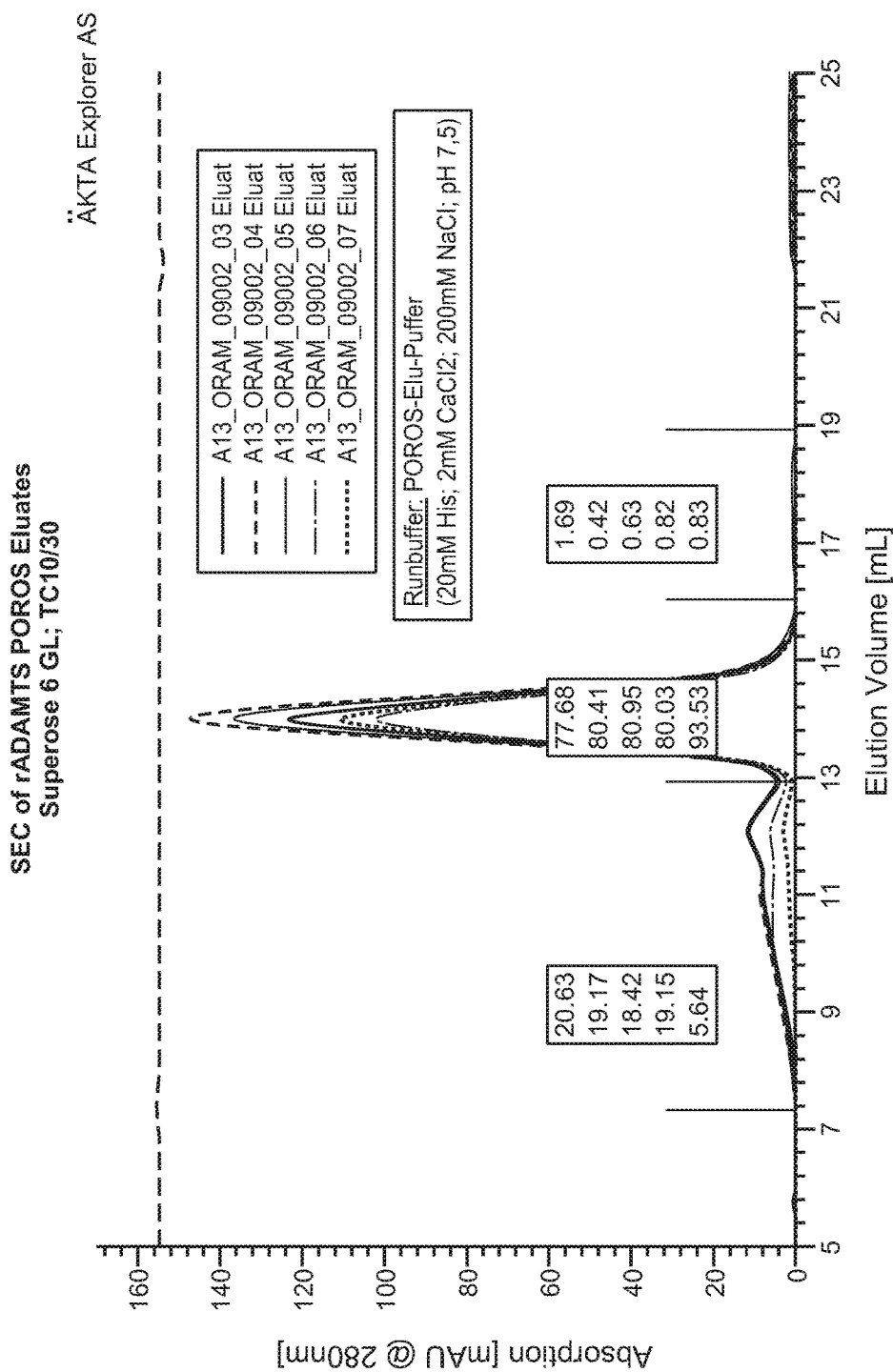
Figure 21B:
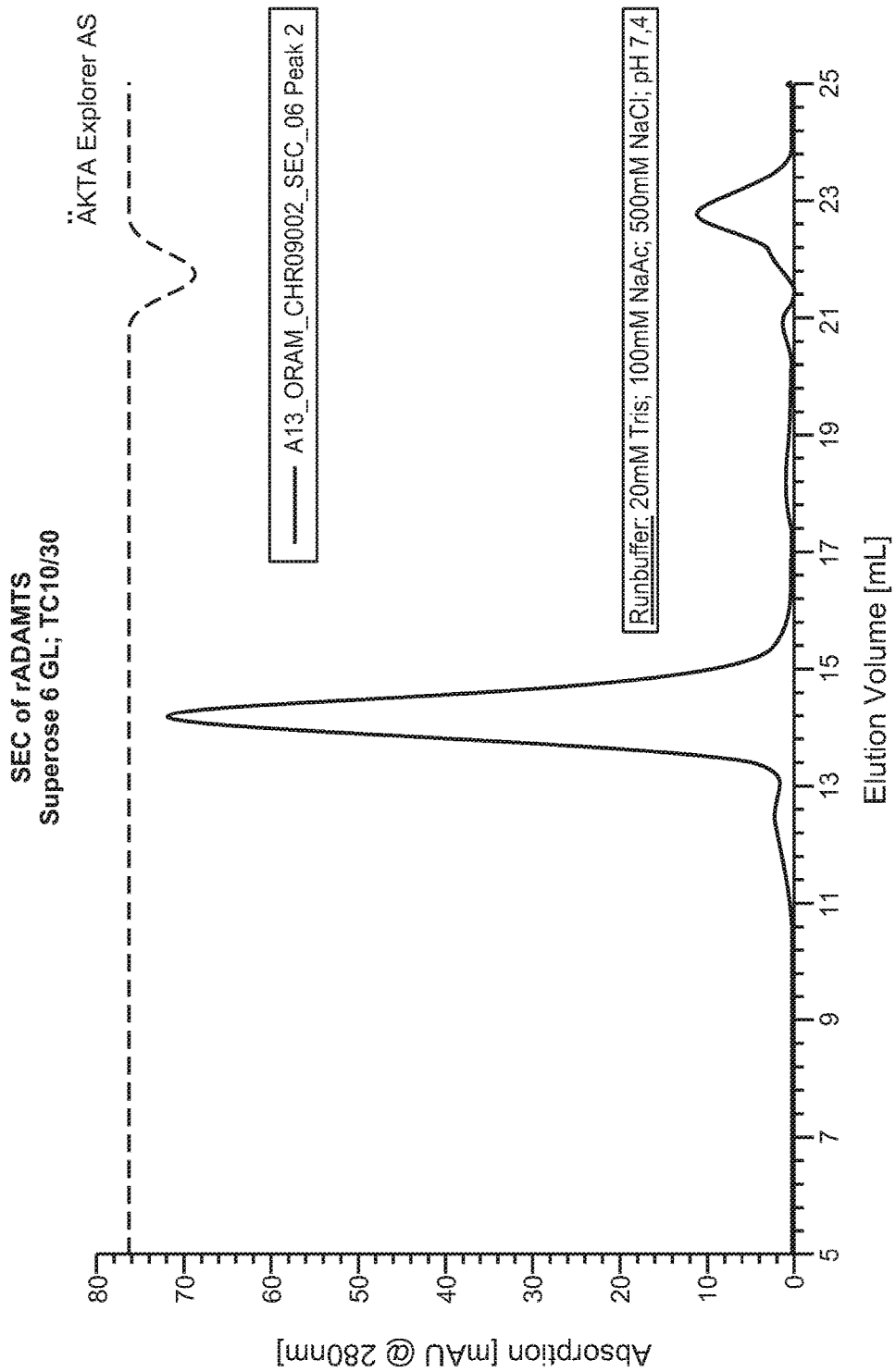

FIGS. 21A and 21B. The multimeric state of recombinant ADAMTS13 isolated by cation exchange chromatography (A) before and (B) after gel filtration was analyzed by size exclusion chromatography using a Superose 6 GL column.

Figure 22A:
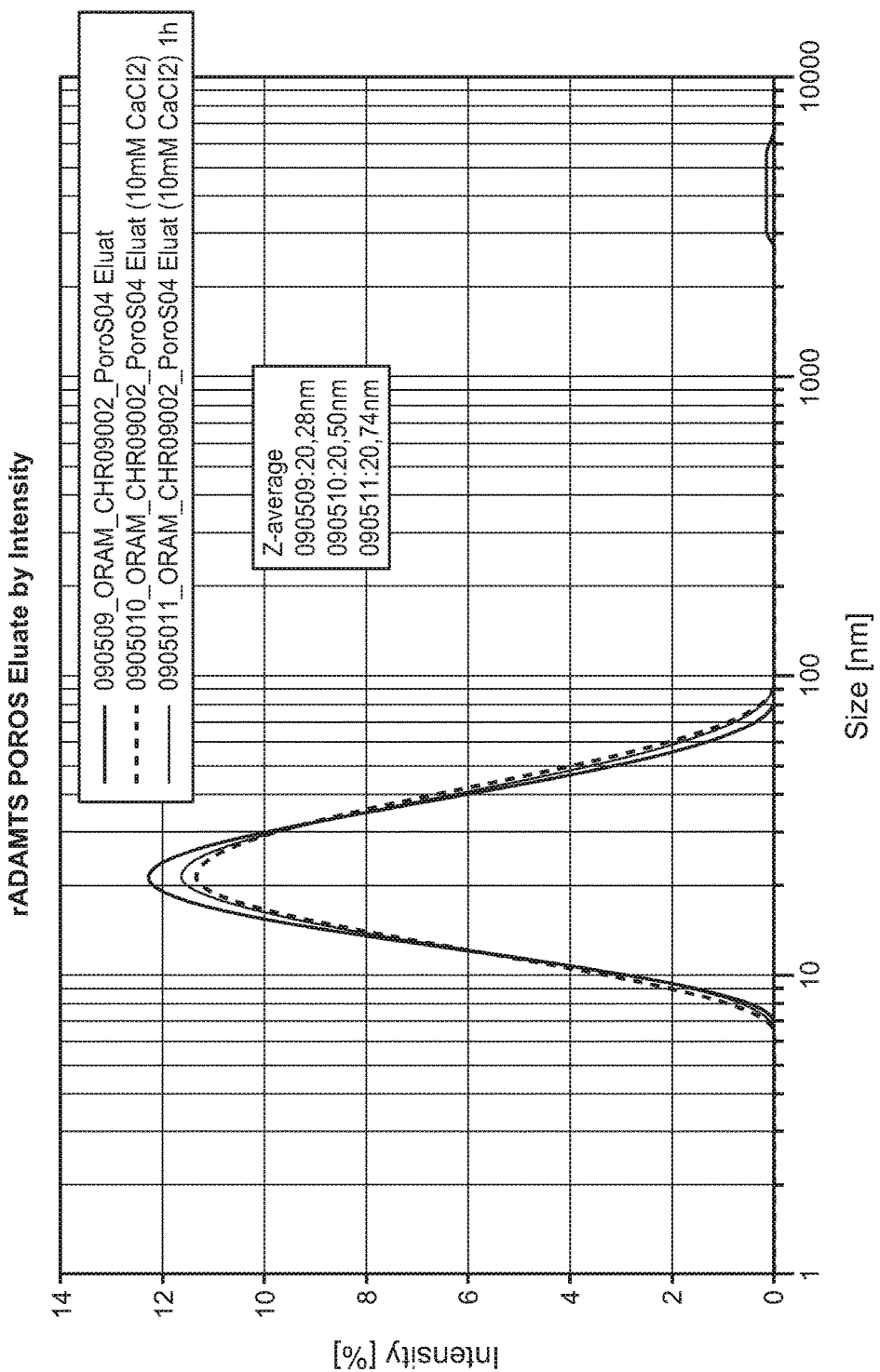
Figure 22B:
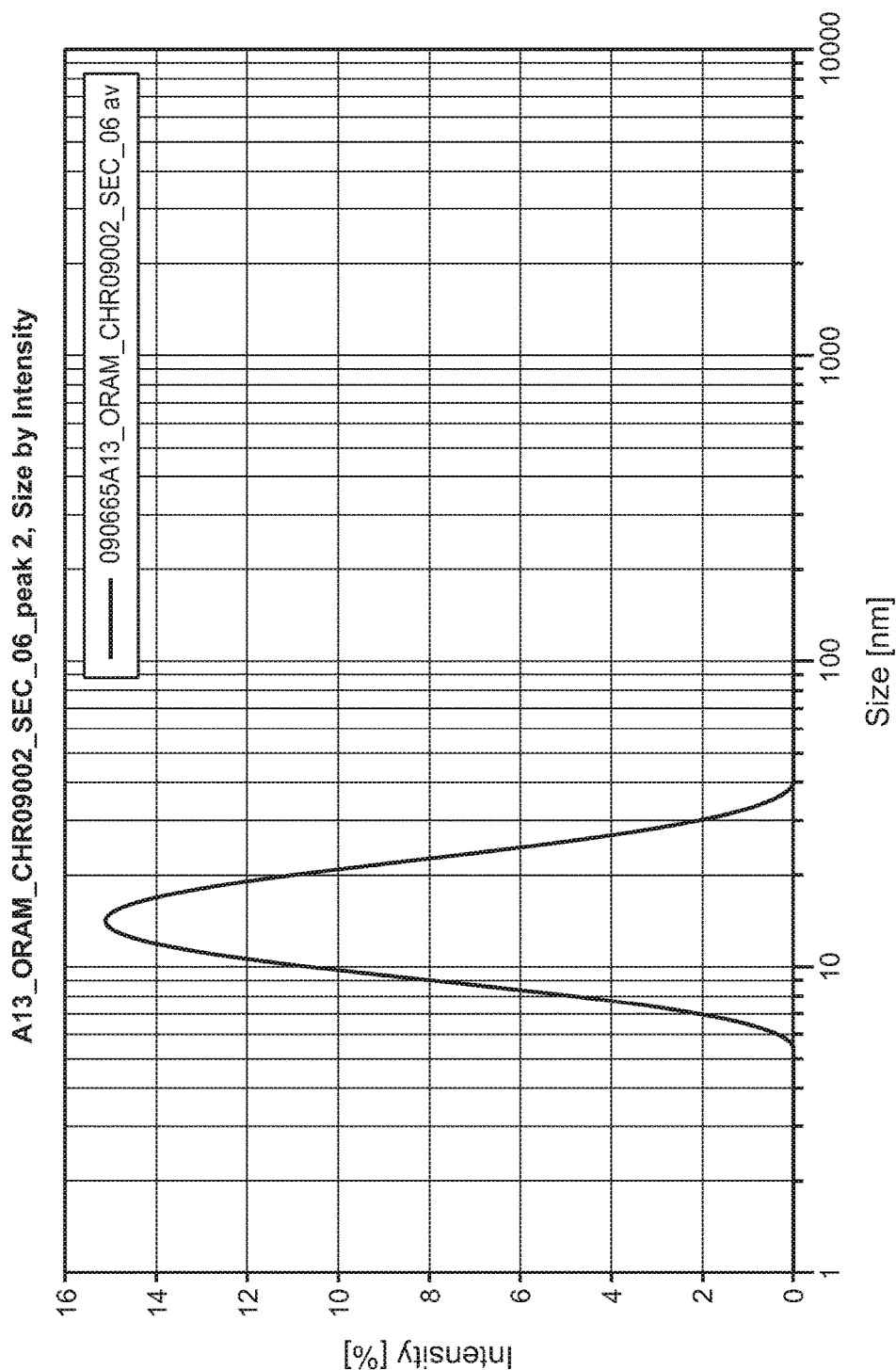

FIGS. 22A and 22B. The multimeric state of recombinant ADAMTS13 isolated by cation exchange chromatography (A) before and (B) after gel filtration was analyzed by dynamic light scattering.

Figure 23A:
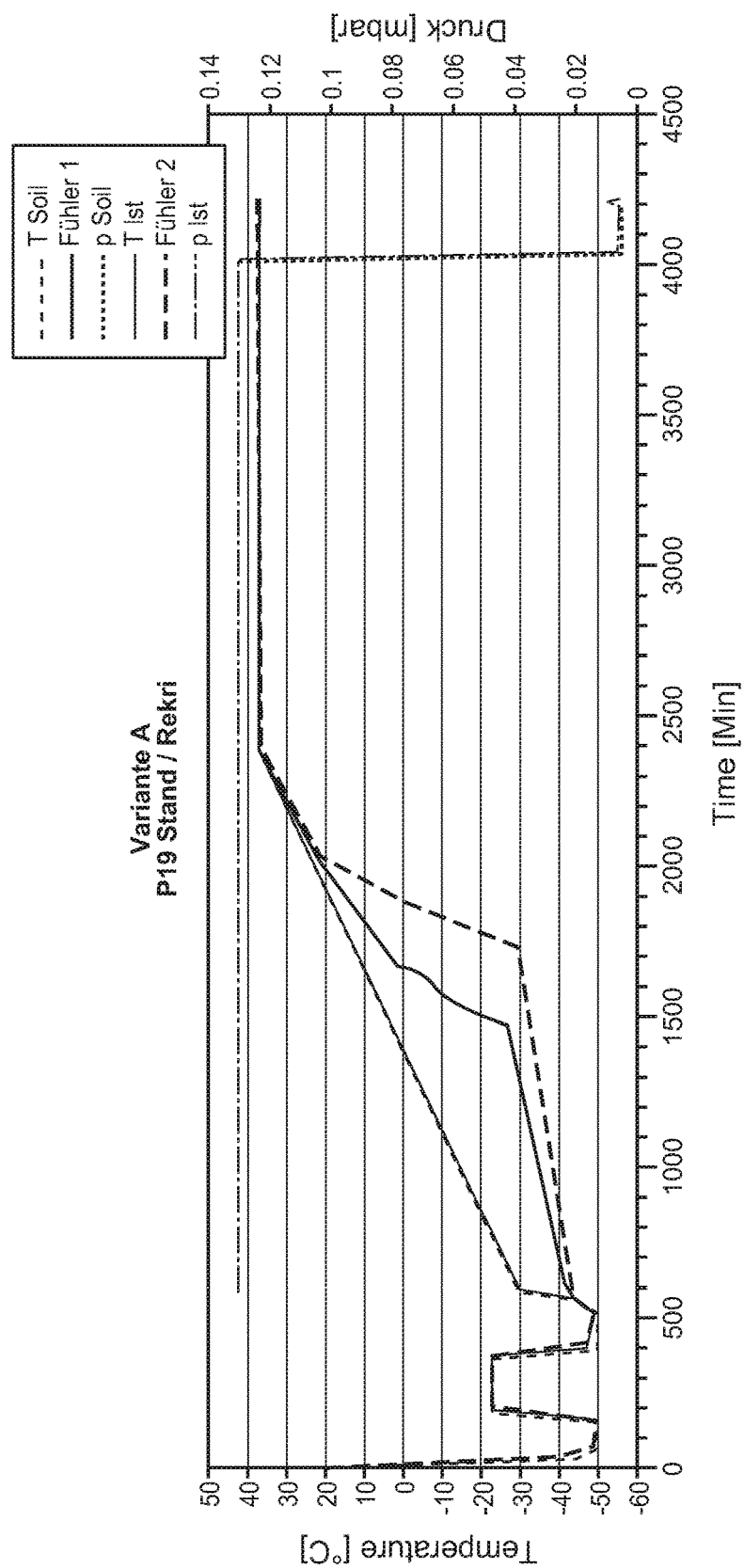
Figure 23B:
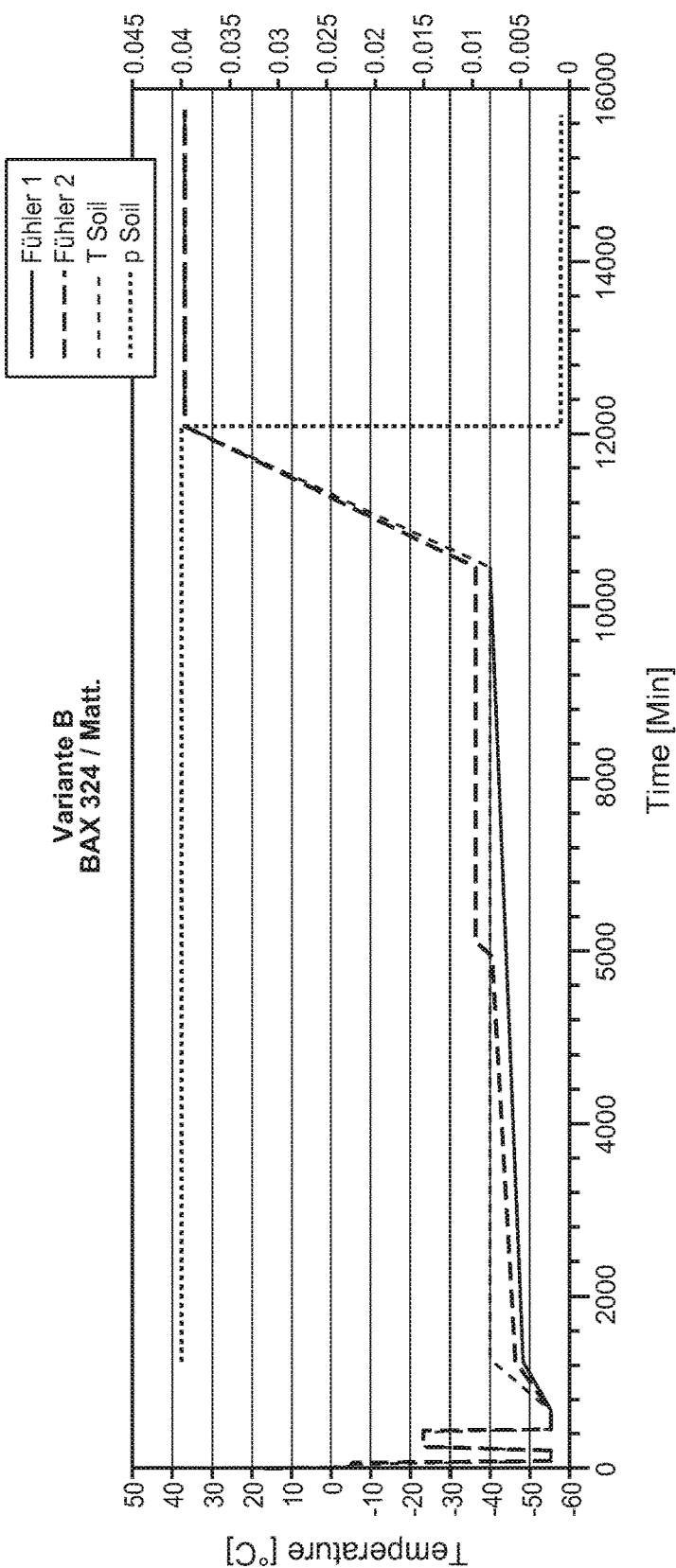
Figure 24A:
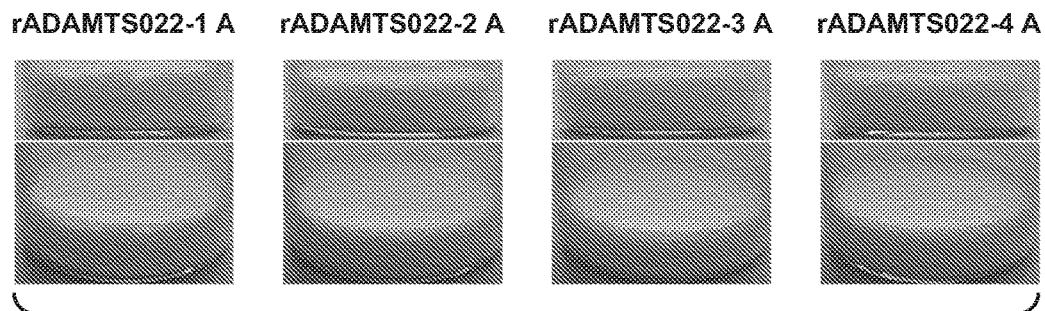
Figure 24B:
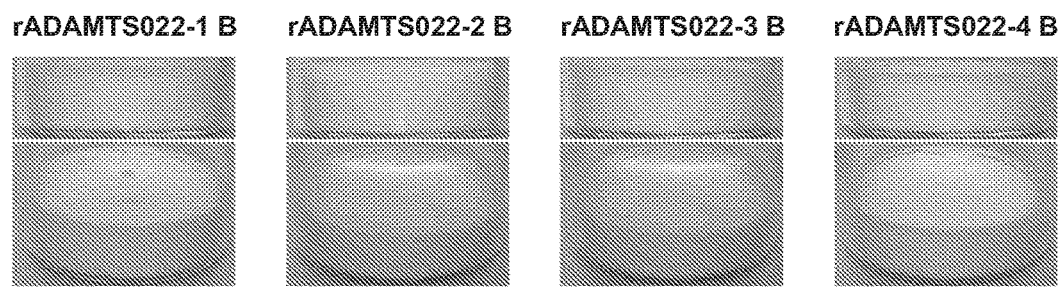
Figure 24C:
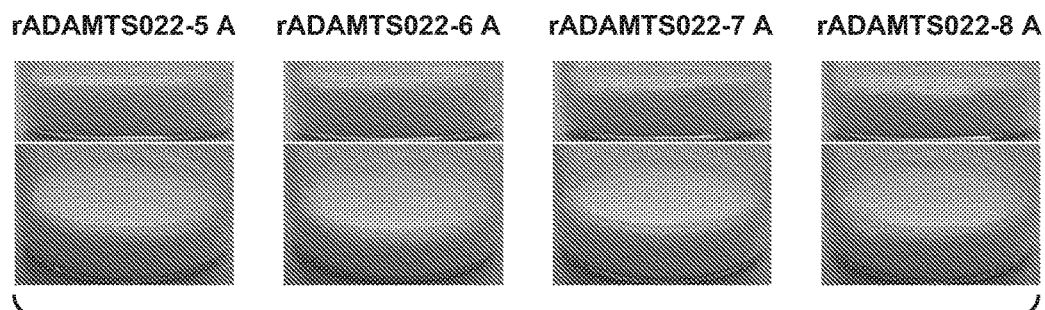
Figure 24D:
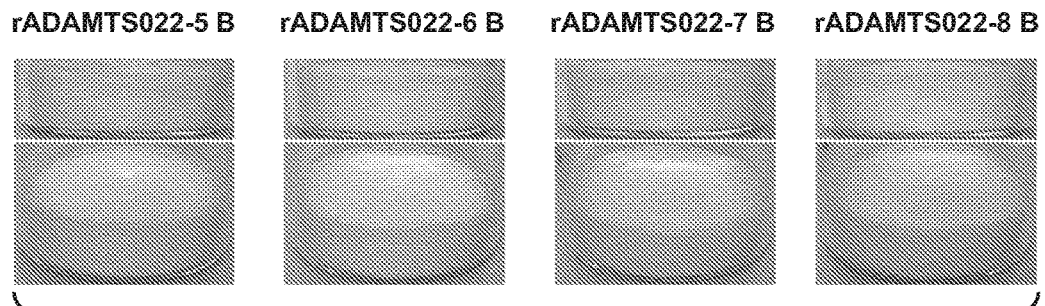

FIGS. 23A and 23B. (A) Standard and (B) extended protocols for lyophilization of rADAMTS13 formulations.

FIGS. 24A-24D. Comparison of rADAMTS13 lyocakes produced by lyophilization of (A) rA13 formulations 1 to 4 using a standard lyophilization protocol, (B) rA13 formulations 1 to 4 using an extended lyophilization protocol, (C) rA13 formulations 5 to 8 using a standard lyophilization protocol, and (D) rA13 formulations 5 to 8 using an extended lyophilization protocol. Formulations and lyophilization protocols used for the generation of this data can be found in example 12.

Figure 25A:
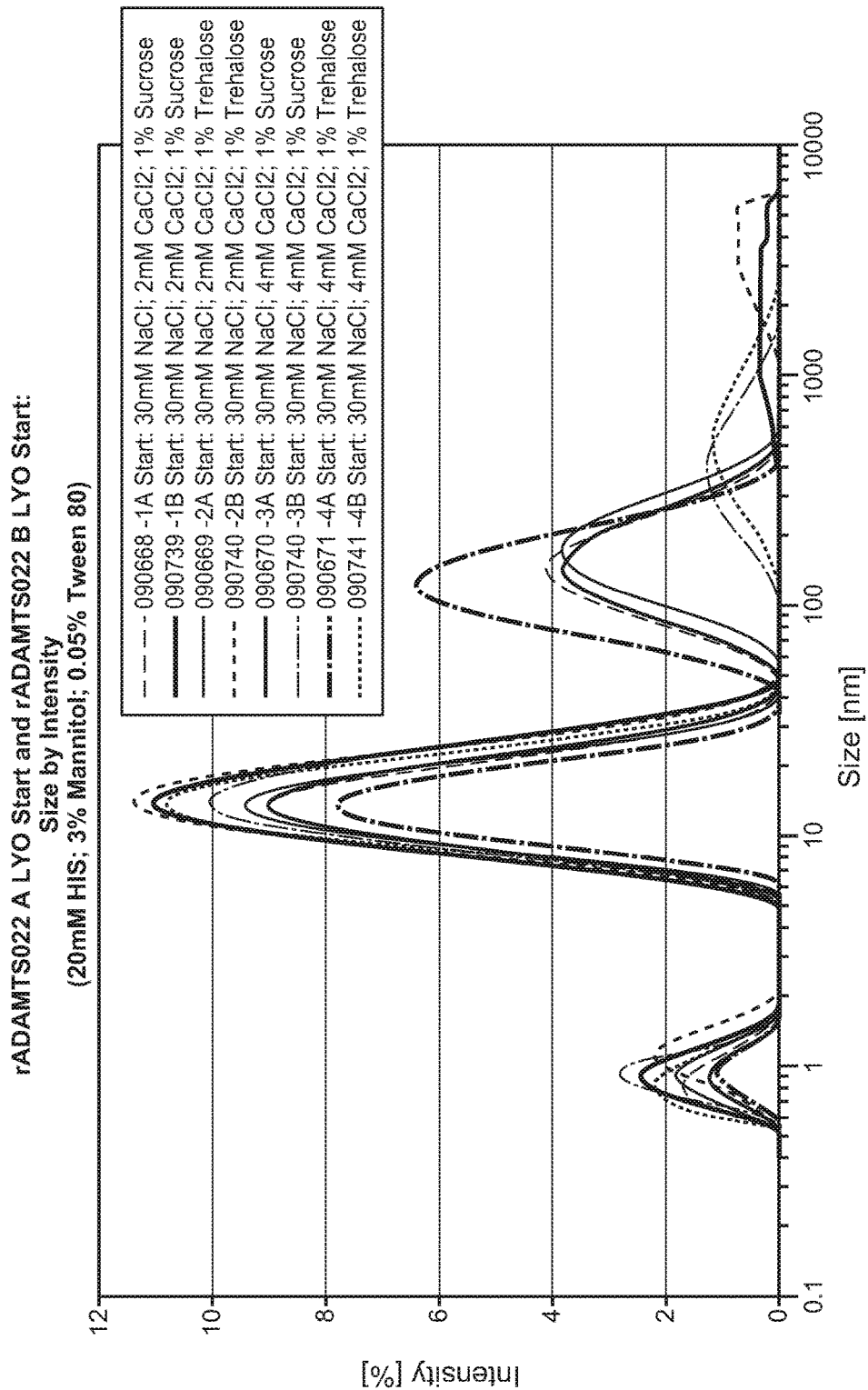
Figure 25B:
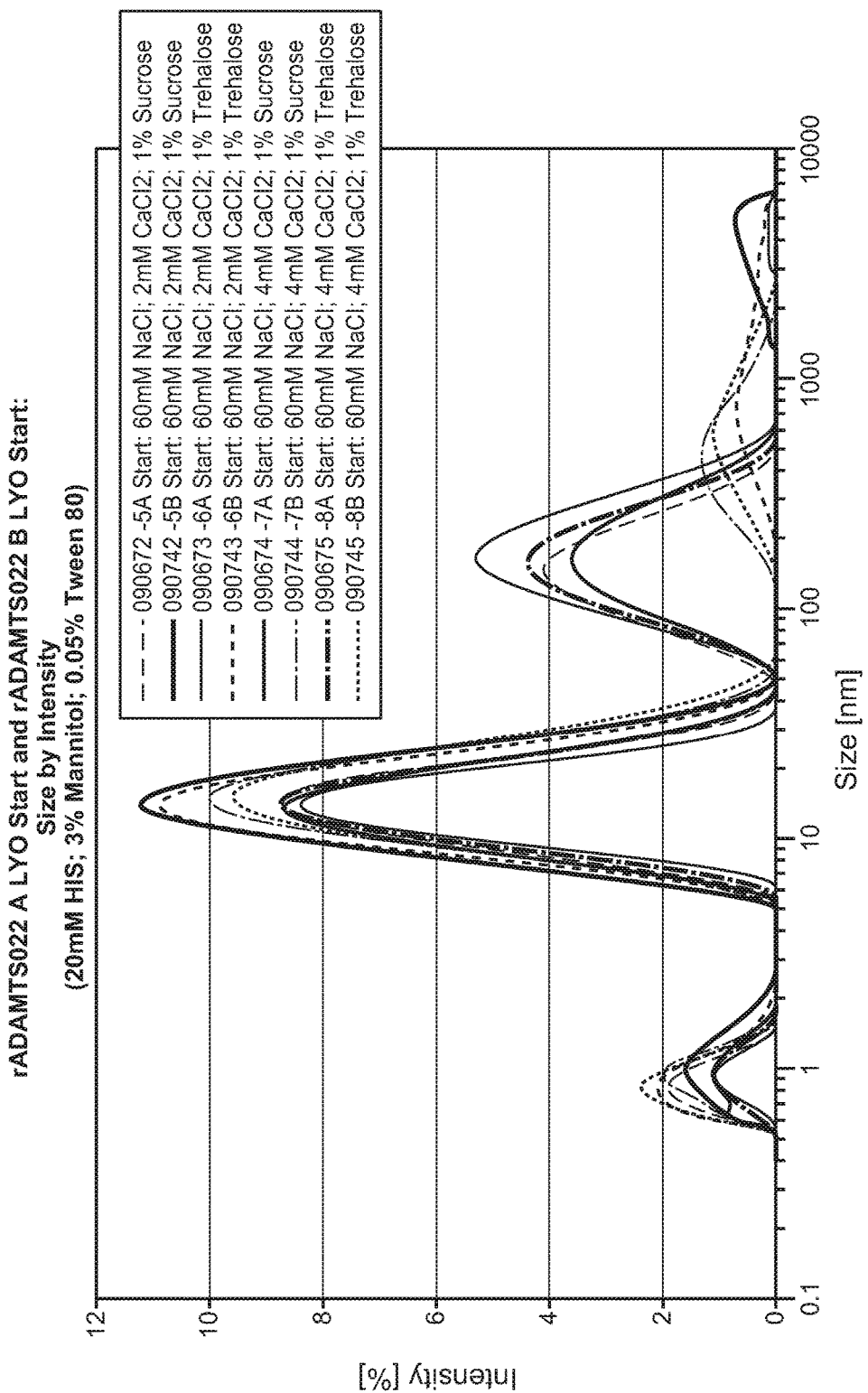

FIGS. 25A and 25B. The oligomeric state and polydispersity of ADAMTS13 compositions formulated with (A) 30 mM NaCl or (B) 60 mM NaCl was assessed by dynamic light scattering analysis after lyophilization with a standard or extended protocol.

Figure 26:
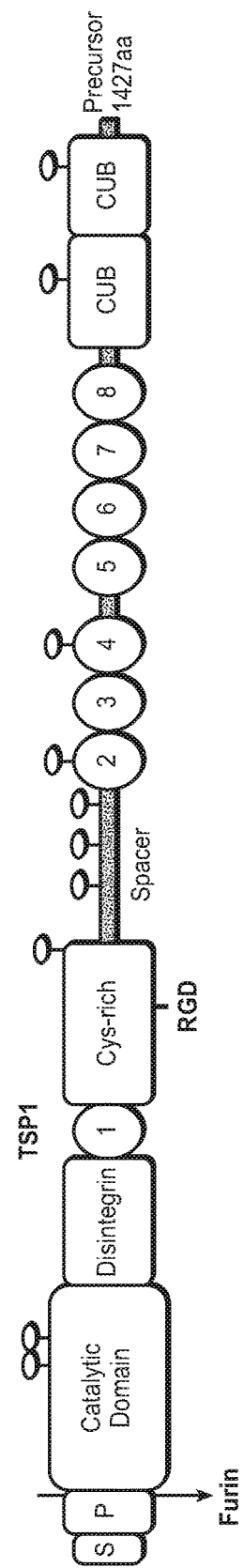

FIG. 26. Domain structure of human von Willebrand factor (VWF)-cleaving protease ADAMTS13. The precursor ADAMTS13 polypeptide consists of a signal peptide (S), a propeptide (P), followed by the structural features of the mature polypeptide comprising a catalytic metalloprotease domain, a disintegrinlike domain, a thrombospondin type 1 (TSP1) motif, a cysteine-rich and spacer domain, 7 additional TSP1 repeats and 2 CUB domains. Ten potential N-glycosylation sites are marked by closed circles.

Figure 27:
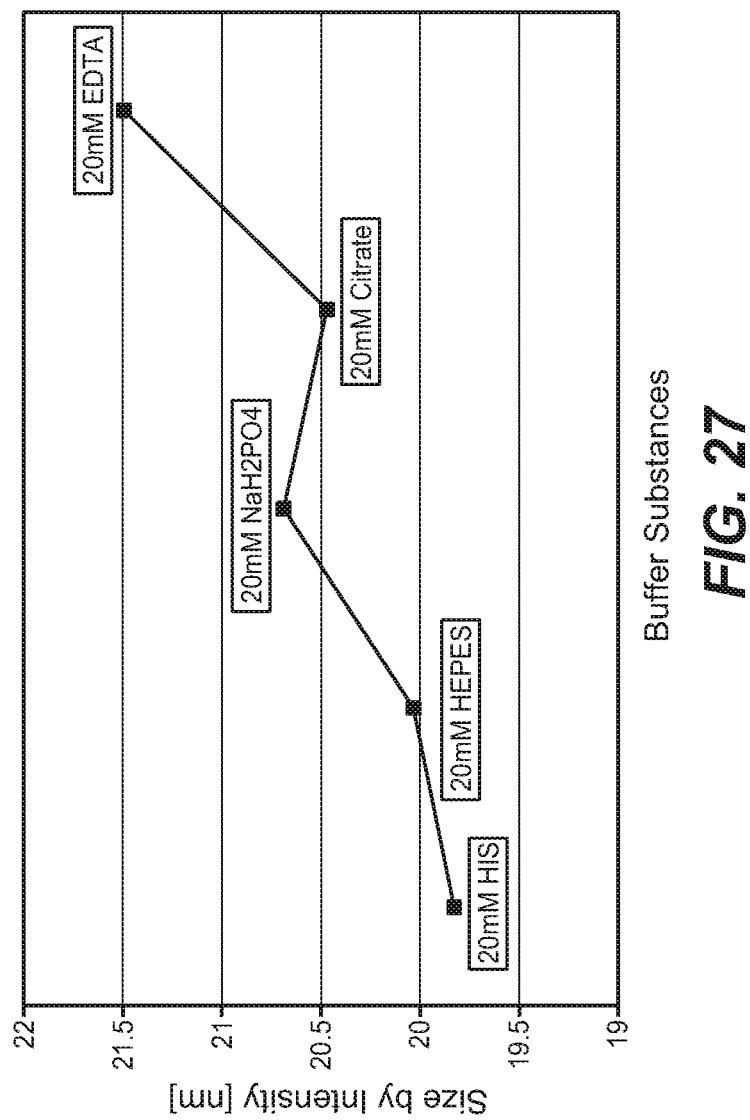

FIG. 27. Hydrodynamic diameters of ADAMTS13 compositions formulated with different buffering agents as determined by dynamic light scattering analysis (DLS).

Figure 28:
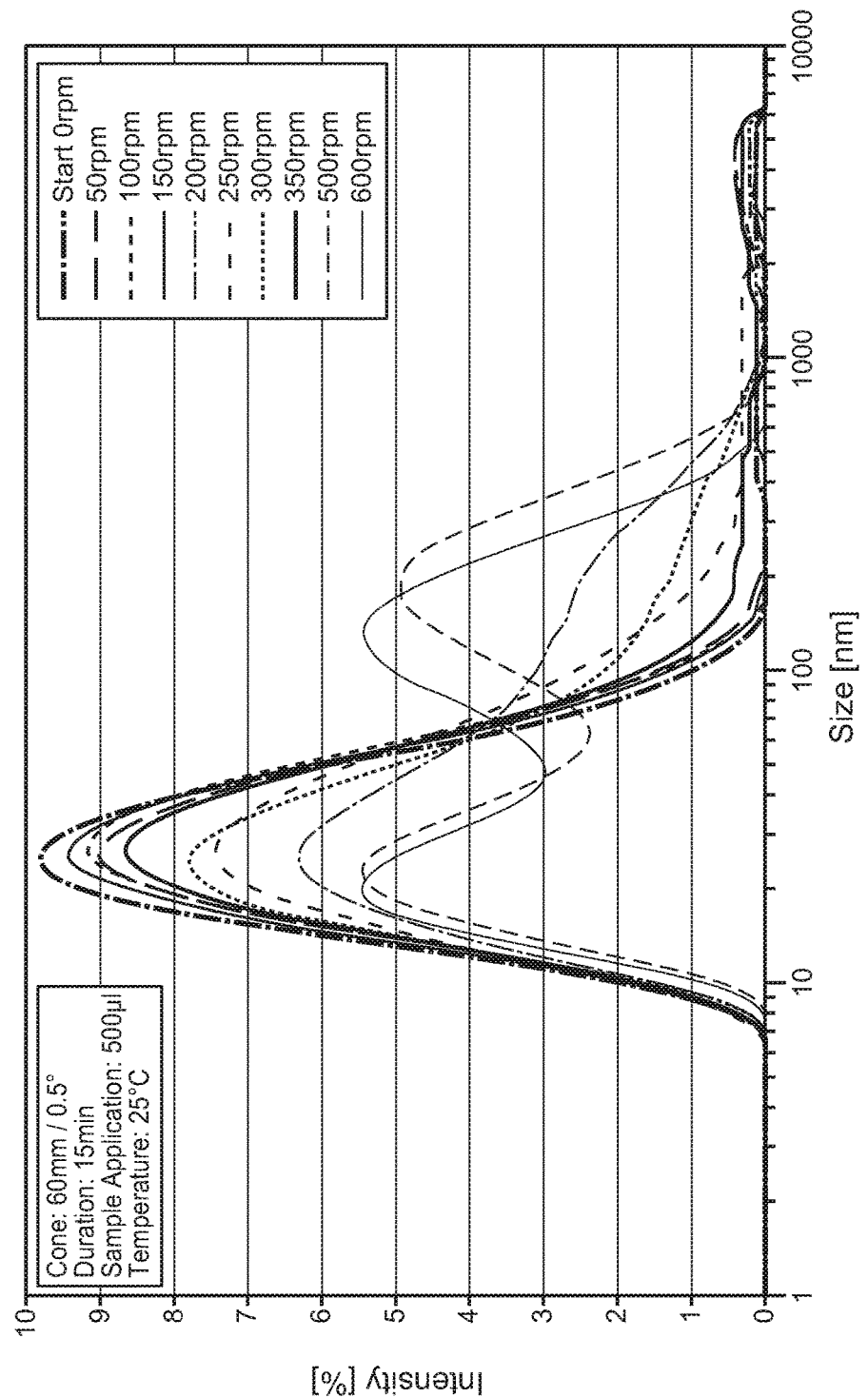

FIG. 28. Influence of shear stress on recombinant human ADAMTS13 as determined by dynamic light scattering analysis (DLS).

Figure 29:
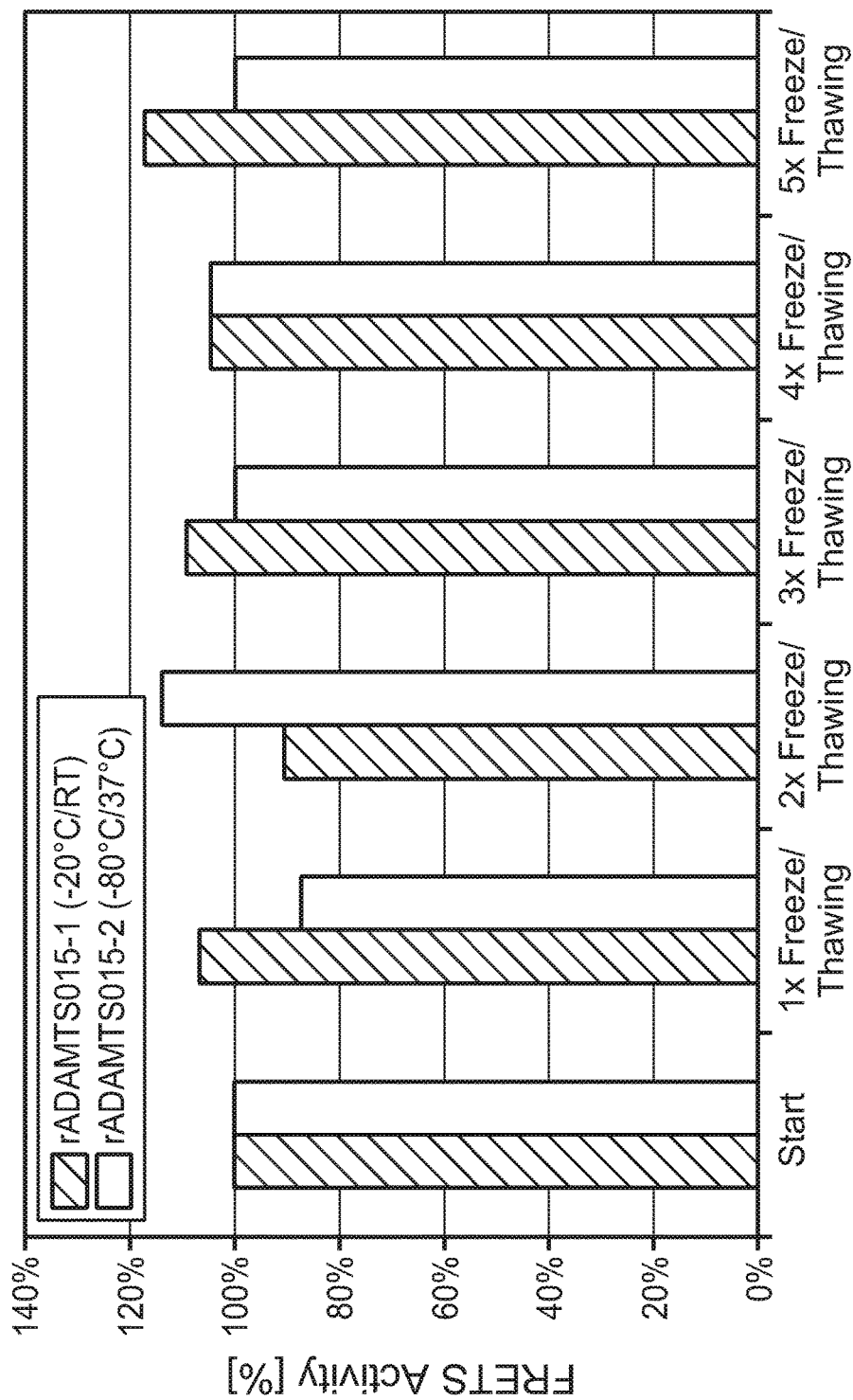

FIG. 29. Freeze-thaw stability of recombinant human ADAMTS13 as determined by FRETS activity.

Figure 30A:
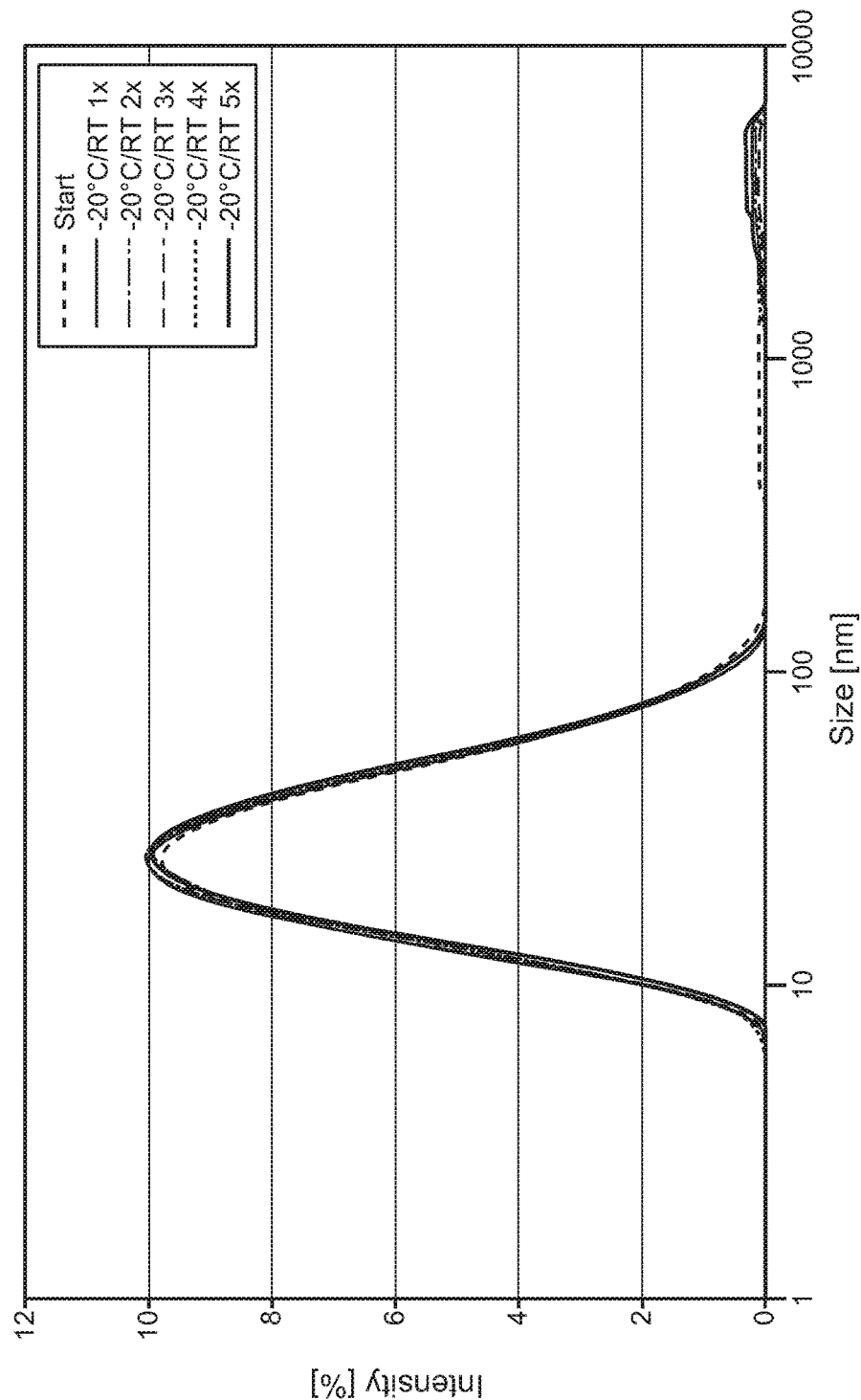
Figure 30B:
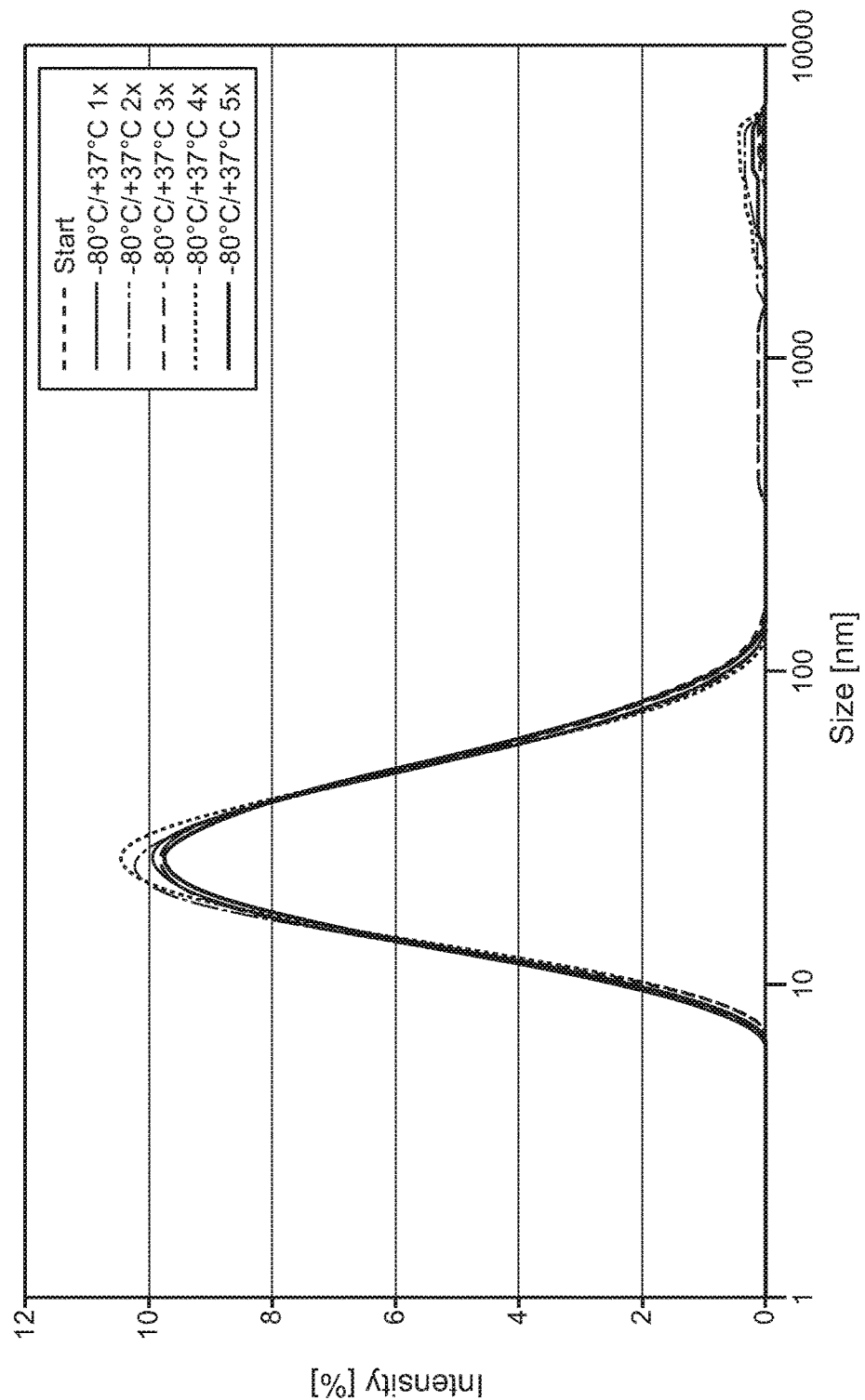

FIGS. 30A and 30B. Freeze-thaw stability of recombinant human ADAMTS13 as determined by dynamic light scattering analysis (DLS).

Figure 31:
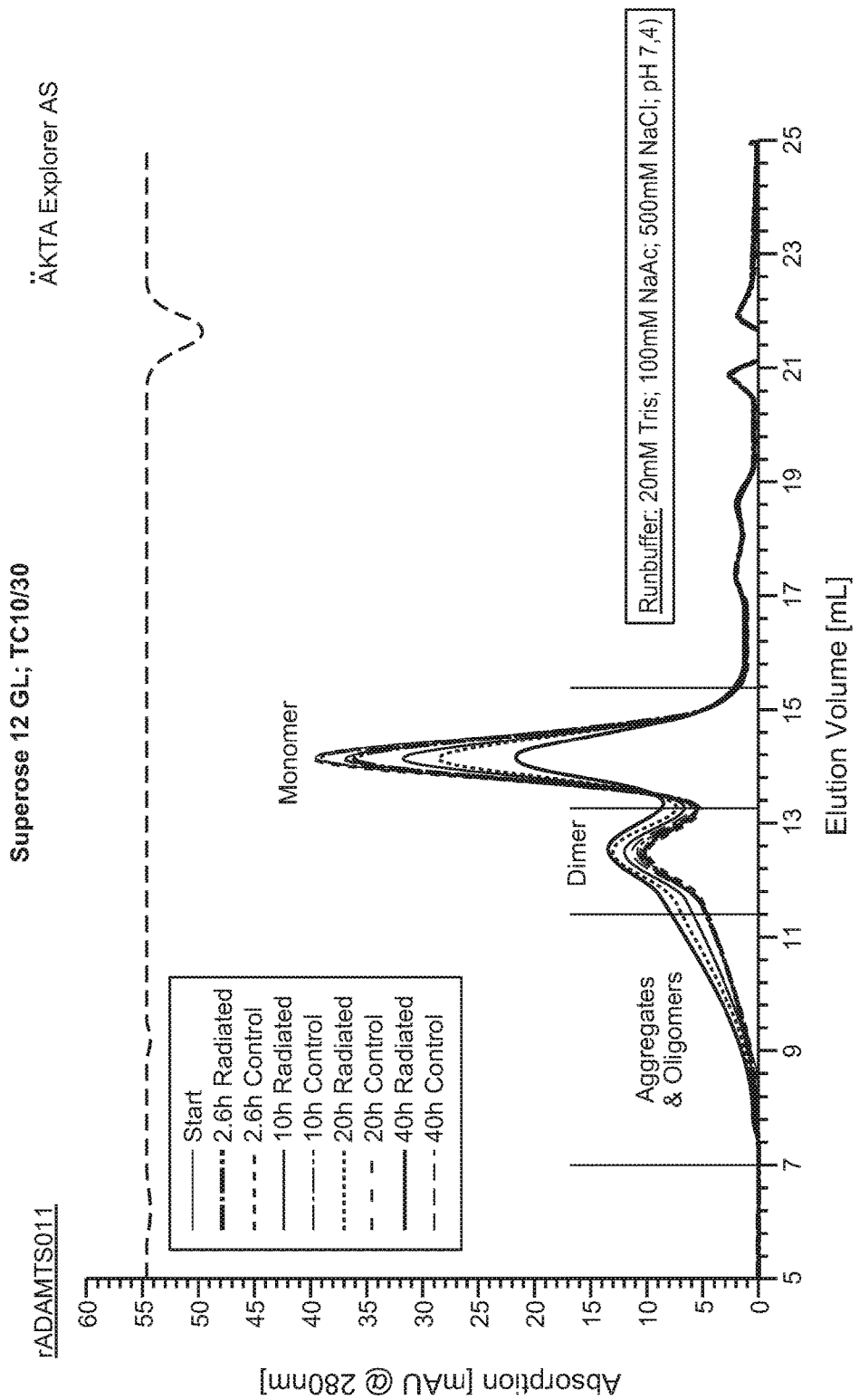

FIG. 31. Photostability of lyophilized recombinant human ADAMTS13 as determined by SE-HPLC.

Figure 32A:
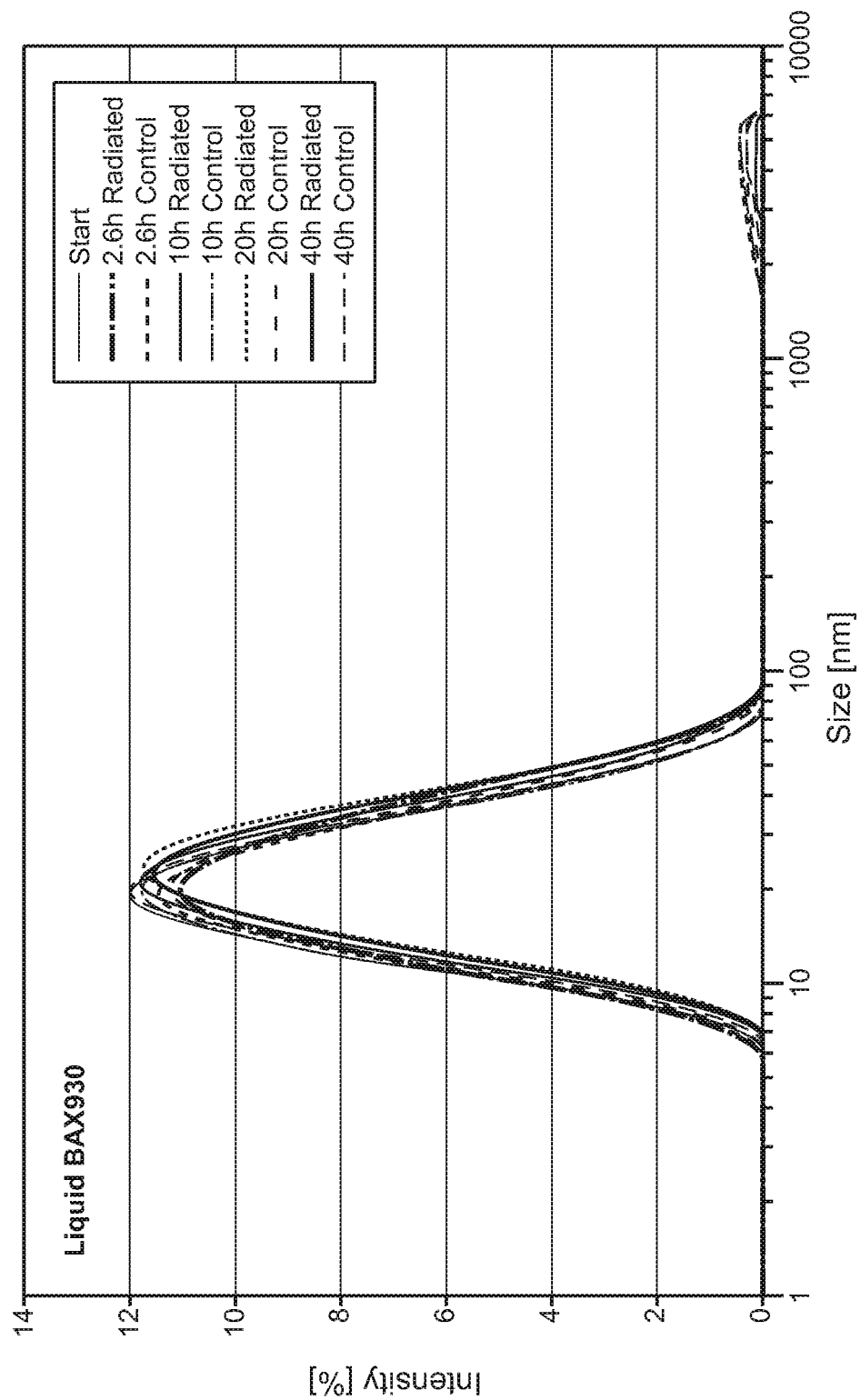
Figure 32B:
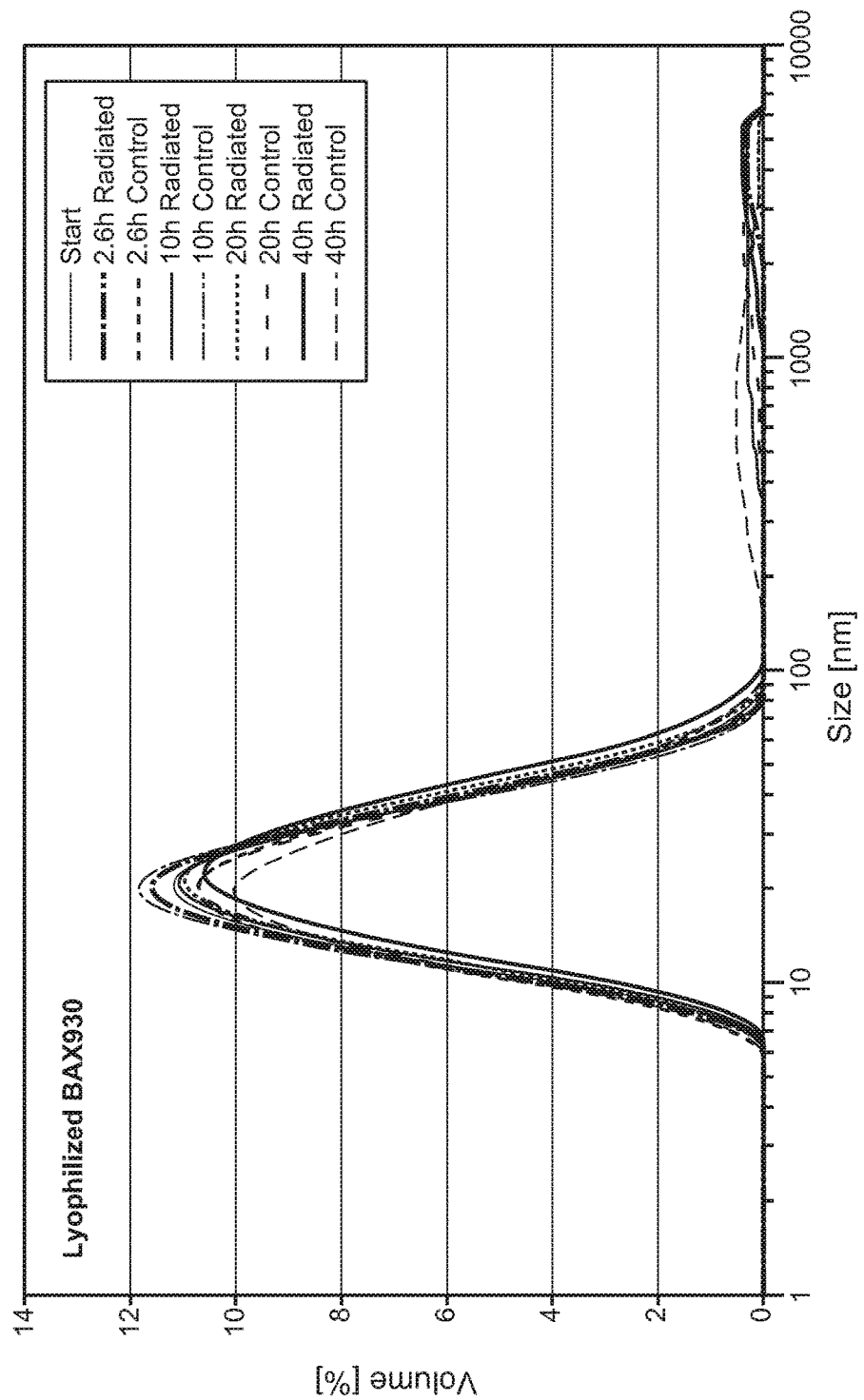

FIGS. 32A and 32B. Photostability of liquid and lyophilized recombinant human ADAMTS13 as determined by dynamic light scattering analysis (DLS).

Figure 33:
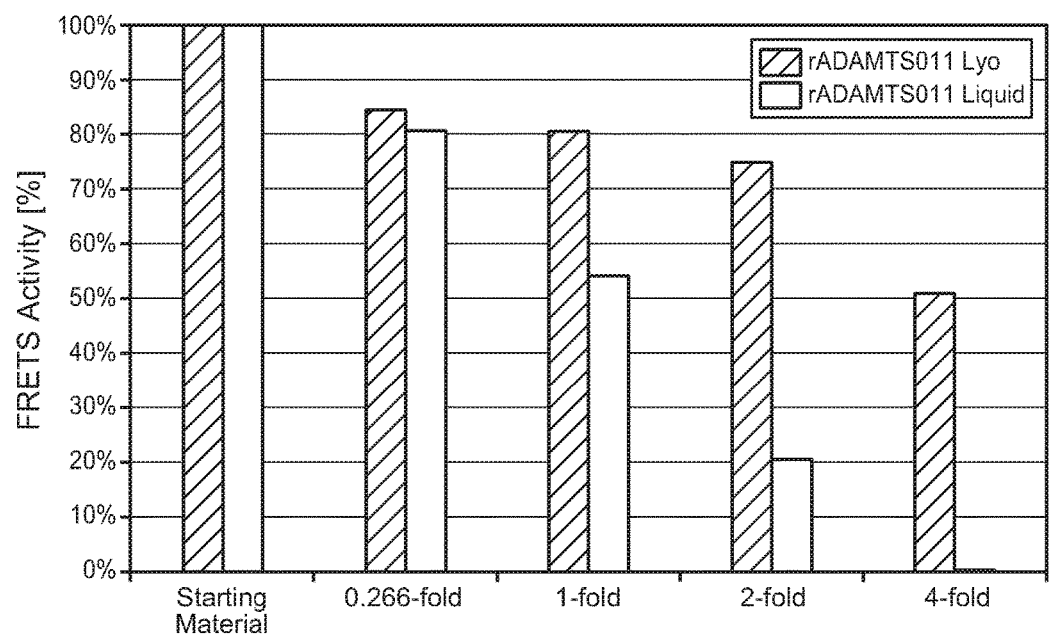

FIG. 33. Photostability of liquid and lyophilized recombinant human ADAMTS13 as determined by FRETS activity.

Figure 34:
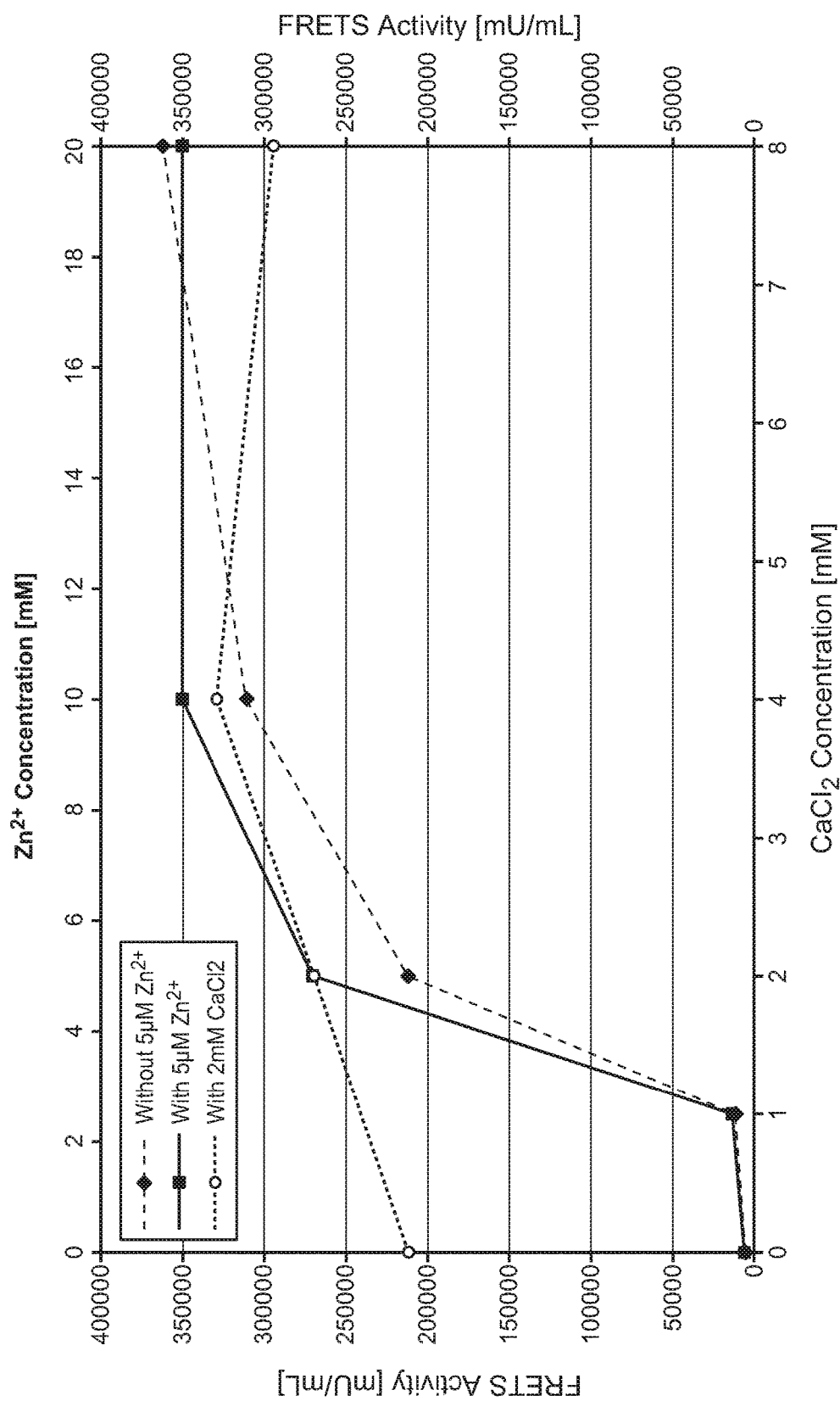

FIG. 34. Influence of calcium and zinc on the FRETS activity of recombinant human ADAMTS13.

Figure 35:
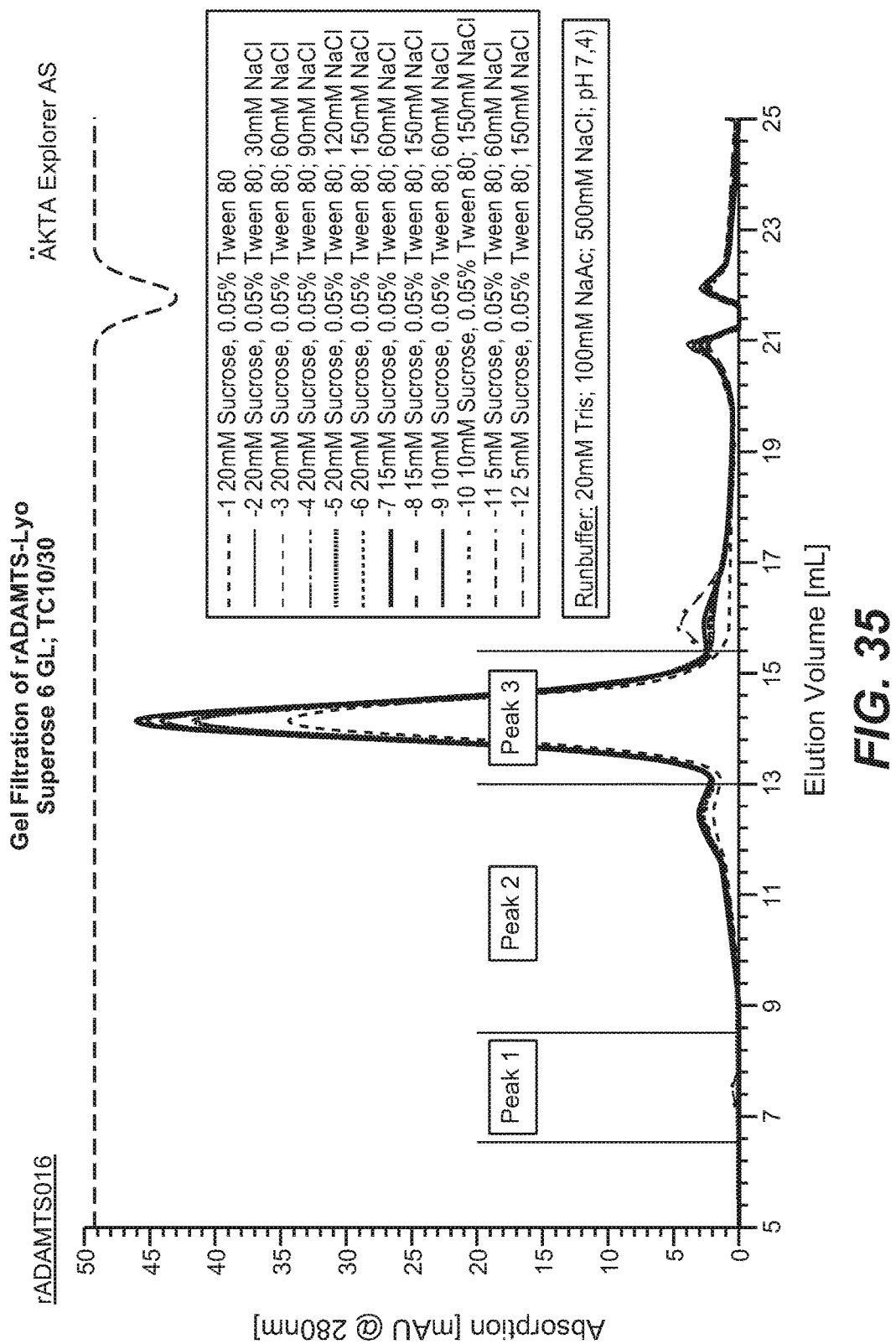

FIG. 35. Influence of salt and sugar content on the oligomeric state of lyophilized recombinant human ADAMTS13 formulation as determined by SE-HPLC. The sugar content of each formulation should be reported in g/L, rather than molar concentrations (e.g., 20 mM=20 g/L).

Figure 36:
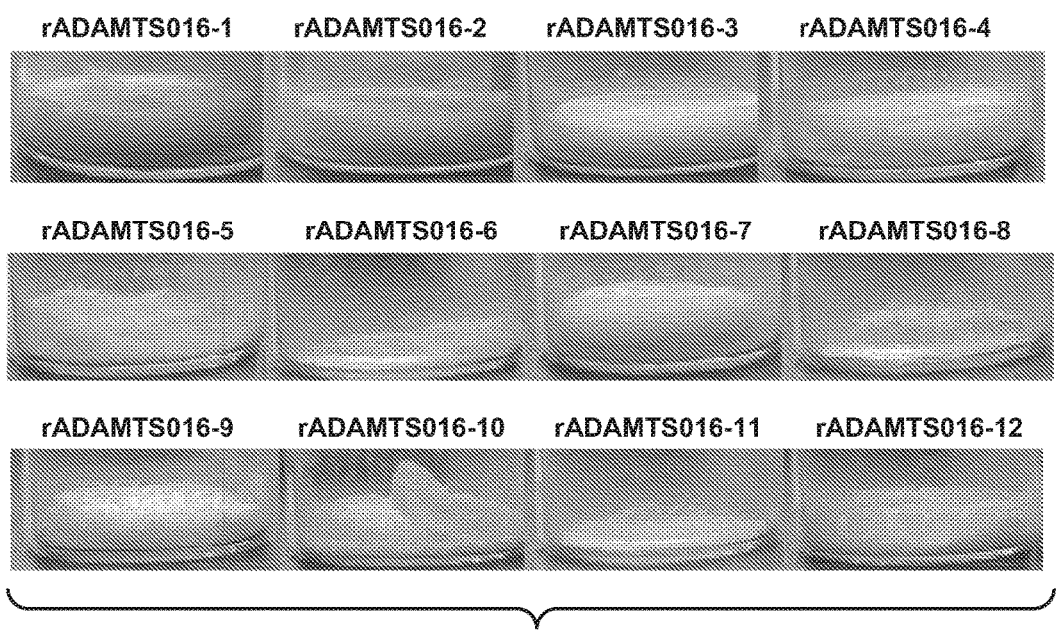

FIG. 36. Lyocakes produced by lyophilization of recombinant human ADAMTS13 formulated according to Table 15.

Figure 37B:
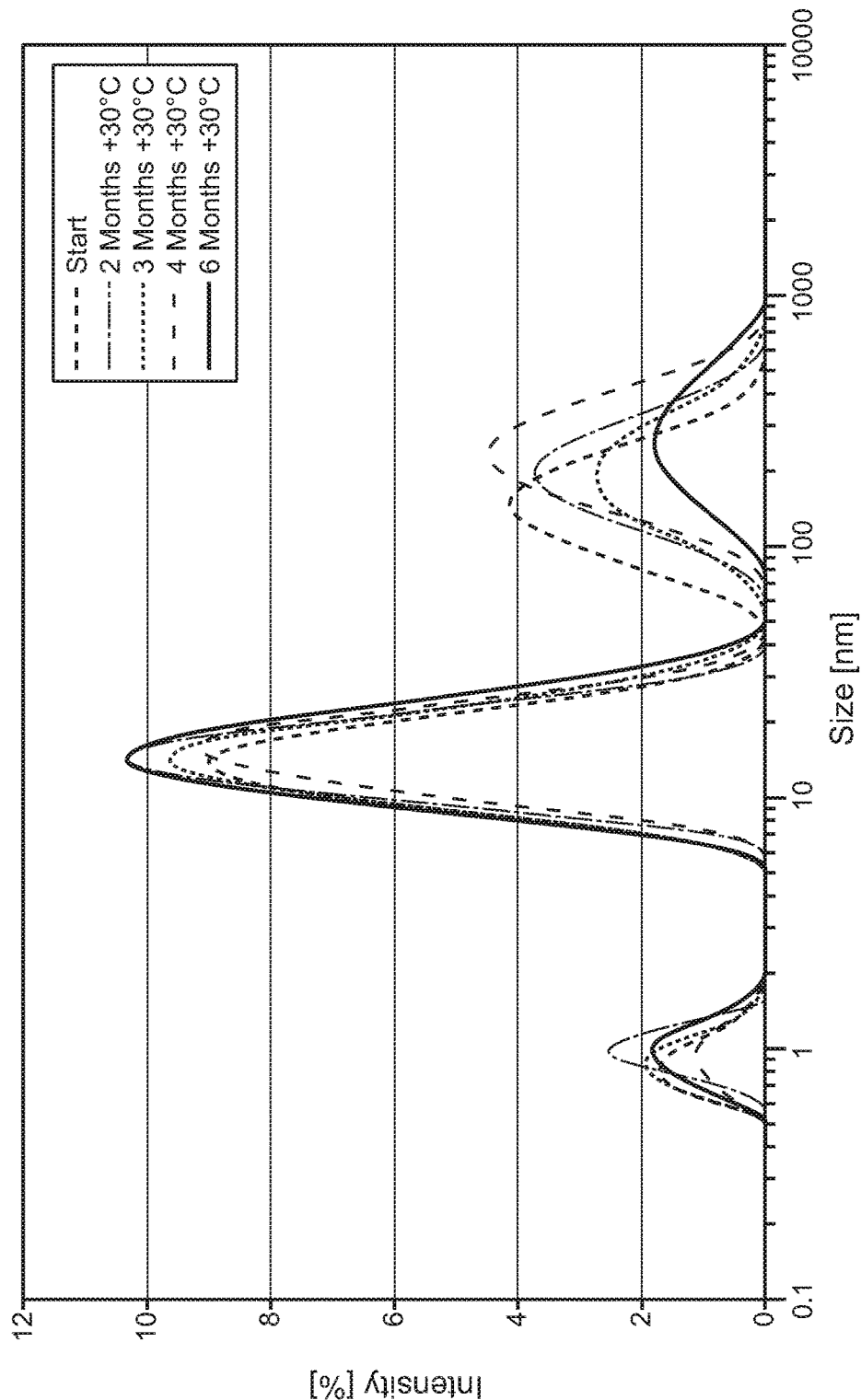
Figure 37C:
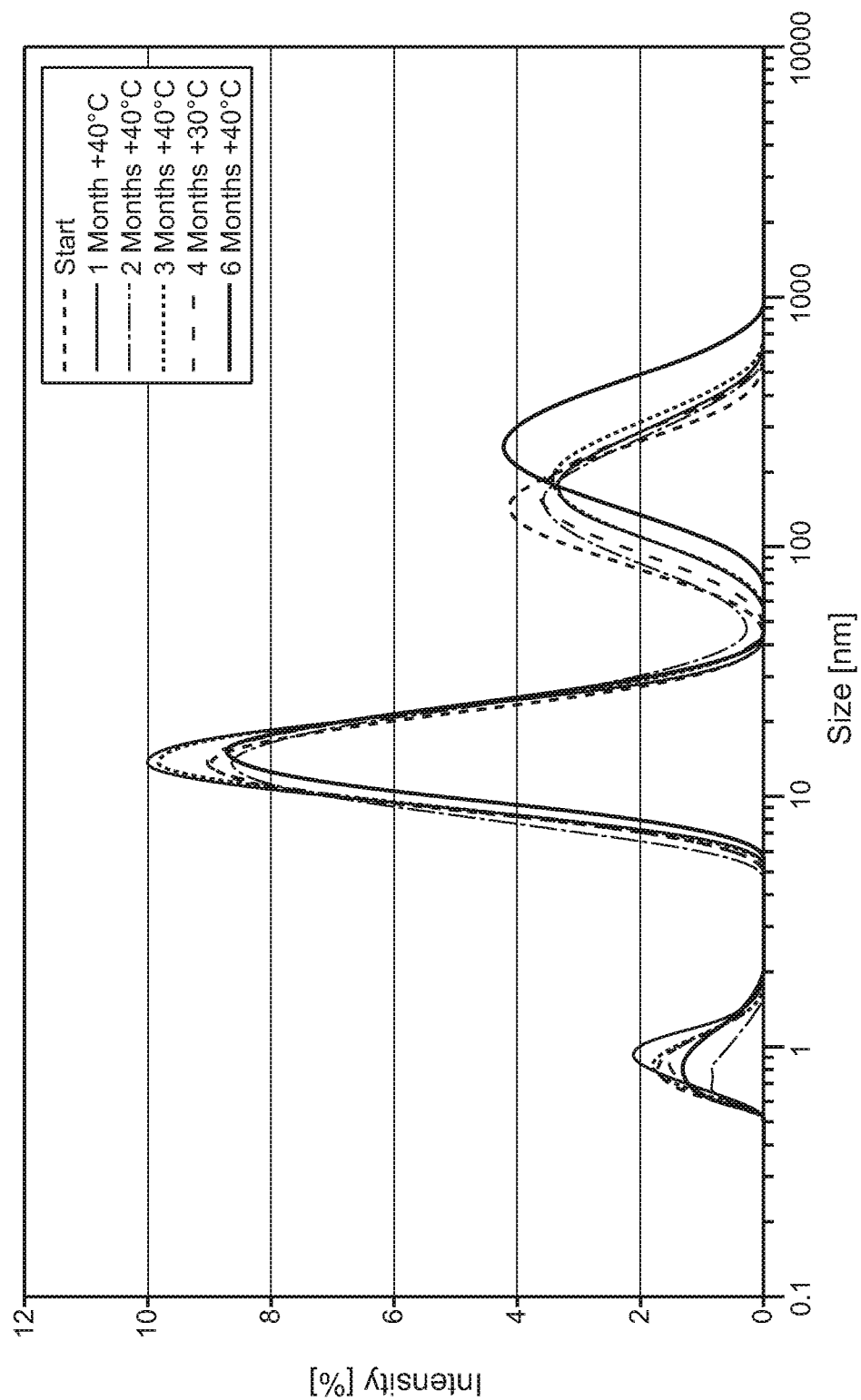

FIGS. 37A-37C. Dynamic light scattering (DLS) analysis of the oligomeric state of recombinant human ADAMTS13 lyophilized with a standard 3 day lyophilization program, stored for 6 months at (Top Panel) 4° C.; (Middle Panel) 30° C.; and (Bottom Panel) 40° C.

Figure 38A:
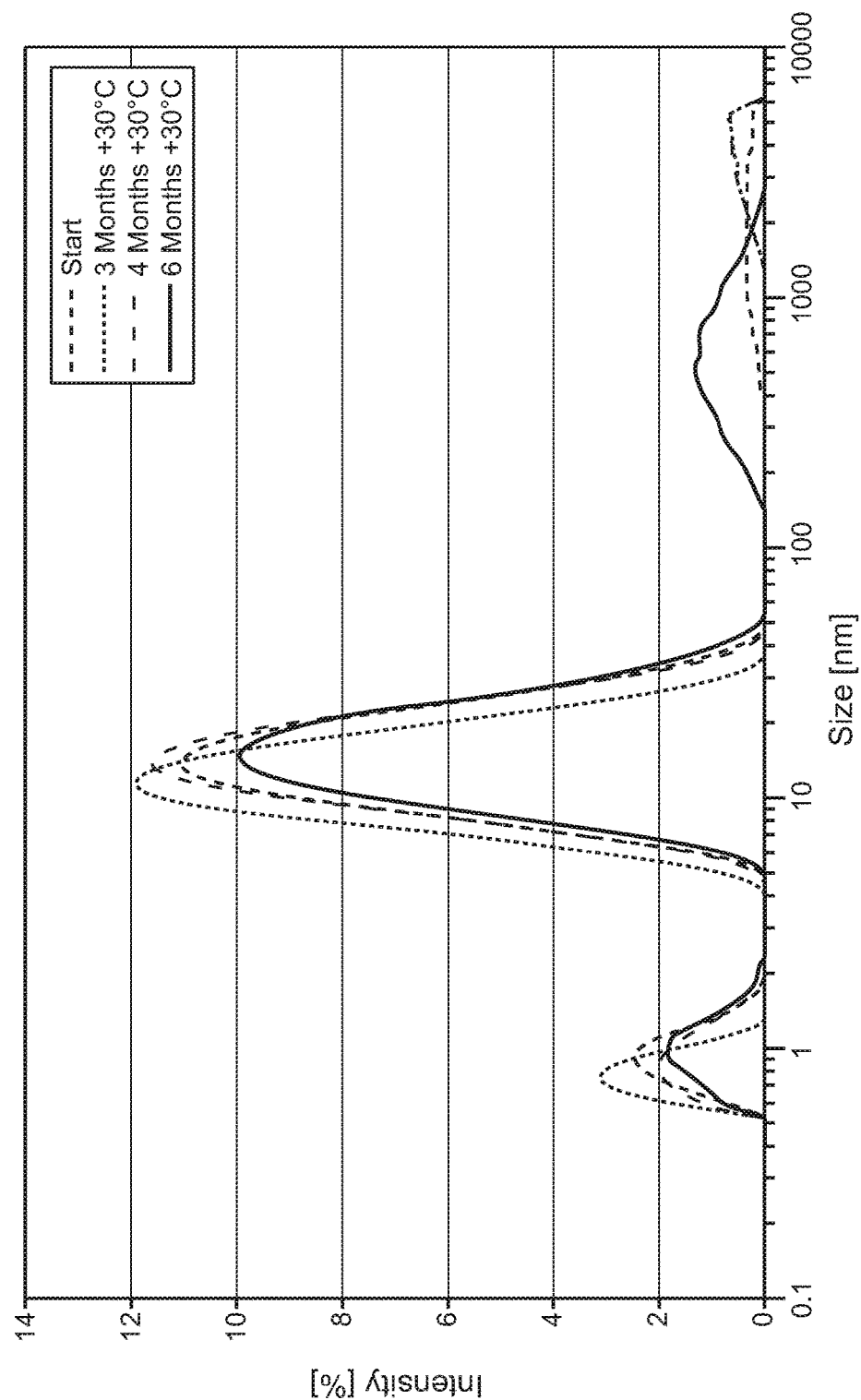
Figure 38B:
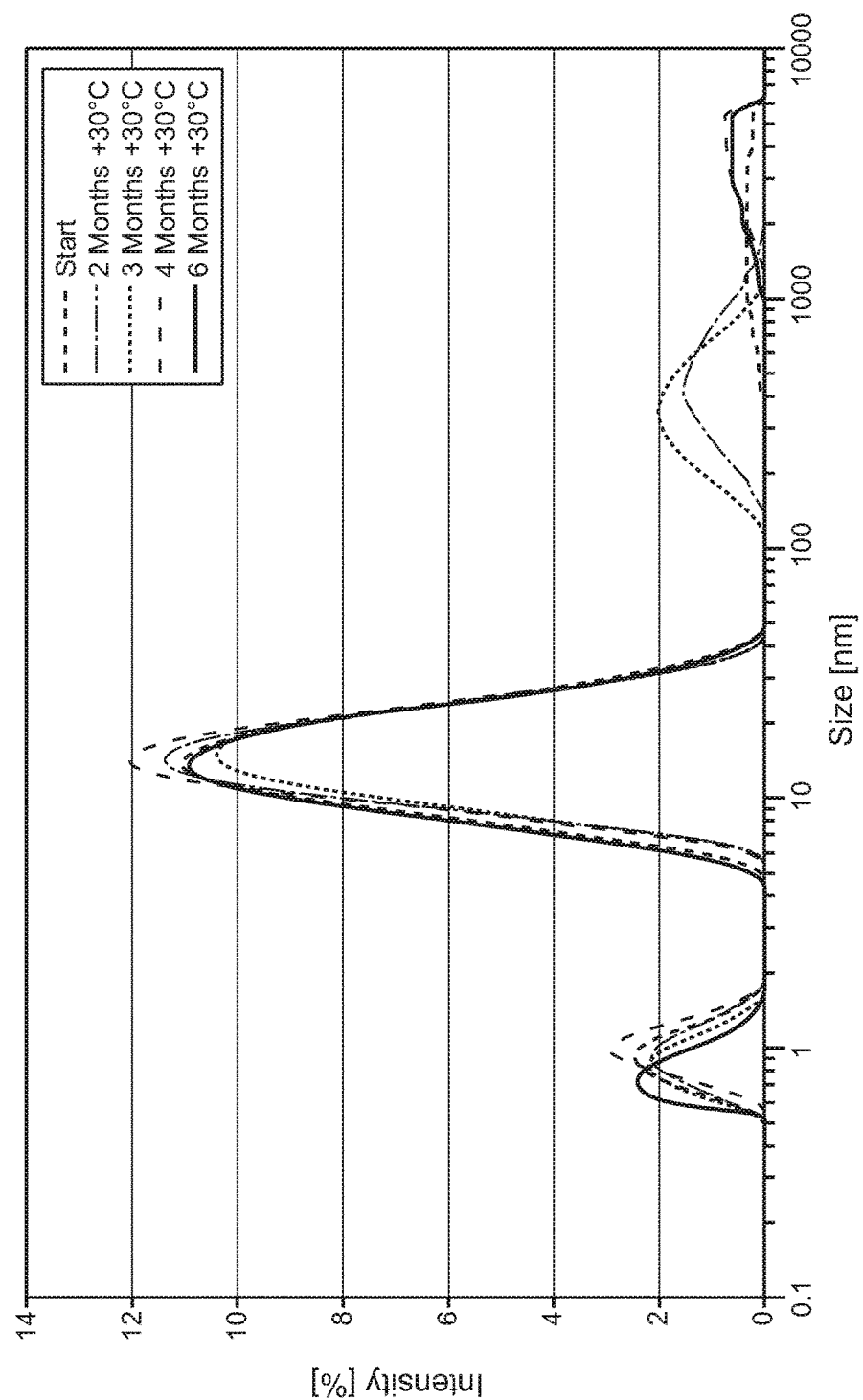
Figure 38C:
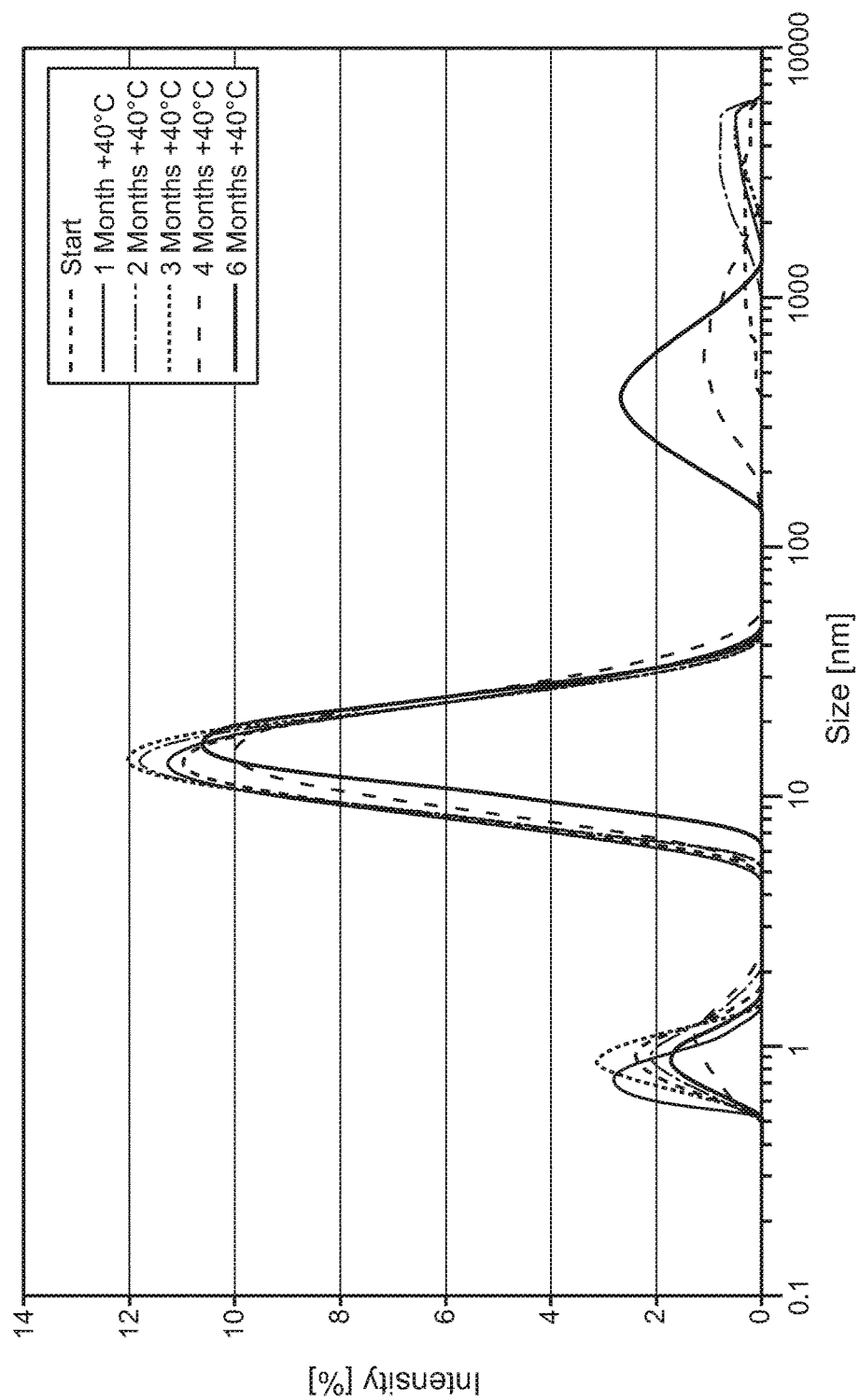

FIGS. 38A-38C. Dynamic light scattering (DLS) analysis of the oligomeric state of recombinant human ADAMTS13 lyophilized with an extended 10 day lyophilization program, stored for 6 months at (Top Panel) 4° C.; (Middle Panel) 30° C.; and (Bottom Panel) 40° C.

Figure 39:
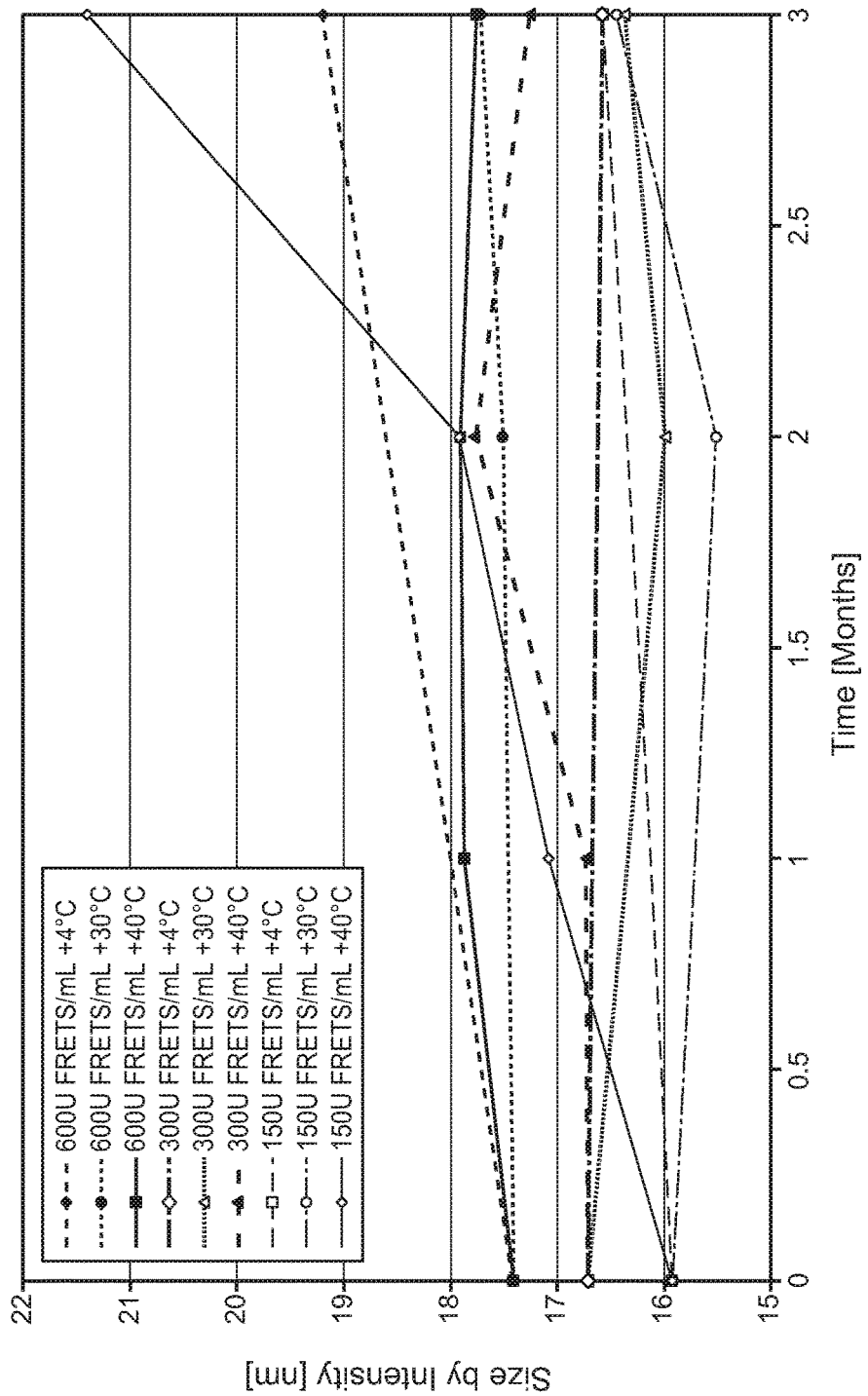

FIG. 39. Dynamic light scattering (DLS) analysis of the oligomeric state of recombinant human ADAMTS13 formulated at different protein concentrations after storage at 4° C., 30° C., and 40° C.

DETAILED DESCRIPTION OF THE INVENTION

I. Introduction

ADAMTS13 is a plasma metalloprotease which cleaves von Willebrand factor (VWF) mulitmers and down regulates their activity in platelet aggregation. Thrombotic thrombocytopenic purpura (TTP) is a severe disease associated with unusually large, hemostatically hyperactive von Willebrand factor (VWF) and severe deficiency in ADAMTS-13. A recombinant ADAMTS13 product candidate has been developed as a recombinant protein substitution therapy for the treatment of ADAMTS13 deficiency caused TTP (Plaimauer and Scheiflinger, Semin Hematol. 2004 January; 41(1):24-33; Plaimauer B et al., F. Blood. 2002 Nov. 15; 100(10): 3626-32. Epub 2002 Jul. 12; and Bruno K et al., J Thromb Haemost. 2005 May; 3(5):1064-73, the disclosures of which are all expressly incorporated by reference herein in their entireties for all purposes.)

The present invention is based in part on the discovery of liquid and lyophilized formulations of purified ADAMTS proteins with increased stability that meet the requirements set forth by the International Conference on Harmonisation of Technical Requirements of Pharmaceuticals for Human Use (ICH Guideline, PHARMACEUTICAL DEVELOPMENT Q8(R2), 2005).

The hemostatic activity of VWF is highly dependent on the size of the multimers. The plasma metalloprotease ADAMTS13 is the main protease identified that physiologically regulates the mulitmeric size of VWF. ADAMTS13 cleaves between Tyr 1605 and Met 1606 in the A2 domain of VWF yielding the typical cleavage fragments of 176 kDa and 140 kDa and smaller VWF multimers found in the circulation. The human ADAMTS13 gene contains 29 exons and spans approximately 37 kb on chromosome 9q34. The 4.7 kb transcript is predominantly synthesized in hepatic stellate cells, but also in vascular endothelial cells and platelets and encodes a primary translation product of 1427 amino acid residues. The precursor ADAMTS13 polypeptide consists of a signal peptide and a propeptide that C-terminally ends in a potential furin site for cleavage, followed by the sequence of the mature VWF-cleaving protease. The mature ADAMTS13 polypeptide (1353 amino acid residues) comprises the structural features characteristic of all ADAMTS family members: a reprolysin-like metalloprotease domain, a disintegrin-like domain, a central thrombospondin type 1 (TSP1) repeat, a cysteine-rich domain harboring a RGD motif possibly important for integrin interactions, and a spacer domain, thereafter followed by an unique combination of 7 consecutive TSP1 repeats (TSP1/#2-8) and two CUB domains (FIG. 26).

The mature ADAMTS13 has a calculated molecular mass of about 145 kDa whereas purified plasma-derived ADAMTS13 has an apparent molecular mass of about 180 kDa probably due to post-translational modifications consisting with present consensus sequences for 10 potential N-glycosylation sites, and several O-glycosylation sites and one C-mannosylation site in the TSP1 repeats. The VWF-proteolytic activity of ADAMTS13 is highly dependent on divalent cations. The active site motif in the metalloprotease domain contains the highly conserved HEXXHXXGXXHD motif with three histidine residues that coordinate a catalytic $Zn^{2+}$ ion and a predicted Calcium binding site proposed to be coordinated by Glu 83, Asp 173, Cys 281 and Asp 284. The functional roles of the ADAMTS13 domains have been studied mainly using in vitro assay systems, showing that the N-terminal regions from the metalloprotease to the spacer domain are crucial for VWF-cleavage. C-terminal TSP1 repeats and the CUB domains seem to be important for VWF substrate recognition and binding to potential surface receptors like CD36 on endothelial cells.

One major output of protein formulation development is the identification of inactivation pathways and aggregation or degradation pathways of the respective protein. Complete time-dependent inactivation of recombinant human ADAMTS13 protein within 1 week was observed at 40° C. in liquid formulation by FRETS activity assay. As disclosed herein, it was found that this inactivation could be reduced in the presence of 2 mM $Ca^{2+}$. At 25° C., FRETS activity did not decrease anymore in the presence of $Ca^{2+}$. At 4° C., liquid formulations of ADAMTS13 activity were stable for 24 weeks in the absence of $Ca^{2+}$.

Further, it was found that in identical lyophilized formulations that only slight or no inactivation occurred when the formulation was stored at 40° C. in the absence of $Ca^{2+}$. The addition of 2 mM or 4 mM $Ca^{2+}$ did not influence stability at 40° C.

Accordingly, the inventors have found that time-dependent aggregation of ADAMTS13 proteins in liquid formulation (e.g., stored at 40° C.) is a major contributor to the degradation and/or loss of enzymatic activity. Importantly, as provided by the present invention, this aggregation can be substantially reduced by lyophilization and/or by the addition of $Ca^{2+}$ to liquid formulations. Additionally, it has been found that the addition of a non-ionic surfactant (e.g., 0.05% Tween 80) reduces the formation of ADAMTS13 aggregates in lyophilized formulations. Furthermore, it was found that the presence of one or more sugars and/or sugar alcohols significantly stabilized ADAMTS13 during lyophilization and assists in the formation of an improved lyocake.

II. Definitions

As used herein, "ADAMTS13" or "A13" refer to a metalloprotease of the ADAMTS (a disintegrin and metalloproteinase with thrombospondin type I motifs) family that cleaves von Willebrand factor (vWF) between residues Tyr 1605 and Met 1606. In the context of the present invention, an ADAMTS13 protein embraces any ADAMTS13 protein, for example, ADAMTS13 from a mammal such as a primate, human (NP_620594), monkey, rabbit, pig, bovine (XP_610784), rodent, mouse (NP_001001322), rat (XP_342396), hamster, gerbil, canine, feline, frog (NP_001083331), chicken (XP_415435), and biologically active derivatives thereof. Mutant and variant ADAMTS13 proteins having activity are also embraced, as are functional fragments and fusion proteins of the ADAMTS13 proteins. Furthermore, the ADAMTS13 proteins of the invention may further comprise tags that facilitate purification, detection, or both. The ADAMTS13 proteins described herein may further be modified with a therapeutic moiety or a moiety suitable imaging in vitro or in vivo.

Human ADAMTS13 proteins include, without limitation, polypeptides comprising the amino acid sequence of GenBank accession number NP_620594 or a processed polypeptide thereof, for example a polypeptide in which the signal peptide (amino acids 1 to 29) and/or propeptide (amino acids 30-74) have been removed. Many natural variants of human ADAMTS13 are known in the art, and are embraced by the formulations of the present invention, some of which include mutations selected from R7W, V88M, H96D, R102C, R193W, T196I, H234Q, A250V, R268P, W390C, R398H, Q448E, Q456H, P457L, P475S, C508Y, R528G, P618A, R625H, I673F, R692C, A732V, E740K, A900V, S903L, C908Y, C951G, G982R, C1024G, A1033T, R1095W, R1095W, R1123C, C1213Y, T1226I, G1239V, and R1336W. Additionally, ADAMTS13 proteins include natural and recombinant proteins that have been mutated, for example, by one or more conservative mutations at a non-essential amino acid. Preferably, amino acids essential to the enzymatic activity of ADAMTS13 will not be mutated. These include, for example, residues known or presumed to be essential for metal binding such as residues 83, 173, 224, 228, 234, 281, and 284, and residues found in the active site of the enzyme, e.g., residue 225. Similarly, in the context of the present invention, ADAMTS13 proteins include alternate isoforms, for example, isoforms lacking amino acids 275 to 305 and/or 1135 to 1190 of the full-length human protein.

As used herein, the term "biologically active derivative" refers to any polypeptide with substantially the same biological function as ADAMTS13. The polypeptide sequences of the biologically active derivatives may comprise deletions, additions and/or substitution of one or more amino acids whose absence, presence and/or substitution, respectively, do not have any substantial negative impact on the biological activity of polypeptide. The biological activity of said polypeptides may be measured, for example, by the reduction or delay of platelet adhesion to the endothelium, the reduction or delay of platelet aggregation, the reduction or delay of the formation of platelet strings, the reduction or delay of thrombus formation, the reduction or delay of thrombus growth, the reduction or delay of vessel occlusion, the proteolytic cleavage of vWF, the disintegration of thrombi, or by cleavage of a peptide substrate, for example a FRETS-VWF73 peptide (Kokame et al., Br J Haematol. 2005 April; 129(1):93-100) or variant thereof.

Likewise, ADAMTS13 proteins may be further modified, for example, by post-translational modifications (e.g., glycosylation at one or more amino acids selected from human residues 142, 146, 552, 579, 614, 667, 707, 828, 1235, 1354, or any other natural or engineered modification site) or by ex vivo chemical or enzymatic modification, including without limitation, glycosylation, modification by water soluble polymer (e.g., PEGylation, sialylation, HESylation, etc.), tagging, and the like.

As used herein, "one unit of ADAMTS13 activity" is defined as the amount of activity in 1 ml of pooled normal human plasma, regardless of the assay being used. For example, one unit of ADAMTS13 FRETS-VWF73 activity is the amount of activity needed to cleave the same amount of FRETS-VWF73 substrate (Kokame et al., Br J Haematol. 2005 April; 129(1):93-100) as is cleaved by one ml of pooled normal human plasma.

As used herein, the terms "ADAMTS13" and "biologically active derivative", respectively, also include polypeptides obtained via recombinant DNA technology. The recombinant ADAMTS13 ("rADAMTS13"), e.g. recombinant human ADAMTS13 ("r-hu-ADAMTS13"), may be produced by any method known in the art. One specific example is disclosed in WO 02/42441 which is incorporated herein by reference with respect to the method of producing recombinant ADAMTS13. This may include any method known in the art for (i) the production of recombinant DNA by genetic engineering, e.g. via reverse transcription of RNA and/or amplification of DNA, (ii) introducing recombinant DNA into prokaryotic or eukaryotic cells by transfection, i.e. via electroporation or microinjection, (iii) cultivating said transformed cells, e.g. in a continuous or batchwise manner, (iv) expressing ADAMTS13, e.g. constitutively or upon induction, and (v) isolating said ADAMTS13, e.g. from the culture medium or by harvesting the transformed cells, in order to (vi) obtain substantially purified recombinant ADAMTS13, e.g. via anion exchange chromatography or affinity chromatography. The term "biologically active derivative" includes also chimeric molecules such as, e.g. ADAMTS13 (or a biologically active derivative thereof) in combination with Ig, in order to improve the biological/pharmacological properties such as, e.g. half life of ADAMTS13 in the circulation system of a mammal, particularly human. The Ig could have also the site of binding to an optionally mutated Fc receptor.

As used herein, the term "thrombus" refers to a blood clot, especially a platelet-comprising blood clot, a microthrombus, and/or an embolus. Said thrombus may be attached to an arterial or venous blood vessel or not, and may partially or completely block the blood flow in an arterial or venous blood vessel.

As used herein, the terms "vitamin B3", "nicotinamide", "niacinamide", "niacin", and "nicotinic acid" may be used interchangeably to refer to any member of the B3 family of vitamins.

As used herein, a "therapeutically effective amount or dose" or "sufficient amount or dose" refers to a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, a "physiological concentration" of salt refers to a salt concentration of between about 100 mM and about 200 mM of a pharmaceutically acceptable salt. Non-limiting examples of pharmaceutically acceptable salts include, without limitation, sodium and potassium chloride, sodium and potassium acetate, sodium and potassium citrate, sodium and potassium phosphate.

As used herein, a "sub-physiological concentration" of salt refers to a salt concentration of less than about 100 mM of a pharmaceutically acceptable salt. In preferred embodiments, a sub-physiological concentration of salt is less than about 80 mM of a pharmaceutical salt. In another preferred embodiment, a sub-physiological concentration of salt is less than about 60 mM of a pharmaceutical salt.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%."

As used herein, "storage" means that a formulation is not immediately administered to a subject once prepared, but is kept for a period of time under particular conditions (e.g., particular temperature, etc.) prior to use. For example, a liquid or lyophilized formulation can be kept for days, weeks, months or years, prior to administration to a subject under varied temperatures such as refrigerated (0° to 10° C.) or room temperature (e.g., temperature up to 32° C.).

As used herein, the term "chemically defined medium" refers to a synthetic growth medium in which the identity and concentration of all the components are known. Chemically defined mediums do not contain bacterial, yeast, animal, or plant extracts, although they may or may not include individual plant or animal-derived components (e.g., proteins, polypeptides, etc.). Non-limiting examples of commercially available chemically defined mediums include, various EX-CELL® mediums (SAFC Biosciences, Inc), various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), and the like. Methods of preparing chemically defined culture mediums are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "oligopeptide-free culture medium" refers to a protein-free medium that does not comprise oligopeptides, such as, e.g., oligopeptides derived from a protein hydrolysate. In one embodiment, the medium does not comprise oligopeptides having twenty or more amino acids. In one embodiment of the present invention, the medium does not comprise oligopeptides having fifteen or more amino acids. In another embodiment of the invention, the medium does not comprise oligopeptides having ten or more amino acids. In one embodiment the medium does not comprise oligopeptides having seven or more amino acids. In another embodiment the medium does not comprise oligopeptides having five or more amino acids. In still another embodiment the medium does not comprise oligopeptides having three or more amino acids. According to a further embodiment of the present invention, the medium does not comprise oligopeptides having two or more amino acids. Methods of preparing oligopeptide-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "serum-free culture medium" refers to a culture medium that is not supplemented with an animal serum. Although oftentimes serum-free mediums are chemically defined mediums, serum-free mediums may be supplemented with discrete animal or plant proteins or protein fractions. Methods of preparing serum-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "animal protein-free culture medium" refers to a culture medium that is not supplemented with an animal serum, protein, or protein fraction. Although oftentimes animal protein-free culture mediums are chemically defined mediums, animal protein-free culture mediums may contain plant or yeast hydrolysates. Methods of preparing animal protein-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

III. ADAMTS13 Compositions and Formulation

In one aspect, the present invention provides stabilized formulations of ADAMTS13 (A13) and rADAMTS13 (rA13) proteins. In one embodiment, the formulations of the invention are stable when stored at temperatures up to at least about 40° C. for at least about 6 months. In other embodiments, the formulations provided herein retain significant ADAMTS13 activity when stored for extended periods of time. In yet other embodiments, the formulations of the invention reduce or retard dimerization, oligomerization, and/or aggregation of an ADAMTS13 protein.

In one embodiment, the present invention provides formulations of ADAMTS13 comprising a therapeutically effective amount or dose of an ADAMTS13 protein, a sub-physiological to physiological concentration of a pharmaceutically acceptable salt, a stabilizing concentration of one or more sugars and/or sugar alcohols, a non-ionic surfactant, a buffering agent providing a neutral pH to the formulation, and optionally a calcium and/or zinc salt. Generally, the stabilized A13 formulations provided herein are suitable for pharmaceutical administration. In a preferred embodiment, the A13 protein is human ADAMTS13 or a biologically active derivative or fragment thereof.

In certain embodiments, the ADAMTS13 formulations are liquid formulations. In other embodiments, the ADAMTS13 formulations are lyophilized formulations that are lyophilized from a liquid formulation as provided herein.

In certain embodiments of the formulations provided herein, the ADAMTS13 protein is a human ADAMTS13 (hA13) or recombinant human ADAMTS13 (rhA13), or a biologically active derivative or fragment thereof. In one embodiment, the amino acid sequence of hA13 is that of GenBank accession number NP_620594. In another embodiment, the amino acid sequence of hA13 comprises amino acids 75 to 1427 of NP_620594, a natural or conservative variant thereof, or a biologically active fragment thereof.

In certain embodiments, ADAMTS13 is provided in a therapeutically effective dose between about 0.05 mg/mL and about 10 mg/mL. In other embodiments, ADAMTS13 is present at a concentration of between about 0.1 mg/mL and about 10 mg/mL. In yet other embodiments, ADAMTS13 is present at a concentration of between about 0.1 mg/mL and about 5 mg/mL. In another embodiment, ADAMTS13 is present at a concentration of between about 0.1 mg/mL and about 2 mg/mL. In yet other embodiments, ADAMTS13 may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In one embodiment, the concentration of a relatively pure ADAMTS13 formulation may be determined by spectroscopy (i.e., total protein measured at $A_{280}$) or other bulk determination (e.g., Bradford assay, silver stain, weight of a lyophilized powder, etc.). In other embodiments, the concentration of ADAMTS13 may be determined by an ADAMTS13 ELISA assay (e.g., mg/mL antigen).

In yet other embodiments, the concentration of ADAMTS13 in a formulation provided by the present invention may be expressed as a level of enzymatic activity. For example, in one embodiment an ADAMTS13 formulation may contain between about 10 units of FRETS-VWF73 activity and about 10,000 units of FRETS-VWF73 activity or other suitable A13 enzymatic unit (IU). In other embodiments, the formulation may contain between about 20 units of FRETS-VWF73 ($U_{FV73}$) activity and about 8,000 units of FRETS-VWF73 activity, or between about 30 $U_{FV73}$ and about 6,000 $U_{FV73}$, or between about 40 $U_{FV73}$ and about 4,000 $U_{FV73}$, or between about 50 $U_{FV73}$ and about 3,000 $U_{FV73}$, or between about 75 $U_{FV73}$ and about 2,500 $U_{FV73}$, or between about 100 $U_{FV73}$ and about 2,000 $U_{FV73}$, or between about 200 $U_{FV73}$ and about 1,500 $U_{FV73}$, or between about other ranges therein. In a preferred embodiment, an ADAMTS13 formulation provided herein contains between about 150 and about 600 $U_{FV73}$. In certain embodiments, a formulation contains about 10 units of FRETS-VWF73 activity, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more units of FRETS-VWF73 activity.

Similarly, in certain embodiments, the concentration of ADAMTS13 may be expressed as an enzymatic activity per unit volume, for example, A13 enzymatic units per mL (IU/mL). For example, in one embodiment an ADAMTS13 formulation may contain between about 10 IU/mL and about 10,000 IU/mL. In other embodiments, the formulation may contain between about 20 IU/mL and about 8,000 IU/mL, or between about 30 IU/mL and about 6,000 IU/mL, or between about 40 IU/mL and about 4,000 IU/mL, or between about 50 IU/mL and about 3,000 IU/mL, or between about 75 IU/mL and about 2,500 IU/mL, or between about 100 IU/mL and about 2,000 IU/mL, or between about 200 IU/mL and about 1,500 IU/mL, or between about other ranges therein. In a preferred embodiment, an ADAMTS13 formulation provided herein contains between about 150 IU/mL and about 600 IU/mL. In another preferred embodiment, an ADAMTS13 formulation provided herein contains between about 100 IU/mL and about 1,000 IU/mL. In certain embodiments, a formulation contains about 10 IU/mL, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more IU/mL.

In certain embodiments, the stabilized ADAMTS13 formulations provided by the present invention will contain a sub-physiological to physiological salt concentration, for example, between and 0 mM and about 200 mM of a pharmaceutically acceptable salt. In one embodiment, an ADAMTS13 formulation will contain a physiological concentration of salt, for example, between about 100 mM and about 200 mM of a pharmaceutically acceptable salt. In other embodiments, an ADAMTS13 formulation will contain about 0 mM, or about 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, or more of a pharmaceutically acceptable salt. In a preferred embodiment, the salt is sodium or potassium chloride.

Advantageously, it has been found that ADAMTS13 formulations containing a sub-physiological concentration of a pharmaceutically acceptable salt form compact lyocakes with smooth surfaces. Furthermore, it has been found that low salt lyophilized formulations of ADAMTS13 proteins reduce protein aggregation as compared to formulations prepared with physiological concentrations of salt. Accordingly, in a preferred embodiment, the present invention provides low salt formulations of ADAMTS13 containing a sub-physiological concentration of a pharmaceutically acceptable salt, for example, less than about 100 mM of a pharmaceutically acceptable salt. In one embodiment, a low salt ADAMTS13 formulation provided herein contains less than about 100 mM of a pharmaceutical salt. In a preferred embodiment, a low salt ADAMTS13 formulation provided herein contains less than about 80 mM of a pharmaceutical salt. In another preferred embodiment, a low salt ADAMTS13 formulation provided herein contains less than about 60 mM of a pharmaceutical salt (i.e., between about 0 mM and about 60 mM salt). In another preferred embodiment, a low salt ADAMTS13 formulation will contain between about 30 mM and about 60 mM of a pharmaceutically acceptable salt. In yet other embodiments, a low salt ADAMTS13 formulation will contain about 0 mM, or about 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM of a pharmaceutically acceptable salt. In a preferred embodiment, a low salt ADAMTS13 formulation is a lyophilized formulation. In a preferred embodiment, the salt is sodium or potassium chloride.

It has also been found that the inclusion of moderate levels (i.e., between about 2% and about 6%) of one or more sugars and/or sugar alcohols assists in the preparation of compact lyocakes with smooth surfaces and helps to stabilize ADAMTS13 upon lyophilization. Accordingly, in one embodiment, the present invention provides ADAMTS13 formulations containing between about 2% and about 6% of one or more sugars and/or sugar alcohols. Any sugar such as mono-, di-, or polysaccharides, or water-soluble glucans, including for example fructose, glucose, mannose, sorbose, xylose, maltose, lactose, sucrose, dextran, trehalose, pullulan, dextrin, cyclodextrin, soluble starch, hydroxyethyl starch, and carboxymethylcellulose may be used. In a particular embodiment, sucrose or trehalose is used as a sugar additive. Sugar alcohols are defined as a hydrocarbon having between about 4 and about 8 carbon atoms and a hydroxyl group. Non-limiting examples of sugar alcohols that may be used in the ADAMTS13 formulations provided herein include, mannitol, sorbitol, inositol, galactitol, dulcitol, xylitol, and arabitol. In one embodiment, mannitol is used as a sugar alcohol additive. In a preferred embodiment, an ADAMTS13 formulation contains both a sugar and a sugar alcohol additive.

The sugars and sugar alcohols may be used individually or in combination. In some embodiments, the sugar, sugar alcohol, or combination thereof will be present in the formulation at a concentration of between about 0.5% and about 7%. In one embodiment, the sugar and/or sugar alcohol content of the formulation will be between about 0.5% and about 5%. In certain embodiments, the sugar, sugar alcohol, or combination thereof will be present at a concentration of between about 1% and about 5%. In a preferred embodiment, the sugar, sugar alcohol, or combination thereof will be present at a concentration of between about 2% and about 6%. In another preferred embodiment, the sugar, sugar alcohol, or combination thereof will be present at a concentration of between about 3% and about 5%. In certain embodiments, the final concentration may be about 0.5%, 1%, 1.5%, 2%, 2.5%, 3%, 3.5%, 4%, 4.5%, 5%, 5.5%, 6.0%, 6.5%, or 7.0% sugar, sugar alcohol, or combination thereof. In particular embodiments, a formulation provided herein may comprise a sugar at a concentration from about 0.5% to about 5.0% and a sugar alcohol at a concentration from about 0.5% to about 5.0%. Any combination of sugar and sugar alcohol concentrations may be used, e.g. a sugar present at a concentration of about 0.5%, 1%, 1.5%, 2%, 2.5%, 3%, 3.5%, 4%, 4.5%, 5%, 5.5%, 6.0%, 6.5%, or 7.0% and a sugar alcohol present at a concentration of about 0.5%, 1%, 1.5%, 2%, 2.5%, 3%, 3.5%, 4%, 4.5%, 5%, 5.5%, 6.0%, 6.5%, or 7.0%.

Advantageously, it was also found that the inclusion of a non-ionic surfactant substantially reduces the aggregation of ADAMTS13 formulations. Accordingly, in one embodiment, ADAMTS13 formulations containing a stabilizing concentration of a non-ionic detergent are provided. Pharmaceutically acceptable nonionic surfactants that may be used in the formulations of the present invention are known in the art of pharmaceutical science, and include, without limitation, Polysorbate 80 (Tween 80), Polysorbate 20 (Tween 20), and various poloxamers or pluronics, including Pluronic F-68, and BRIJ 35, or mixtures thereof. In a preferred embodiment, the nonionic surfactant used in the present pharmaceutical formulations is Polysorbate 80. In certain embodiments, a surfactant may be used in a formulation provided herein at a concentration between about 0.001% and about 0.2%. In a preferred embodiment, the surfactant is used at a concentration of between about 0.01% and about 0.1%. In another preferred embodiment, the surfactant is used at a concentration of about 0.05%. For example, in certain embodiments, the formulation may include a nonionic surfactant at a concentration of about 0.001%, 0.005%, 0.01%, 0.02%, 0.03%, 0.04%, 0.05%, 0.06%, 0.07%, 0.08%, 0.09%, 0.1%, 0.125%, 0.15%, 0.175%, 0.2%, and the like.

Furthermore, it was found that ADAMTS13 formulations were stabilized when formulated at a neutral pH between about 6.5 and about 7.5. Accordingly, in certain embodiments, ADAMTS13 formulations are provided that contain a buffering agent suitable to maintain the formulation at a neutral pH. Pharmaceutically acceptable buffering agents are well known in the art, and include without limitation, phosphate buffers, histidine, sodium citrate, HEPES, Tris, Bicine, glycine, N-glycylglycine, sodium acetate, sodium carbonate, glycylglycine, lysine, arginine, sodium phosphate, and mixtures thereof. In preferred embodiments, the buffer is selected from histidine, phosphate buffer, HEPES, and sodium citrate. In one preferred embodiment, the buffer is histidine or HEPES. In a specific embodiment, the buffer in histidine. In another specific embodiment, the buffer is HEPES. In one embodiment, the pH of the formulations provided herein is between about 6.5 and about 9.0. In certain embodiments, the pH of the formulation is about 6.5 or about 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In a preferred embodiment, the pH of the A13 formulation is between about 6.0 and about 8.0. In a more preferred embodiment, the pH of the A13 formulation is between about 6.5 and about 7.5. In a particular embodiment, the pH of the A13 formulation is about 7.0. In another particular embodiment, the pH of the A13 formulation is 7.0±0.2.

It is also demonstrated herein that the inclusion of calcium further stabilizes formulations of ADAMTS13. Accordingly, in certain embodiments, stabilized ADAMTS13 formulations are provided which contain between about 0.5 mM and about 20 mM calcium (e.g., calcium chloride). Any pharmaceutically acceptable calcium salt may be used in the formulations provided herein. Non-limiting examples of calcium salt that may be used include, for example, $CaCl_2$, $CaCO_3$, $Ca(C_6H_{11}O_7)_2$, $Ca_3(PO_4)_2$, $Ca(C_{18}H_{35}O_2)_2$, and the like. In one embodiment, calcium is present in an ADAMTS13 formulation of the invention at a concentration from about 0.5 mM to about 10 mM. In another embodiment, calcium is present in an ADAMTS13 formulation at a concentration between about 2 mM and about 5 mM. In a preferred embodiment, calcium is present in an ADAMTS13 formulation at a concentration from about 2 mM to about 4 mM. In certain embodiments, the concentration of calcium is about 0.5 mM, or about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM. In a particular embodiment, the concentration of calcium is about 2 mM. In another preferred embodiment, the concentration of calcium is about 3 mM. In yet another preferred embodiment, the concentration of calcium is about 4 mM.

Similarly, it has been found that under certain conditions, the inclusion of zinc further stabilizes an ADAMTS13 formulation as provided herein. For example, FIG. 34 shows that inclusion of between about 2 µM and about 10 µM zinc further stabilized calcium containing ADAMTS13 formulations. Any pharmaceutically acceptable zinc salt may be used in the formulations provided herein. Non-limiting examples of zinc salt that may be used include, for example, $ZnSO_4.7H_2O$, $ZnSO_3.2H_2O$, $Zn_3(PO_4)_2$, and $(C_6H_5O_7)_2 Zn_3.2H_2O$, and the like. In one embodiment, $ZnSO_4$ is used in the ADAMTS13 formulations provided herein. In some embodiments, zinc is present in an ADAMTS13 formulation of the invention at a concentration from about 0.5 µM to about 20.0 µM. In a preferred embodiment, zinc is included in an ADAMTS13 formulation at a concentration of between about 0.5 µM to about 10.0 µM. In certain embodiments, the concentration of zinc is about 0.5 µM, or about 1 µM, 2 µM, 3 µM, 4 µM, 5 µM, 6 µM, 7 µM, 8 µM, 9 µM, or 10 µM.

In some embodiments, the ADAMTS13 formulations provided herein may further comprise one or more pharmaceutically acceptable excipients, carriers, and/or diluents. In addition, the formulations provided herein may further comprise other medicinal agents, carriers, adjuvants, diluents, tissue permeation enhancers, solubilizers, and the like. Methods for preparing compositions and formulations for pharmaceutical administration are known to those skilled in the art (see, for example, *REMINGTON'S PHARMACEUTICAL SCIENCES,* 18TH ED., Mack Publishing Co., Easton, Pa. (1990)).

In one embodiment, the ADAMTS13 formulations provided herein will have a tonicity in a range between about 200 mOsmol/L and about 400 mOsmol/L, or in a range between about 250 and about 350 mOsmol/L. In certain embodiments, an ADAMTS13 formulation provided herein will have a tonicity, for example, of about 200 mOsmol/L, or of about 210 mOsmol/L, 220 mOsmol/L, 230 mOsmol/L, 240 mOsmol/L, 250 mOsmol/L, 260 mOsmol/L, 270 mOsmol/L, 280 mOsmol/L, 290 mOsmol/L, 300 mOsmol/L, 310 mOsmol/L, 320 mOsmol/L, 330 mOsmol/L, 340 mOsmol/L, 350 mOsmol/L, 360 mOsmol/L, 370 mOsmol/L, 380 mOsmol/L, 390 mOsmol/L, or 400 mOsmol/L.

Examples of tonicity agents that may be used in the formulations provided herein include, without limitation, sodium chloride, dextrose, sucrose, xylitol, fructose, glycerol, sorbitol, mannitol, trehalose, potassium chloride, mannose, calcium chloride, magnesium chloride, other inorganic salts, other sugars, other sugar alcohols, and combinations thereof. In certain embodiments, an ADAMTS13 formulation may comprise at least one tonicity agent, or at least two, three, four, five, or more tonicity agents.

The ADAMTS13 formulations provided herein may be formulated for administration via known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, the ADAMTS13 formulations provided herein can be administered either systemically or locally. Systemic administration includes, without limitation: oral, subdermal, intraperitioneal, subcutaneous, transnasal, sublingual, or rectal routes of administration. Local administration includes, without limitation: topical, subcutaneous, intramuscular, and intraperitoneal routes of administration.

In one aspect of the invention, a composition of monomeric ADAMTS13 protein is provided. In certain embodiments, the composition of monomeric ADAMTS13 protein is substantially free of aggregated ADAMTS13, dimeric ADAMTS13, or both aggregated and dimeric ADAMTS13. In some embodiments, the monomeric composition has a higher specific activity than a similar composition containing aggregated and/or dimeric ADAMTS13 protein. In a particular embodiment, the monomeric ADAMTS13 composition is produced by a method comprising gel filtration or size exclusion chromatography. In one particular embodiment, the ADAMTS13 protein is a human ADAMTS13 (hA13) or recombinant human ADAMTS13 (rhA13), or a biologically active derivative or fragment thereof.

In another aspect, formulations of monomeric ADAMTS13 compositions are provided. In one embodiment, the formulation is a pharmaceutically acceptable formulation of the monomeric ADAMTS13 protein. In certain embodiments, the formulation is substantially free of aggregated ADAMTS13, dimeric ADAMTS13, or both aggregated and dimeric ADAMTS13. In some embodiments, the monomeric ADAMTS13 formulations have a higher specific activity than similar formulations containing aggregated and/or dimeric ADAMTS13 protein. In a particular embodiment, the monomeric ADAMTS13 formulation is produced by a method comprising gel filtration or size exclusion chromatography. In one particular embodiment, the ADAMTS13 protein in the formulation is a human ADAMTS13 (hA13) or recombinant human ADAMTS13 (rhA13), or a biologically active derivative or fragment thereof. In certain embodiments, the monomeric ADAMTS13 protein is formulated according to a formulation provided herein.

In embodiment, the present invention provides formulations of ADAMTS13 comprising from about 0.0.5 mg/ml to about 10.0 mg/ml ADAMTS13 protein, from about 0 mM to about 200 mM of a pharmaceutically acceptable salt, a sugar and/or sugar alcohol, a non-ionic surfactant, and a buffering agent. In certain embodiments, the formulations may further comprise calcium and/or zinc. In other embodiments, the formulation may be buffered at a pH of between about 6.5 and 9.0. In certain embodiments, the A13 formulations are suitable for pharmaceutical administration.

In a specific embodiment, the present invention provides a stabilized formulation of ADAMTS13, comprising: 0.05 mg/ml to 10.0 mg/ml ADAMTS13; 0 mM to 200 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5. In a preferred embodiment, the pharmaceutically acceptable salt is sodium chloride or potassium chloride.

In one embodiment, a stabilized ADAMTS13 formulation is provided comprising 0.05 mg/ml to 10.0 mg/ml ADAMTS13; 0 mM to 200 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5 contains between about 50 units per mL and about 1000 units per mL of ADAMTS13 activity. In a preferred embodiment, the pharmaceutically acceptable salt is sodium chloride or potassium chloride.

In another embodiment, the present invention provides stabilized ADAMTS13 formulations comprising 0.05 mg/ml to 10.0 mg/ml ADAMTS13; 0 mM to 200 mM of a pharmaceutically acceptable salt; 1 mM to 10 mM calcium; a sugar and/or sugar alcohol; a nonionic surfactant; and a buffering agent for maintaining a pH of between about 6.5 and about 7.5. In a preferred embodiment, the formulation contains between about 2 mM and about 4 mM calcium. In a preferred embodiment, the pharmaceutically acceptable salt is sodium chloride or potassium chloride.

In another embodiment, the present invention provides stabilized ADAMTS13 formulations comprising 0.05 mg/ml to 10.0 mg/ml ADAMTS13; 0 mM to 200 mM of a pharmaceutically acceptable salt; 0.5 mM to 20 mM calcium; between about 2% and about 6% of a sugar and/or sugar alcohol; a nonionic surfactant; and a buffering agent for maintaining a pH of between about 6.5 and about 7.5. In certain embodiments, the sugar and/or sugar alcohol is selected from the group consisting of sucrose, trehalose, mannitol, and a combination thereof. In a preferred embodiment, the sugar and/or sugar alcohol is a mixture of sucrose and mannitol. In a particular embodiment, the mixture of sucrose and mannitol consists of about 1% sucrose and about 3% mannitol. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride.

In another embodiment, the present invention provides stabilized ADAMTS13 formulations comprising 0.05 mg/ml to 10.0 mg/ml ADAMTS13; 0 mM to 200 mM of a pharmaceutically acceptable salt; 0.5 mM to 20 mM calcium; a sugar and/or sugar alcohol; between about 0.01% and 0.1% of a nonionic surfactant; and a buffering agent for maintaining a pH of between about 6.5 and about 7.5. In certain embodiments, the surfactant is selected from the group consisting of Polysorbate 20, Polysorbate 80, Pluronic F-68, BRIJ 35, and a combination thereof. In a preferred embodiment, the sugar and/or sugar alcohol is a mixture of sucrose and mannitol. In a particular embodiment, the surfactant is Polysorbate 80. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride.

In another embodiment, the present invention provides stabilized ADAMTS13 formulations comprising 0.05 mg/ml to 10.0 mg/ml ADAMTS13; 0 mM to 200 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5, wherein the buffering agent is histidine or HEPES. In certain embodiments, the buffering agent is present at a concentration between about 5 mM and about 100 mM, preferably between about 10 mM and about 50 mM. In another preferred embodiment, the pH of the formulation is 7.0±0.2. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride.

In another embodiment, the present invention provides stabilized ADAMTS13 formulations comprising 0.05 mg/ml to 10.0 mg/ml ADAMTS13; 0 mM to 200 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5. In certain embodiments, the formulation further comprises between about 0.5 µM and about 20 µM zinc. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride.

In a preferred embodiment, the present invention provides a stabilized ADAMTS13 formulation comprising 0.05 mg/ml to 10.0 mg/ml ADAMTS13; 0 to 60 mM NaCl; 2 mM to 4 mM calcium; 2% to 4% mannitol; 0.5% to 2% sucrose; 0.025 to 0.1% Polysorbate 80; and 10 mM to 50 mM histidine (pH 7.0±0.2). In one embodiment, the formulation further comprises between about 0.5 µM and about 20 µM zinc.

In another embodiment, stabilized low salt ADAMTS13 formulations are provided comprising 0.05 mg/ml to 10.0 mg/ml ADAMTS13; less than about 100 mM of a pharmaceutically acceptable salt; 0.5 mM to 20 mM calcium; a sugar and/or sugar alcohol; a nonionic surfactant; and a buffering agent for maintaining a pH of approximately between 6.5 and 7.5. In a preferred embodiment, the pharmaceutically acceptable salt is sodium chloride or potassium chloride. In a preferred embodiment, the low salt ADAMTS13 formulation is a lyophilized formulation.

In one embodiment, a stabilized low salt ADAMTS13 formulation is provided comprising 0.05 mg/ml to 10.0 mg/ml ADAMTS13; less than about 100 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5 contains between about 50 units per mL and about 1000 units per mL of ADAMTS13 activity. In a preferred embodiment, the pharmaceutically acceptable salt is sodium chloride or potassium chloride. In a preferred embodiment, the low salt ADAMTS13 formulation is a lyophilized formulation.

In another embodiment, the present invention provides stabilized low salt ADAMTS13 formulations comprising 0.05 mg/ml to 10.0 mg/ml ADAMTS13; less than about 100 mM of a pharmaceutically acceptable salt; 1 mM to 10 mM calcium; a sugar and/or sugar alcohol; a nonionic surfactant; and a buffering agent for maintaining a pH of between about 6.5 and about 7.5. In a preferred embodiment, the formulation contains between about 2 mM and about 4 mM calcium. In a preferred embodiment, the pharmaceutically acceptable salt is sodium chloride or potassium chloride. In a preferred embodiment, the low salt ADAMTS13 formulation is a lyophilized formulation.

In another embodiment, the present invention provides stabilized low salt ADAMTS13 formulations comprising 0.05 mg/ml to 10.0 mg/ml ADAMTS13; less than about 100 mM of a pharmaceutically acceptable salt; 0.5 mM to 20 mM calcium; between about 2% and about 6% of a sugar and/or sugar alcohol; a nonionic surfactant; and a buffering agent for maintaining a pH of between about 6.5 and about 7.5. In certain embodiments, the sugar and/or sugar alcohol is selected from the group consisting of sucrose, trehalose, mannitol, and a combination thereof. In a preferred embodiment, the sugar and/or sugar alcohol is a mixture of sucrose and mannitol. In a particular embodiment, the mixture of sucrose and mannitol consists of about 1% sucrose and about 3% mannitol. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride. In a preferred embodiment, the low salt ADAMTS13 formulation is a lyophilized formulation.

In another embodiment, the present invention provides stabilized low salt ADAMTS13 formulations comprising 0.05 mg/ml to 10.0 mg/ml ADAMTS13; less than about 100 mM of a pharmaceutically acceptable salt; 0.5 mM to 20 mM calcium; a sugar and/or sugar alcohol; between about 0.01% and 0.1% of a nonionic surfactant; and a buffering agent for maintaining a pH of between about 6.5 and about 7.5. In certain embodiments, the surfactant is selected from the group consisting of Polysorbate 20, Polysorbate 80, Pluronic F-68, BRIJ 35, and a combination thereof. In a preferred embodiment, the sugar and/or sugar alcohol is a mixture of sucrose and mannitol. In a particular embodiment, the surfactant is Polysorbate 80. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride. In a preferred embodiment, the low salt ADAMTS13 formulation is a lyophilized formulation.

In another embodiment, the present invention provides stabilized low salt ADAMTS13 formulations comprising 0.05 mg/ml to 10.0 mg/ml ADAMTS13; less than about 100 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5, wherein the buffering agent is histidine or HEPES. In certain embodiments, the buffering agent is present at a concentration between about 5 mM and about 100 mM, preferably between about 10 mM and about 50 mM. In another preferred embodiment, the pH of the formulation is 7.0±0.2. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride. In a preferred embodiment, the low salt ADAMTS13 formulation is a lyophilized formulation.

In another embodiment, the present invention provides stabilized low salt ADAMTS13 formulations comprising 0.05 mg/ml to 10.0 mg/ml ADAMTS13; less than about 100 mM of a pharmaceutically acceptable salt; 0.5 mM to 20 mM calcium; a sugar and/or sugar alcohol; a nonionic surfactant; and a buffering agent for maintaining a pH of between about 6.5 and about 7.5. In certain embodiments, the formulation further comprises between about 0.5 µM and about 20 µM zinc. In certain embodiments, the formulation comprises between about 1 mM and about 10 mM calcium, preferably between about 2 mM and about 4 mM calcium. In a preferred embodiment, the pharmaceutically acceptable salt is sodium chloride or potassium chloride. In a preferred embodiment, the low salt ADAMTS13 formulation is a lyophilized formulation.

In a preferred embodiment, the present invention provides a stabilized low salt ADAMTS13 formulation comprising 0.05 mg/ml to 10.0 mg/ml ADAMTS13; less than about 100 mM NaCl; 2 mM to 4 mM calcium; 2% to 4% mannitol; 0.5% to 2% sucrose; 0.025 to 0.1% Polysorbate 80; and 10 mM to 50 mM histidine (pH 7.0±0.2). In one embodiment, the formulation further comprises between about 0.5 µM and about 20 µM zinc. In a preferred embodiment, the low salt ADAMTS13 formulation is a lyophilized formulation.

In one embodiment, the present invention provides a stabilized formulation of ADAMTS13 (A13) comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized A13 formulation, the formulation comprises between about 1.0 mM and about 10.0 mM calcium. In a preferred embodiment, the formulation contains between about 2.0 and about 4.0 mM calcium.

In another embodiment of the stabilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized A13 formulation, the formulation further comprises between about 0.5 μM and 20 μM zinc.

In a specific embodiment, the present invention provides a stabilized formulation of ADAMTS13 (A13) comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a stabilized low salt formulation of ADAMTS13 (A13) comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt A13 formulation, the formulation comprises between about 1.0 mM and about 10.0 mM calcium. In a preferred embodiment, the formulation contains between about 2.0 and about 4.0 mM calcium.

In another embodiment of the stabilized low salt A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt A13 formulation, the formulation further comprises between about 0.5 μM and 20 μM zinc.

In a specific embodiment, the present invention provides a stabilized low salt formulation of ADAMTS13 (A13) comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In a related embodiment, the present invention provides a stabilized lyophilized formulation of ADAMTS13 (A13), wherein the formulation is lyophilized from a liquid formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized lyophilized A13 formulation, the formulation further comprises between about 0.5 µM and 20 µM zinc.

In a specific embodiment, the present invention provides a stabilized lyophilized formulation of ADAMTS13 (A13), wherein the formulation is lyophilized from a liquid formulation comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In a related embodiment, the present invention provides a stabilized low salt lyophilized formulation of ADAMTS13 (A13), wherein the formulation is lyophilized from a liquid formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized low salt lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt lyophilized A13 formulation, the formulation further comprises between about 0.5 µM and 20 µM zinc.

In a specific embodiment, the present invention provides a stabilized low salt lyophilized formulation of ADAMTS13 (A13), wherein the formulation is lyophilized from a liquid formulation comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

IV. Stability of ADAMTS13 Formulations

In certain embodiments, the ADAMTS13 formulations provided herein may be stable for an extended period of time when stored at a certain temperature, for example, at about −80° C., −20° C., 4° C., 18° C., room temperature, 25° C., 30° C., 35° C., 37° C., 40° C., or higher. In some embodiments, an extended period of time is at least about a week. In other embodiments, an extended period of time may comprise at least about 2 weeks, or at least about 3 week, or at least about 1 month, or at least about 2 months, or at least about 3, 4, 5, 6, 7, 8, 9, 10, 11, 12, 14, 16, or 18 months. In yet other embodiments, the formulations of the invention may be stable for at least about 2, 3, 4, 5 or more years.

In certain embodiments of the invention, stability may be measured by one or more biophysical and/or enzymatic properties of the A13 or rA13 protein in the formulation. Non-limiting examples of properties that may be used to assess stability include, enzymatic activity, specific activity, the degree of mono- or poly-dispersity of the protein, the extent of dimerization, oligomerization, or aggregation of the protein, the degree of unfolding of the protein.

One skilled in the art will readily know of other measures of stability that may be employed to assess the stability of an ADAMTS13 formulation, including without limitation, gel filtration, dynamic or static light scattering, analytical ultracentrifugation, rp-HPLC, ion-exchange chromatography, fourier transform infrared spectroscopy, calorimetry, differential scanning calorimetry, NMR spectroscopy, mass spectrometry, small angle x-ray scattering (SAX), polyacrylamide gel electrophoresis, and the like.

In one embodiment, the present invention provides formulations of A13 or rA13 that retain at least about 50% of the total ADAMTS13 activity after storage for an extended period of time. In other embodiments, a formulation is provided that retains at least about 60%, or at least about 70%, 80%, 90%, 91%, 92%, 93%, 94%, 95%, 96%, 97%, 98%, 99%, or 100% of the total ADAMTS13 activity after storage for an extended period of time.

In another embodiment, formulations are provided that maintain at least about 50% of the ADAMTS13 specific activity after storage for an extended period of time. In other embodiments, a formulation is provided that retains at least about 60%, or at least about 70%, 80%, 90%, 91%, 92%, 93%, 94%, 95%, 96%, 97%, 98%, 99%, or 100% of the ADAMTS13 specific activity after storage for an extended period of time.

In other embodiments, the formulations of the invention will possess a specific activity of at least about 600 U of FRETS-VWF73 activity per mg ADAMTS13 protein after storage for an extended period of time. In other embodiments, a formulation provided herein will have at least about 700 U/mg A13, or at least about 800 U/mg, 900 U/mg, 1000 U/mg, 1100 U/mg, 1200 U/mg, 1300 U/mg, 1400 U/mg, 1500 U/mg, or higher specific activity after storage for an extended period of time.

In one embodiment, an A13 formulation provided herein will have a polydispersity, as determined by dynamic light scattering analysis, of less than about 50% after storage for an extended period of time. In other embodiments, an A13 formulation will have a polydispersity of less than about 45%, or of less than about 40%, 35%, 30%, 25%, 20%, 15%, 10%, 5% polydispersity, as measured by dynamic light scattering analysis after storage for an extended period of time.

In another embodiment of the invention, an A13 formulation provided herein will have an A13 protein population consisting of at least about 50% A13 monomers after storage for an extended period of time. In other embodiments, a formulation may have at least about 60% A13 monomers, or at least about 70%, 75%, 80%, 85%, 90%, 95%, 96%, 97%, 98%, 99%, or a higher percentage of A13 monomers.

V. ADAMTS13 Expression and Purification

In certain embodiments, an ADAMTS13 protein used in the formulations provided herein may be expressed, produced, or purified according to a method disclosed previously, for example, in U.S. Pat. No. 6,926,894, US 2005/0266528, US 2007/0015703, U.S. patent application Ser. No. 12/437,384, U.S. patent application Ser. No. 12/847,999, and WO 2002/42441, all of which are hereby incorporated by reference in their entirety for all purposes.

A. Host Cells and Vectors

Recombinant ADAMTS proteins can be produced by expression in any suitable prokaryotic or eukaryotic host system. Examples of eukaryotic cells include, without limitation, mammalian cells, such as CHO, COS, HEK 293, BHK, SK-Hep, and HepG2; insect cells, for example SF9 cells, SF21 cells, S2 cells, and High Five cells; and yeast cells, for example *Saccharomyces* or *Schizosaccharomyces* cells. In one embodiment, the ADAMTS proteins can be expressed in bacterial cells, yeast cells, insect cells, avian cells, mammalian cells, and the like. For example, in a human cell line, a hamster cell line, or a murine cell line. In one particular embodiment, the cell line is a CHO, BHK, or HEK cell line. In a preferred embodiment, the cell line is a CHO cell line.

In one embodiment, the cells may be any mammalian cell that can be cultured, preferably in a manufacturing process (i.e., at least 1 liter), to produce a desired ADAMTS protein such as ADAMTS13. Examples include the monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/–DHFR, such as the DUKX-B11 subclone (CHO, Uriaub and Chasin, Proc. Natl. Acad. Sci. USA, 77:4216 (1980)); mouse Sertoli cells (TM4, Mather, Biol. Reprod, 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N. Y. Acad. Sci., 383:44-68 (1982)); MRC 5 cells; FS4 cells; and the human hepatoma line (Hep G2). Preferably, the cell line is a rodent cell line, especially a hamster cell line such as CHO or BHK.

A wide variety of vectors can be used for the expression of an ADAMTS protein (e.g., ADAMTS13) and can be selected from eukaryotic and prokaryotic expression vectors. In certain embodiments, a plasmid vector is contemplated for use in expressing an ADAMTS protein (e.g., ADAMTS13). In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will comprise a nucleotide sequence encoding an ADAMTS protein (e.g., ADAMTS13) operable linked to one or more control sequences, for example, a promoter.

A preferred method of preparing stable CHO cell clones expressing a recombinant ADAMTS protein is as follows. A DHFR deficient CHO cell line DUKX-B11 is transfected with a DHFR expression vector to allow for expression of the relevant recombinant protein, essentially as described in U.S. Pat. No. 5,250,421 (Kaufman et al., Genetics Institute, Inc.). Selection is carried out by growth in Hypoxanthine/Thymidine (HT) free media and amplification of the relevant region coding for expression of the recombinant ADAMTS protein and DHFR gene is achieved by propagation of the cells in increasing concentrations of methotrexate. Where appropriate, CHO cell lines may be adapted for growth in serum and/or protein free medium, essentially as described in U.S. Pat. No. 6,100,061 (Reiter et al, Immuno Aktiengesellschaft).

In another preferred embodiment, stable HEK293 cells are prepared by transfecting with a construct containing a hygromycin selectable marker and selecting transformants by antibiotic resistance.

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Accordingly, in certain embodiments, a viral vector is used to introduce a nucleotide sequence encoding an ADAMTS protein (e.g., ADAMTS13) into a host cell for expression. The viral vector will comprise a nucleotide sequence encoding an ADAMTS protein (e.g., ADAMTS13) operable linked to one or more control sequences, for example, a promoter. Alternatively, the viral vector may not contain a control sequence and will instead rely on a control sequence within the host cell to drive expression of the ADAMTS protein. Non-limiting examples of virus vectors that may be used to deliver a nucleic acid include Adenoviral vectors, AAV vectors, and Retroviral vectors.

In one embodiment, an Adenovirus expression vector include those constructs containing adenovirus sequences sufficient to support packaging of the construct and to ultimately express an ADAMTS construct that has been cloned therein. Adenoviral vectors allow for the introduction of foreign sequences up to 7 kb (Grunhaus et al., Seminar in Virology, 200(2):535-546, 1992)).

In another embodiment, an adeno-associated virus (AAV) can be used to introduce a nucleotide sequence encoding an ADAMTS protein (e.g., ADAMTS13) into a host cell for expression. AAV systems have been described previously and are generally well known in the art (Kelleher and Vos, Biotechniques, 17(6):1110-7, 1994; Cotten et al., Proc Natl Acad Sci USA, 89(13):6094-6098, 1992; Curiel, Nat Immun, 13(2-3):141-64, 1994; Muzyczka, Curr Top Microbiol Immunol, 158:97-129, 1992). Details concerning the generation and use of rAAV vectors are described, for example, in U.S. Pat. Nos. 5,139,941 and 4,797,368, each incorporated herein by reference in their entireties for all purposes.

In one embodiment, a retroviral expression vector can be used to introduce a nucleotide sequence encoding an ADAMTS protein (e.g., ADAMTS13) into a host cell for expression. These systems have been described previously and are generally well known in the art (Mann et al., Cell, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., Science, 272(5259):263-267, 1996; Zufferey et al., Nat Biotechnol, 15(9):871-875, 1997; Blomer et al., J Virol., 71(9):6641-6649, 1997; U.S. Pat. Nos. 6,013,516 and 5,994,136).

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived form viral systems such as vaccinia virus, adeno-associated viruses, herpes viruses, retroviruses, etc., using promoters such as CMV, SV40, EF-1, UbC, RSV, ADV, BPV, and β-actin.

In certain embodiments, the cell-culture expression of ADAMTS13 may comprise the use of a microcarrier. The present invention provides, among other aspect, methods of large-scale ADAMTS protein expression. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. In another embodiment, these growth requirements are met via the use of a suspension cell culture.

B. Cultivation Methods

In certain embodiments, ADAMTS13 expression can comprise the use of a cell culture system operated under a batch or continuous mode of operation. For example, when batch cell cultures are utilized, they may be operated under single batch, fed-batch, or repeated-batch mode. Likewise, continuous cell cultures may be operated under, for example, perfusion, turbidostat or chemostat mode. Batch and continuous cell cultivation may be performed under either suspension or adherence conditions. When operated under suspension conditions, the cells will be freely suspended and mixed within the culture medium. Alternatively, under adherence conditions, the cells will be bound to a solid phase, for example, a microcarrier, a porous microcarrier, disk carrier, ceramic cartridge, hollow fiber, flat sheet, gel matrix, and the like.

A batch culture is typically a large scale cell culture in which a cell inoculum is cultured to a maximum density in a tank or fermenter, and harvested and processed as a single batch. A fed-batch culture it typically a batch culture which is supplied with either fresh nutrients (e.g., growth-limiting substrates) or additives (e.g., precursors to products). The feed solution is usually highly concentrated to avoid dilution of the bioreactor. In a repeated-batch culture, the cells are placed in a culture medium and grown to a desired cell density. To avoid the onset of a decline phase and cell death, the culture is then diluted with complete growth medium before the cells reach their maximum concentration. The amount and frequency of dilution varies widely and depends on the growth characteristics of the cell line and convenience of the culture process. The process can be repeated as many times as required and, unless cells and medium are discarded at subculture, the volume of culture will increase stepwise as each dilution is made. The increasing volume may be handled by having a reactor of sufficient size to allow dilutions within the vessel or by dividing the diluted culture into several vessels. The rationale of this type of culture is to maintain the cells in an exponentially growing state. Serial subculture is characterized in that the volume of culture is always increasing stepwise, there can be multiple harvests, the cells continue to grow and the process can continue for as long as desired. In certain embodiments, an ADAMTS protein (e.g., ADAMTS13) may be recovered after harvesting the supernatant of a batch culture.

A continuous culture can be a suspension culture that is continuously supplied with nutrients by the inflow of fresh medium, wherein the culture volume is usually kept constant by the concomitant removal of spent medium. In chemostat and turbidostat methods, the extracted medium contains cells. Thus, the cells remaining in the cell culture vessel must grow to maintain a steady state. In the chemostat method, the growth rate is typically controlled by controlling the dilution rate, i.e., the rate at which fresh medium is added. The growth rate of the cells in the culture may be controlled, for example, at a sub-maximal growth rate, by alteration of the dilution rate. In contrast, in the turbidostat method, the dilution rate is set to permit the maximum growth rate that the cells can achieve at the given operating conditions, such as pH and temperature.

In a perfusion culture, the extracted medium is depleted of cells, which are retained in the culture vessel, for example, by filtration or by centrifugal methods that lead to the reintroduction of the cells into the culture. However, typically membranes used for filtration do not retain 100% of cells, and so a proportion are removed when the medium is extracted. It may not be crucial to operate perfusion cultures at very high growth rates, as the majority of the cells are retained in the culture vessel.

Stirred-tank reactor system can be used for batch and continuous cell cultures operated under suspension or adherent modes. Generally, the stirred-tank reactor system can be operated as any conventional stirred-tank reactor with any type of agitator such as a Rushton, hydrofoil, pitched blade, or marine.

C. Culture Mediums

ADAMTS13 may be expressed in culture mediums which are free of exogenously added protein. "Protein free culture medium" and related terms refers to culture medium lacking protein that is from a source exogenous to or other than the cells in the culture, which naturally shed proteins during growth. In one embodiment, an ADAMTS13 protein can be expressed in a medium which is free of exogenously added protein (i.e., protein-free) and is supplemented with zinc, calcium, and/or nicotinamide (vitamin B3). In certain embodiments, the protein free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary protein free culture mediums are taught in U.S. Pat. Nos. 6,171,825 and 6,936,441, WO 2007/077217, U.S. Patent Application Publication Numbers 2008/0009040 and 2007/0212770, and U.S. patent application Ser. No. 12/847,999, the disclosures of which are incorporated herein by reference in their entireties for all purposes.

Methods of preparing animal protein-free and chemically defined culture mediums are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes. In one embodiment, the culture medium used to express an ADAMTS13 protein is animal protein-free or oligopeptide-free medium. In certain embodiments, the culture medium may be chemically defined. In certain embodiments, the culture media may contain at least one polyamine at a concentration of about 0.5 mg/L to about 10 mg/L.

ADAMTS13 protein can also be expressed in culture mediums which are free of exogenously added oligopeptides. In one embodiment, ADAMTS13 is expressed in a culture medium which is free of exogenously added oligopeptides (i.e., polypeptide-free) and is supplemented with zinc, calcium, and/or nicotinamide (vitamin B3). In certain embodiments, the oligopeptide free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary oligopeptide free culture mediums are taught in U.S. Pat. Nos. 6,171,825 and 6,936,441, WO 2007/077217, U.S. Patent Application Publication Numbers 2008/0009040 and 2007/0212770, and U.S. patent application Ser. No. 12/847,999 the disclosures of which are incorporated herein by reference in their entireties for all purposes.

ADAMTS13 protein can also be expressed in culture mediums which are free of serum. In one embodiment, ADAMTS13 is expressed in a culture medium which is free of exogenously added serum (i.e., serum-free) and is supplemented with zinc, calcium, and/or nicotinamide (vitamin B3). In certain embodiments, the serum-free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary serum-free culture mediums are taught in U.S. Pat. Nos. 6,171,825 and 6,936,441, WO 2007/077217, U.S. Patent Application Publication Numbers 2008/0009040 and 2007/0212770, and U.S. patent application Ser. No. 12/847,999, the disclosures of which are incorporated herein by reference in their entireties for all purposes.

ADAMTS13 protein can also be expressed in culture mediums which are free of animal proteins. In one embodiment, ADAMTS13 is expressed in a culture medium which is free of exogenously added animal proteins or polypeptides (i.e., animal protein free) and is supplemented with zinc, calcium, and/or nicotinamide (vitamin B3). In certain embodiments, the animal protein free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary animal protein free culture mediums are taught in U.S. Pat. Nos. 6,171,825 and 6,936,441, WO 2007/077217, U.S. Patent Application Publication Numbers 2008/0009040 and 2007/0212770, and U.S. patent application Ser. No. 12/847,999, the disclosures of which are incorporated herein by reference in their entireties for all purposes.

ADAMTS13 proteins can also be expressed in culture mediums supplemented with additional calcium, zinc, and/or vitamin B3, as described in U.S. patent application Ser. No. 12/847,999, the disclosure of which is incorporated herein by reference in its entirety for all purposes. In certain embodiments, the medium may be an animal protein-free, oligopeptide-free, or chemically defined medium. In certain embodiments, the animal protein-free or oligopeptide free medium is prepared as taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes, both of which are incorporated herein by reference in their entireties for all purposes, and supplemented with additional calcium, zinc, and/or vitamin B3. In a specific embodiment, the chemically defined culture medium may be similar to a Dulbecco's Modified Eagle's Media (DMEM), which has been supplemented with additional calcium, zinc, and/or vitamin B3, in order to increase the specific activity of an ADAMTS protein expressed in a cell cultured in the medium. In yet other embodiments, the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal.

D. ADAMTS13 Purification

Methods for native ADAMTS13 purification from pooled plasma are well known in the art. Likewise, methods for the expression and purification of recombinant ADAMTS13 are also known in the art. For example, recombinant expression and purification are taught by Plaimauer and Scheiflinger, *Semin Hematol.* 2004 January; 41(1):24-33; Plaimauer B et al., *F. Blood.* 2002 Nov. 15; 100(10):3626-32. Epub 2002 Jul. 12; Bruno K et al., J Thromb Haemost. 2005 May; 3(5):1064-73, and U.S. patent application Ser. No. 12/847,999, the disclosures of which are all expressly incorporated by reference herein in their entireties for all purposes.

Additionally, the present disclosure provides additional methods for the purification of recombinant ADAMTS13. In one embodiment, recombinant ADAMTS13 is expressed in recombinant CHO cells and purified from the resulting conditioned media by POROS HS cation exchange chromatography. To eliminate undesirable dimeric, monomeric, and/or aggregated ADAMTS13, the composition in then subjected to size exclusion gel filtration. ADAMTS13 compositions will generally also be subjected to at least one, preferably two, viral removal or inactivation steps.

In certain embodiments, the methods provided herein for the preparation of an ADAMTS13 formulation will further include at least one viral inactivation or removal steps. In certain embodiments, the methods provided herein will include at least two or at least three, viral inactivation or removal steps. Non-limiting examples of viral inactivation or removal steps that may be employed with the methods provided herein include, solvent detergent treatment (Horowitz et al., Blood Coagul Fibrinolysis 1994 (5 Suppl 3):S21-S28 and Kreil et al., Transfusion 2003 (43):1023-1028, the disclosures of which are expressly incorporated by reference herein in their entireties for all purposes), nanofiltration (Hamamoto et al., Vox Sang 1989 (56)230-236 and Yuasa et al., J Gen Virol. 1991 (72 (pt 8)):2021-2024, the disclosures of which are expressly incorporated by reference herein in their entireties for all purposes). In a preferred embodiment, the present invention provides methods for the preparation of an ADAMTS13 formulation comprising solvent detergent treatment and nanofiltration.

In one embodiment, a method is provided for providing a virally safe ADAMTS13 protein formulation, the method comprising the steps of (a) culturing a cell harboring a nucleic acid encoding an ADAMTS13 protein in a culture medium; (b) recovering a portion of the culture medium supernatant containing the ADAMTS13 protein; (c) enriching the ADAMTS13 protein with a chromatographic step; (d) performing at least one virus inactivation or removal step; and (e) formulating the enriched ADAMTS13 composition according to a formulation provided herein, thereby providing a virally safe ADAMTS13 formulation. In one embodiment, the culture medium contains zinc, calcium, and optionally nicotinamide (vitamin B3). In a preferred embodiment, the step of culturing a cell comprises a continuous culture (e.g., perfusion or chemostatic culture). In another preferred embodiment, the culture is maintained at a temperature between 34° C. and 37° C. In yet another preferred embodiment, the culture is maintained at a pH between 6.9 and 7.2. In one embodiment, the virus removal step is nanofiltration.

In aspect embodiment, the present invention provides a method for manufacturing a stabilized ADAMTS13 formulation, the method comprising the steps of: (a) expressing an ADAMTS13 protein, or a biologically active derivative thereof, in a cell cultured in a medium comprising zinc at a concentration from about 2 µM to about 12 µM and calcium at a concentration from about 0.5 mM to about 1.5 mM; (b) purifying the ADAMTS13 protein; and (c) preparing a formulation according to any one of the formulations provided herein.

In one embodiment, the present invention provides a method for manufacturing a stabilized ADAMTS13 formulation, the method comprising the steps of: (i) expressing an ADAMTS13 protein, or a biologically active derivative thereof, in a cell cultured in a medium comprising zinc at a concentration from about 2 µM to about 12 µM and calcium at a concentration from about 0.5 mM to about 1.5 mM; (ii) purifying the ADAMTS13 protein; and (iii) preparing a formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized A13 formulation, the formulation comprises between about 1.0 mM and about 10.0 mM calcium. In a preferred embodiment, the formulation contains between about 2.0 and about 4.0 mM calcium.

In another embodiment of the stabilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized A13 formulation, the formulation further comprises between about 0.5 µM and 20 µM zinc.

In a specific embodiment, the present invention provides a stabilized formulation of ADAMTS13 (A13) comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for manufacturing a stabilized ADAMTS13 formulation, the method comprising the steps of: (i) expressing an ADAMTS13 protein, or a biologically active derivative thereof, in a cell cultured in a medium comprising zinc at a concentration from about 2 µM to about 12 µM and calcium at a concentration from about 0.5 mM to about 1.5 mM; (ii) purifying the ADAMTS13 protein; and (iii) preparing a formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt A13 formulation, the formulation comprises between about 1.0 mM and about 10.0 mM calcium. In a preferred embodiment, the formulation contains between about 2.0 and about 4.0 mM calcium.

In another embodiment of the stabilized low salt A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt A13 formulation, the formulation further comprises between about 0.5 µM and 20 µM zinc.

In a specific embodiment, the present invention provides a stabilized low salt formulation of ADAMTS13 (A13) comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for manufacturing a stabilized ADAMTS13 formulation, the method comprising the steps of: (i) expressing an ADAMTS13 protein, or a biologically active derivative thereof, in a cell cultured in a medium comprising zinc at a concentration from about 2 µM to about 12 µM and calcium at a concentration from about 0.5 mM to about 1.5 mM; (ii) purifying the ADAMTS13 protein; and (iii) preparing a formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized lyophilized A13 formulation, the formulation further comprises between about 0.5 µM and 20 µM zinc.

In a specific embodiment, the present invention provides a stabilized lyophilized formulation of ADAMTS13 (A13), wherein the formulation is lyophilized from a liquid formulation comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for manufacturing a stabilized ADAMTS13 formulation, the method comprising the steps of: (i) expressing an ADAMTS13 protein, or a biologically active derivative thereof, in a cell cultured in a medium comprising zinc at a concentration from about 2 µM to about 12 µM and calcium at a concentration from about 0.5 mM to about 1.5 mM; (ii) purifying the ADAMTS13 protein; and (iii) preparing a formulation comprising (a) at least 100 units ADAMTS13 activity (i.e., FRETS-vWF73 activity) per mg ADAMTS13;

(b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized low salt lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt lyophilized A13 formulation, the formulation further comprises between about 0.5 µM and 20 µM zinc.

In a specific embodiment, the present invention provides a stabilized low salt lyophilized formulation of ADAMTS13 (A13), wherein the formulation is lyophilized from a liquid formulation comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

1. Solvent and Detergent (S/D) Treatment

In order to inactivate various viral contaminants which may be present in an ADAMTS13 formulation, one or more ADAMTS13 intermediate solutions may be subjected to a solvent detergent (S/D) treatment. Methods for the detergent treatment of solutions are well known in the art (for review see, Pelletier J P et al., Best Pract Res Clin Haematol. 2006; 19(1):205-42, the disclosure of which is expressly incorporated by reference herein in its entirety for all purposes). Generally, any standard S/D treatment may be used in conjunction with the methods provided herein. For example, an exemplary protocol for an S/D treatment is provided below.

In one embodiment, Triton X-100, Tween-20, and tri(n-butyl)phosphate (TNBP) are added to an ADAMTS13 intermediate solution at final concentrations of at or about 1.0%, 0.3%, and 0.3%, respectively. The mixture is then stirred at a temperature at or about between 18° C. and 25° C. for at least about an hour.

2. Nanofiltration and Ultra/Diafiltration

In order to reduce the viral load of an ADAMTS13 protein formulation provided herein, the formulation, or an intermediate composition, may be nanofiltered using a suitable nanofiltration device. In certain embodiments, the nanofiltration device will have a mean pore size of at or about between 15 nm and 200 nm. Examples of nanofilters suitable for this use include, without limitation, DVD, DV 50, DV 20 (Pall), Viresolve NFP®, Viresolve NFR® (Millipore), Planova® 15N, 20N, 35N, and 75N (Planova). In a specific embodiment, the nanofilter may have a mean pore size of at or about between 15 and 72 nm, or at or about between 19 and 35 nm, or of at or about 15 nm, 19 nm, 20 nm, 35 nm, or 72 nm. In a preferred embodiment, the nanofilter will have a mean pore size of at or about 19 nm, 20 nm, or 35 nm, such as an Asahi PLANOVA® 20N or PLANOVA® 35N filter or equivalent thereof.

Subsequent to nanofiltration, the filtrate may optionally be concentrated by ultrafiltration and/or the buffer composition adjusted by diafiltration. In certain embodiments, the ultrafiltration is carried out in a cassette with an open channel screen and the ultrafiltration membrane has a nominal molecular weight cut off (NMWCO) of less than at or about 175 kDa or less than at or about 170, 160, 150, 140, 130, 120, 110, 100, 90, 80, 70, 60, 50, 40, 30, or fewer kDa. In a preferred embodiment, the ultrafiltration membrane has a NMWCO of no more than 30 kDa. In another preferred embodiment, the ultrafiltration membrane has a NMWCO of no more than 30 kDa.

3. Lyophilization and Heat Treatment

In yet other embodiments, the viral activity of a lyophilized ADAMTS13 formulation, which may have previously been subjected to other viral inactivation or removal steps such as nanofiltration, may be further reduced by heat treatment of the lyophilized composition. Heat treatments for the inactivation of viral loads in blood factors are well known in the art (for example, see, Piszkiewicz et al., Thromb Res. 1987 Jul. 15; 47(2):235-41; Piszkiewicz et al., Curr Stud Hematol Blood Transfus. 1989; (56):44-54; Epstein and Fricke, Arch Pathol Lab Med. 1990 March; 114(3):335-40).

VI. Administration and Methods of Treatment

The formulations can be administered for therapeutic or prophylactic treatments. Generally, for therapeutic applications, formulations are administered to a subject with a disease or condition associated with ADAMTS13 or VWF dysfunction or otherwise in need thereof, in a "therapeutically effective dose." Formulations and amounts effective for these uses will depend upon the severity of the disease or condition and the general state of the patient's health. Single or multiple administrations of the formulations may be administered depending on the dosage and frequency as required and tolerated by the patient.

A "patient" or "subject" for the purposes of the present invention includes both humans and other animals, particularly mammals. Thus the compositions, formulations, and methods are applicable to both human therapy and veterinary applications. In a particular embodiment the patient is a mammal, and in one embodiment, is a human. Other known treatments and therapies for conditions associated with ADAMTS13 or VWF dysfunction can be used in combination with the formulations and methods provided by the invention.

In one aspect of the invention, methods of making stabilized rA13 formulation having high specific activities are provided. In one embodiment, the method comprises the steps of expressing an ADAMTS13 protein, or a biologically active derivative thereof, in a cell cultured in a medium comprising zinc at a concentration from about 2 µM to about 12 µM and calcium at a concentration from about 0.5 mM to about 1.5 mM, purifying the A13 protein, and preparing a formulation as described above. In certain embodiments, the culture media is further supplemented with vitamin B3 at a concentration from about 1 mg/L to about 20 mg/L.

In another aspect, the present invention provides methods of treating or preventing a disease or condition associated with an ADAMTS13 or VWF dysfunction. In another embodiment, the invention provides methods of treating or preventing a disease or condition associated with the formation and/or presence of one or more thrombus. In another embodiment, the invention provides methods of disintegrating one or more thrombus in a subject in need thereof. In yet other embodiments, the invention provides methods of treating or preventing an infarction in subject in need thereof. Generally, the methods provided by the invention comprise administering an ADAMTS13 formulation as provided herein to a subject in need thereof.

Non-limiting examples of disorders associated with the formation and/or the presence of one or more thrombus are hereditary thrombotic thrombocytopenic purpura (TTP), acquired TTP, arterial thrombosis, acute myocardial infarction (AMI), stroke, sepsis, and disseminated intravascular coagulation (DIC).

Non-limiting examples of disorders associated with an infarction, include without limitation, myocardial infarction (heart attack), pulmonary embolism, cerebrovascular events such as stroke, peripheral artery occlusive disease (such as gangrene), antiphospholipid syndrome, sepsis, giant-cell arteritis (GCA), hernia, and volvulus.

A. Treatment and Prophylaxis for ADAMTS13 and vWF Dysfunction

In aspect embodiment, the present invention provides a method for treating or preventing a disease or condition associated with an ADAMTS13 or VWF dysfunction, the method comprising administering to a subject in need thereof an ADAMTS13 formulation according to any one of the formulations provided herein.

In one embodiment, the present invention provides a method for treating or preventing a disease or condition associated with an ADAMTS13 or VWF dysfunction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized A13 formulation, the formulation comprises between about 1.0 mM and about 10.0 mM calcium. In a preferred embodiment, the formulation contains between about 2.0 and about 4.0 mM calcium.

In another embodiment of the stabilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized A13 formulation, the formulation further comprises between about 0.5 µM and 20 µM zinc.

In a specific embodiment, the present invention provides a stabilized formulation of ADAMTS13 (A13) comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing a disease or condition associated with an ADAMTS13 or VWF dysfunction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt A13 formulation, the formulation comprises between about 1.0 mM and about 10.0 mM calcium. In a preferred embodiment, the formulation contains between about 2.0 and about 4.0 mM calcium.

In another embodiment of the stabilized low salt A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt A13 formulation, the formulation further comprises between about 0.5 µM and 20 µM zinc.

In a specific embodiment, the present invention provides a stabilized low salt formulation of ADAMTS13 (A13) comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing a disease or condition associated with an ADAMTS13 or VWF dysfunction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized lyophilized A13 formulation, the formulation further comprises between about 0.5 µM and 20 µM zinc.

In a specific embodiment, the present invention provides a stabilized lyophilized formulation of ADAMTS13 (A13), wherein the formulation is lyophilized from a liquid formulation comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing a disease or condition associated with an ADAMTS13 or VWF dysfunction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized low salt lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt lyophilized A13 formulation, the formulation further comprises between about 0.5 µM and 20 µM zinc.

In a specific embodiment, the present invention provides a stabilized low salt lyophilized formulation of ADAMTS13 (A13), wherein the formulation is lyophilized from a liquid formulation comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

B. Treatment and Prophylaxis for Thrombotic Diseases and Conditions

In aspect embodiment, the present invention provides a method for treating or preventing a disease or condition with the formation and/or presence of a thrombus, the method comprising administering to a subject in need thereof an ADAMTS13 formulation according to any one of the formulations provided herein.

In one embodiment, the present invention provides a method for treating or preventing a disease or condition associated with the formation and/or presence of a thrombus, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized A13 formulation, the formulation comprises between about 1.0 mM and about 10.0 mM calcium. In a preferred embodiment, the formulation contains between about 2.0 and about 4.0 mM calcium.

In another embodiment of the stabilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized A13 formulation, the formulation further comprises between about 0.5 µM and 20 µM zinc.

In a specific embodiment, the present invention provides a stabilized formulation of ADAMTS13 (A13) comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing a disease or condition associated with the formation and/or presence of a thrombus, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt A13 formulation, the formulation comprises between about 1.0 mM and about 10.0 mM calcium. In a preferred embodiment, the formulation contains between about 2.0 and about 4.0 mM calcium.

In another embodiment of the stabilized low salt A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt A13 formulation, the formulation further comprises between about 0.5 µM and 20 µM zinc.

In a specific embodiment, the present invention provides a stabilized low salt formulation of ADAMTS13 (A13) comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing a disease or condition associated with the formation and/or presence of a thrombus, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized lyophilized A13 formulation, the formulation further comprises between about 0.5 μM and 20 μM zinc.

In a specific embodiment, the present invention provides a stabilized lyophilized formulation of ADAMTS13 (A13), wherein the formulation is lyophilized from a liquid formulation comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing a disease or condition associated with the formation and/or presence of a thrombus, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized low salt lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt lyophilized A13 formulation, the formulation further comprises between about 0.5 μM and 20 μM zinc.

In a specific embodiment, the present invention provides a stabilized low salt lyophilized formulation of ADAMTS13 (A13), wherein the formulation is lyophilized from a liquid formulation comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

C. Treatment and Prophylaxis for an Infarction

In aspect embodiment, the present invention provides a method for treating or preventing an infarction, the method comprising administering to a subject in need thereof an ADAMTS13 formulation according to any one of the formulations provided herein.

In one embodiment, the present invention provides a method for treating or preventing an infarction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized A13 formulation, the formulation comprises between about 1.0 mM and about 10.0 mM calcium. In a preferred embodiment, the formulation contains between about 2.0 and about 4.0 mM calcium.

In another embodiment of the stabilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized A13 formulation, the formulation further comprises between about 0.5 μM and 20 μM zinc.

In a specific embodiment, the present invention provides a stabilized formulation of ADAMTS13 (A13) comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing an infarction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt A13 formulation, the formulation comprises between about 1.0 mM and about 10.0 mM calcium. In a preferred embodiment, the formulation contains between about 2.0 and about 4.0 mM calcium.

In another embodiment of the stabilized low salt A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt A13 formulation, the formulation further comprises between about 0.5 μM and 20 μM zinc.

In a specific embodiment, the present invention provides a stabilized low salt formulation of ADAMTS13 (A13) comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing an infarction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 200 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized lyophilized A13 formulation, the formulation further comprises between about 0.5 µM and 20 µM zinc.

In a specific embodiment, the present invention provides a stabilized lyophilized formulation of ADAMTS13 (A13), wherein the formulation is lyophilized from a liquid formulation comprising (a) at least 100 units ADAMTS13 activity per mg ADAMTS13; (b) 0 to 200 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

In one embodiment, the present invention provides a method for treating or preventing an infarction, the method comprising administering to a subject in need thereof an ADAMTS13 formulation comprising (a) at least 100 units ADAMTS13 activity (i.e., FRETS-vWF73 activity) per mg ADAMTS13; (b) 0 mM to 100 mM of a pharmaceutically acceptable salt; (c) 0.5 mM to 20 mM calcium; (d) a sugar and/or sugar alcohol; (e) a nonionic surfactant; and (f) a buffering agent for maintaining a pH between 6.0 and 8.0. In one embodiment, the stabilized formulation of ADAMTS13 comprises at least 200 units A13 activity per mg ADAMTS13. In another embodiment, the stabilized formulation of ADAMTS13 comprises at least 400 units A13 activity per mg ADAMTS13. In a preferred embodiment, the stabilized formulation of ADAMTS13 comprises at least 600 units A13 activity per mg ADAMTS13. In a more preferred embodiment, the stabilized formulation of ADAMTS13 comprises at least 800 units A13 activity per mg ADAMTS13. In yet another preferred embodiment, the stabilized formulation of ADAMTS13 comprises at least 1000 units A13 activity per mg ADAMTS13. In one embodiment, the stabilized formulation of ADAMTS13 comprises between about 100 units and about 2000 units of ADAMTS13 activity per mg ADAMTS13.

In one embodiment of the stabilized low salt lyophilized A13 formulation, the formulation comprises between about 1.0 mM and about 10.0 mM calcium. In a preferred embodiment, the formulation contains between about 2.0 and about 4.0 mM calcium.

In another embodiment of the stabilized low salt lyophilized A13 formulation, the formulation comprises between about 2% and about 6% of a sugar and/or sugar alcohol. In a preferred embodiment, the formulation comprises between about 3% and about 5% of a sugar and/or sugar alcohol. In a specific embodiment, the formulation comprises about 4% of a sugar and/or sugar alcohol. In one embodiment, the sugar and/or sugar alcohol is selected from the group consisting of sucrose, trehalose, mannitol, and a combination thereof. In a preferred embodiment, the sugar and/or sugar alcohol is a mixture of sucrose and mannitol.

In one embodiment of the stabilized low salt lyophilized A13 formulation, the formulation comprises between about 0.01% and about 0.1% of a non-ionic surfactant. In a preferred embodiment, the formulation comprises about 0.05% of a non-ionic surfactant. In one embodiment, the surfactant is selected from the group consisting of Polysorbate 20, Polysorbate 80, Pluronic F-68, and BRIJ 35. In a preferred embodiment, the surfactant is Polysorbate 80.

In one embodiment of the stabilized low salt lyophilized A13 formulation, the formulation comprises between about 5 mM and about 100 mM of a buffering agent. In a preferred embodiment, the formulation comprises between about 10 mM and about 50 mM of a buffering agent. In another embodiment, the buffering agent is histidine or HEPES. In a preferred embodiment, the buffering agent is histidine. In one embodiment, the pH of the formulation is between about 6.5 and 7.5. In a preferred embodiment, the pH of the formulation is 7.0±0.2.

In one embodiment of the stabilized low salt lyophilized A13 formulation, the formulation further comprises between about 0.5 µM and 20 µM zinc.

In a specific embodiment, the present invention provides a stabilized low salt lyophilized formulation of ADAMTS13 (A13), wherein the formulation is lyophilized from a liquid formulation comprising (a) at least 100 units ADAMTS13 activity per mg ADAMTS13; (b) 0 to 60 mM NaCl; (c) 2 mM to 4 mM calcium; (d) 2% to 4% mannitol; (e) 0.5% to 2% sucrose; (f) 0.025 to 0.1% Polysorbate 80; and (g) 10 mM to 50 mM histidine (pH 7.0±0.2).

VII. ADAMTS13 Kits

In another aspect of the invention, kits are provided for the treatment of a disease or condition associated with ADAMTS13 or VWF dysfunction. In one embodiment, the kit comprises a formulation of A13 or rA13, as provided above. In some embodiments, the kits provided herein may contain one or more dose of a liquid or lyophilized formulation as provided herein. When the kits comprise a lyophilized A13 or rA13 formulation, generally the kits will also contain a suitable liquid for reconstitution of the liquid formulation, for example, sterile water or a pharmaceutically acceptable buffer. In some embodiments, the kits may comprise an ADAMTS13 formulation prepackaged in a syringe for administration by a health care professional or for home use.

In one embodiment, a kit is provided comprising between about 10 units of FRETS-VWF73 activity and about 10,000 units of FRETS-VWF73 activity. In other embodiments, the kit may provide, for example, between about 20 units of FRETS-VWF73 ($U_{FV73}$) activity and about 8,000 units of FRETS-VWF73 activity, or between about 30 $U_{FV73}$ and about 6,000 $U_{FV73}$, or between about 40 $U_{FV73}$ and about 4,000 $U_{FV73}$, or between about 50 $U_{FV73}$ and about 3,000 $U_{FV73}$, or between about 75 $U_{FV73}$ and about 2,500 $U_{FV73}$, or between about 100 $U_{FV73}$ and about 2,000 $U_{FV73}$, or between about 200 $U_{FV73}$ and about 1,500 $U_{FV73}$, or between about other ranges therein. In certain embodiments, a kit may provide about 10 units of FRETS-VWF73 activity, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more units of FRETS-VWF73 activity.

In certain embodiments, the kit will be for a single administration or dose of ADAMTS13. In other embodiments, the kit may contain multiple doses of ADAMTS13 for administration. In one embodiment, the kit may comprise an ADAMTS13 formulation prepackaged in a syringe for administration by a health care professional or for home use.

Samples of the supernatant from the bioreactors were taken weekly and analyzed for rA13 protein production by ELISA and rA13 activity by FRETS-VWF73 assay. Cell counts were determined by Nucleocounter technology. Dilution rates were measured and used for calculation of growth rates and volumetric productivities.

Under continuous culture conditions using chemically defined BACD-A13 medium supplemented with zinc and nicotinamide at a final concentration of 1.432 mg/L $ZnSO_4 7H_2O$ and 7.02 mg/L nicotinamide, high levels of rA13 protein production, between 0.9 and 1.3 mg/L/D, and specific activities, between about 800 and 1100 mU/μg rA13, were achieved (Table 1). Notably, volumetric and cell specific productivities increased over time in the long term culture, likely due to increasing growth and dilution rates over time. The high specific activity of the expressed rA13 could be at least maintained at a constantly high level over at least entire 7 weeks the culture was grown under chemostatic conditions. In fact, the specific activity of the rA13 produced in the culture actually increased from about 800 mU/μg A13 at week 2 to about 1100 mU/μg A13 at week 7.

TABLE 1

Fermentation data for batch experiment CP_07/18_M07: hA13 CHO Klon #985/1 985 DWCB#01.

| Chemostat Culture Week No. | Cell Concentration [10⁶ Cells/ml] | Specific Growth Rate [1/d] | Dilution Rate [1/d] | A13 FRETS [mU/ml] | A13 ELISA [g/ml] | Specific Activity [mU//μg] | FRETS Yield [U/L/d] | A13 Yield [mg/L/d] |
|---|---|---|---|---|---|---|---|---|
| 2 | 1.43 | 0.36 | 0.36 | 1954 | 2.48 | 788 | 713 | 0.91 |
| 3 | 1.56 | 0.41 | 0.40 | 2254 | 2.32 | 972 | 913 | 0.94 |
| 4 | 1.46 | 0.38 | 0.40 | 2244 | 2.41 | 931 | 889 | 0.95 |
| 5 | 1.58 | 0.43 | 0.43 | 2514 | 2.88 | 873 | 1086 | 1.24 |
| 6 | 1.70 | 0.51 | 0.46 | 2737 | 2.71 | 1010 | 1270 | 1.26 |
| 7 | 1.76 | 0.53 | 0.52 | 2322 | 2.18 | 1065 | 1200 | 1.13 |

VIII. Examples

A. Example 1: Expression of Recombinant ADAMTS13 (rA13)

A Chemostat cell-culture of the recombinant CHO cell line #640-2 expressing human ADAMTS13, was grown in chemically defined BACD-A13 medium supplemented with additional zinc and vitamin B3. The 10 L culture was maintained for 53 days and rA13 protein and activity production was monitored over time.

Recombinant CHO cells expressing human ADAMTS13 were adapted to a chemically defined proprietary medium (BCS medium). A DWCB was thawed and cell inoculum was prepared in BCS medium. Cells propagated from the rA13 expression clone #640-2 were transferred to a 10 L bioreactor with Rushton type impellers and cultivated in repeated batch cultures with proprietary BACD-A13 medium under an inline controlled pH of 7.15-7.20 at 37° C. with a dissolved oxygen concentration of 20% air saturation. After 2 batch cultures were grown to the final working volume of 10 L, the bioreactor was switched to continuous medium feed on day 5 and operated for an additional 48 days in a chemostat mode.

B. Example 2: Formulation of Purified Recombinant ADAMTS13 (rA13)

Recombinant ADAMTS13 was expressed in recombinant CHO cells and purified by anion exchange chromatography. The purified rA13 had a final concentration of approximately 750 μg/ml with a specific activity of approximately 850 mU/μg. rA13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3) sodium citrate. Samples were then divided evenly and half the samples were lyophilized.

Figure 3:
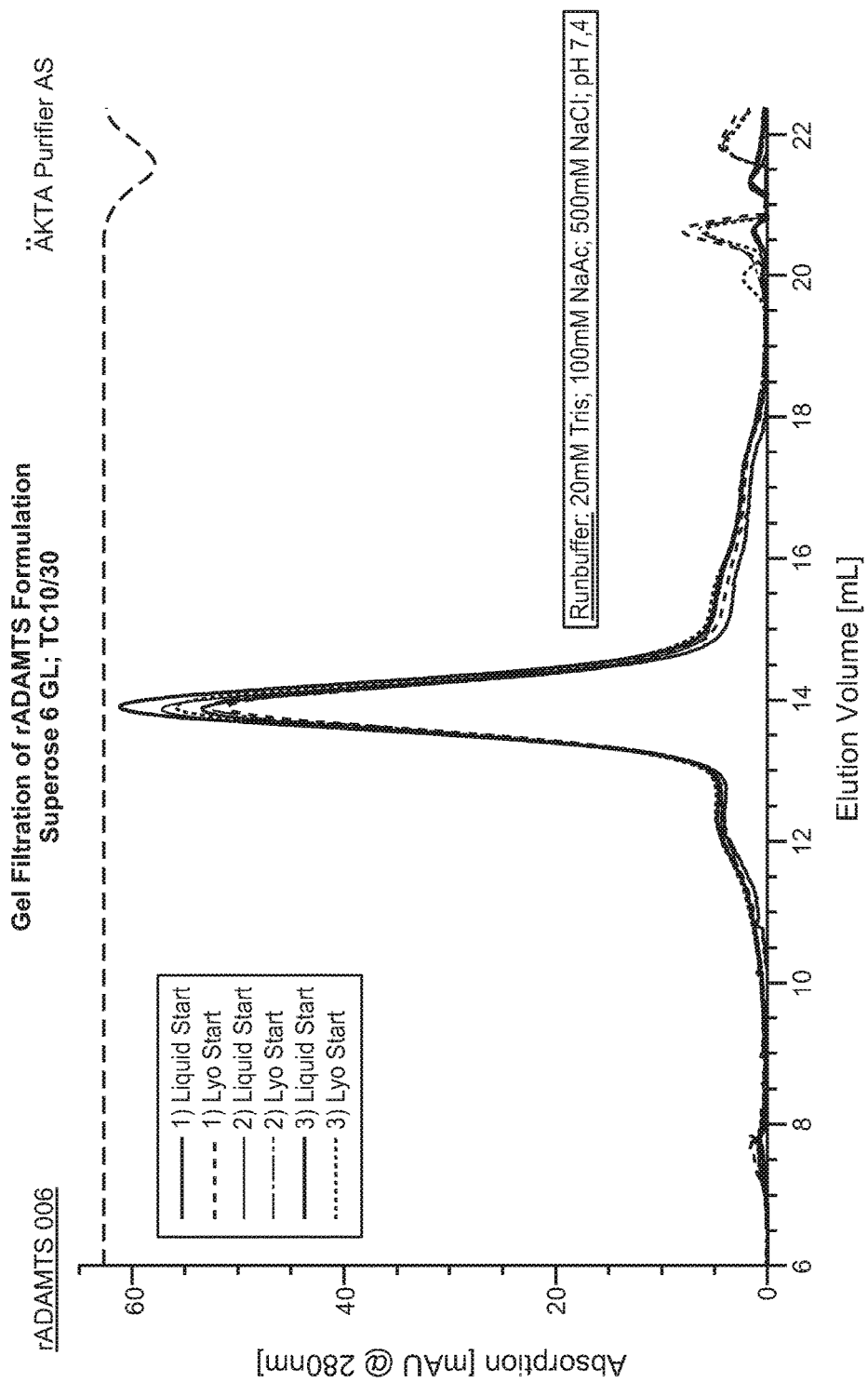
FIG. 3. Recombinant ADAMTS13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3) sodium citrate and samples were either loaded directly onto a Superose 6 gel filtration column or lyophilized and reconstituted with sterile water prior to loading. The ADAMTS13 formulations were then analyzed by gel filtration.

Lyophilized samples were reconstituted with sterile water to a final volume equal to that of the pre-lyophilized formulation. A single aliquot of each liquid and lyophilized formulation was then characterized by gel filtration by loading the sample onto a Superose 6 GL column (GE Healthcare). As can be seen in FIG. 3, all of the formulations resulted in ADAMTS13 samples that ran as a single peak corresponding to monomeric rA13 protein by gel filtration.

Figure 1A:
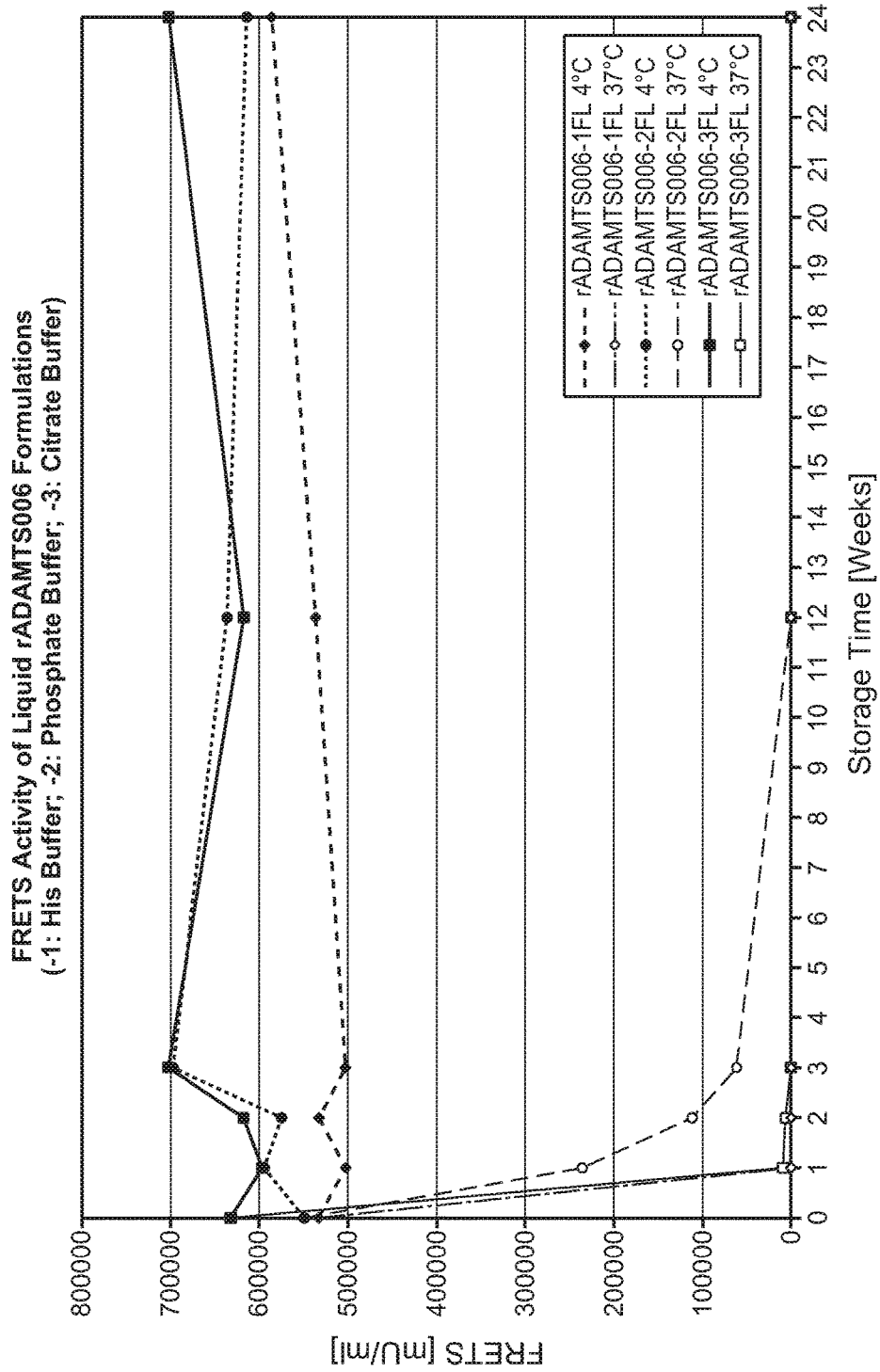
FIGS. 1A and 1B. Recombinant ADAMTS13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3) sodium citrate. Solutions were stored at 4° C. or 37° C. for up to 6 months. (A) FRETS-VWF73 activity and (B) ADAMTS13 protein concentration as measured by ELISA, were determined at the indicated time points.
Figure 1B:
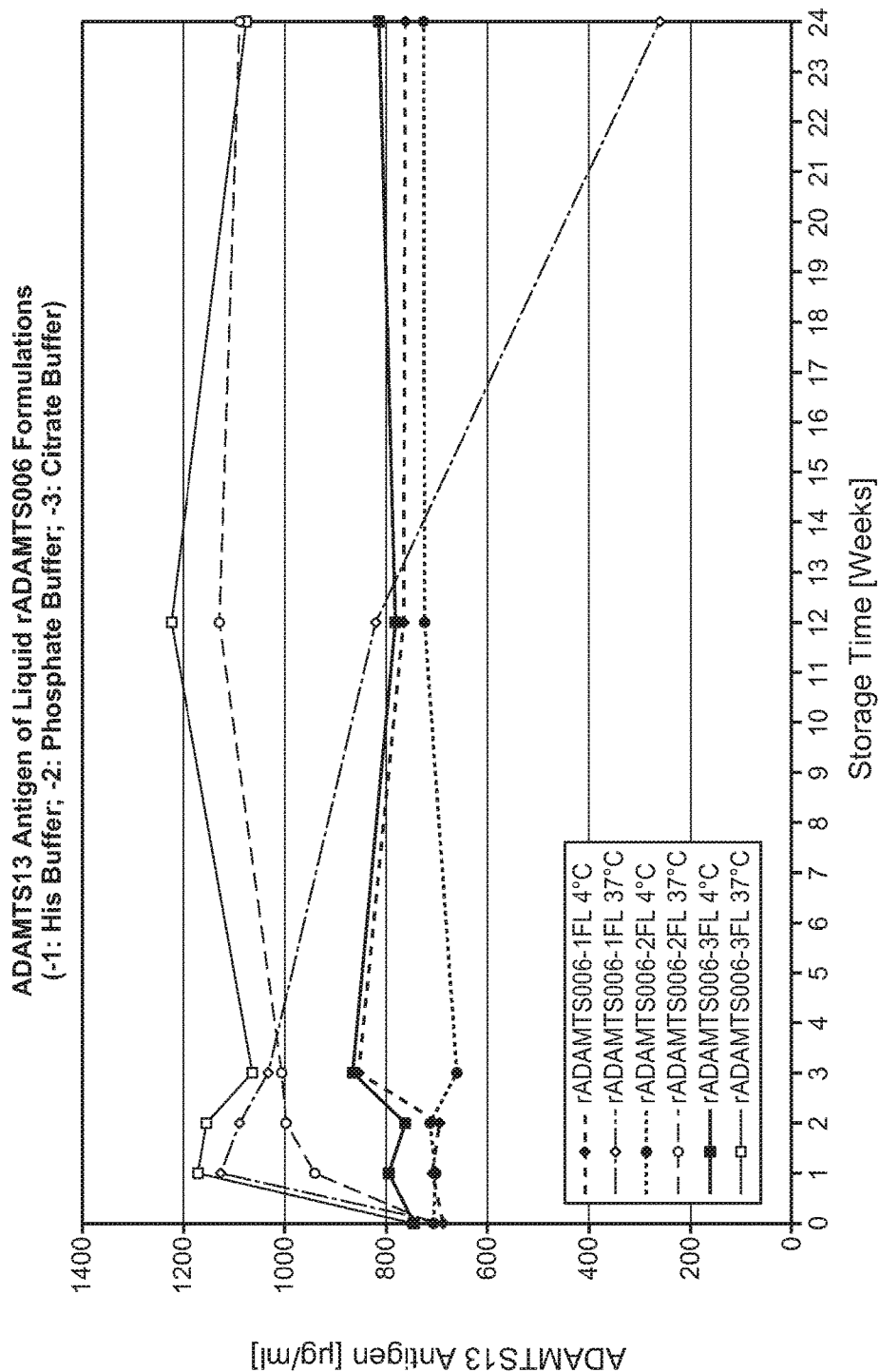
Figure 2A:
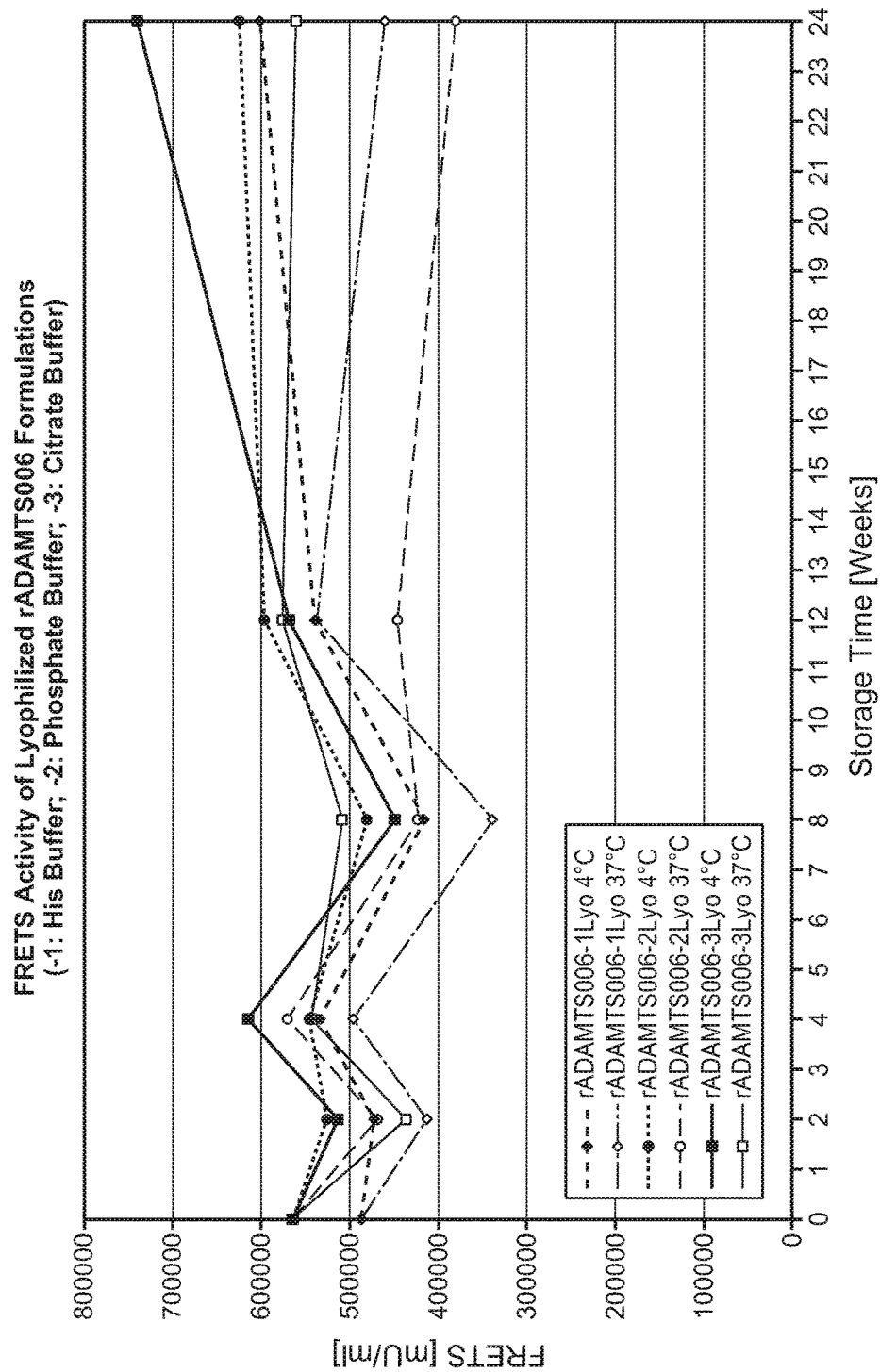
FIGS. 2A and 2B. Recombinant ADAMTS13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3) sodium citrate and lyophilized. Lyophilized formulations were stored at 4° C. or 37° C. for up to 6 months. ADAMTS13 formulations were reconstituted with sterile water and (A) FRETS-VWF73 activity and (B) ADAMTS13 protein concentration as measured by ELISA, were determined at the indicated time points.
Figure 2B:
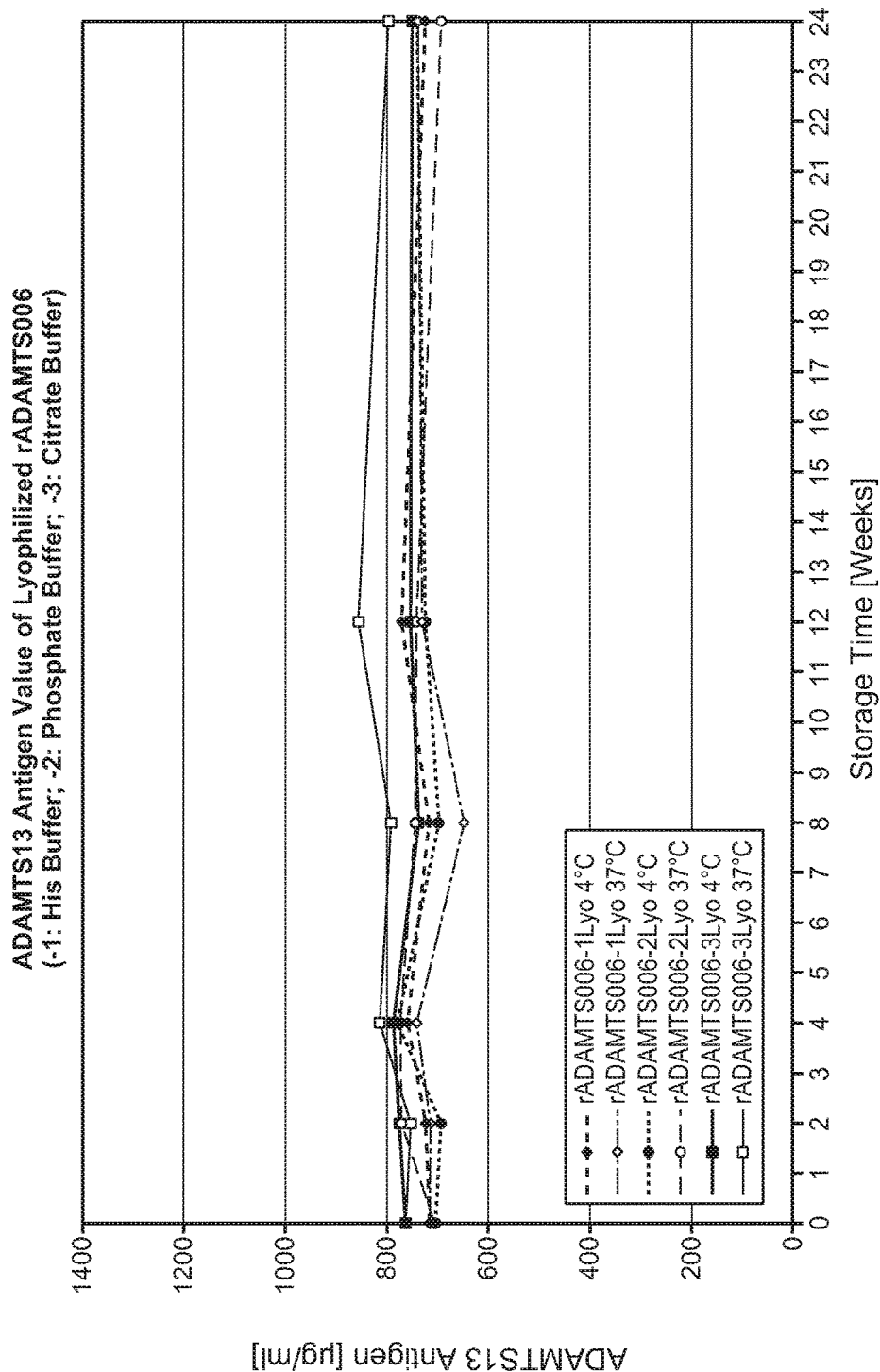

C. Example 3: Characterization of Activity Retention of rA13 Formulations Stored at 4° C. and 37° C.

rA13 samples formulated and aliquoted as in example 2 were stored at either 4° C. or 37° C. for up to 6 months time. Solution formulations were analyzed for rA13 protein concentration, as determined by ELISA, and rA13 activity by FRETS-VWF73 assay at 0, 1, 2, 3, 12, and 24 weeks (FIG. 1). Lyophilized samples were reconstituted with sterile water to a final volume equal to that of the pre-lyophilized formulation and analyzed similarly at 0, 2, 4, 8, 12, and 24 weeks (FIG. 2).

rA13 liquid formulations stored at 4° C. showed no loss in either antigen content, i.e. protein concentration, or FRETS-VWF73 activity at time points out to 6 months. As seen in FIG. 1, this was the case for all three formulations, buffered with histidine, phosphate, and sodium citrate, respectively. Conversely, liquid formulations, buffered with histidine or sodium citrate, displayed nearly complete loss of activity after one week at 37° C. (FIG. 1A; ◇=histidine, □=sodium citrate). This loss in activity was accompanied with a spike in the antigen content at one week for these samples, suggesting that the rA13 proteins were being denatured. The histidine liquid formulation of rA13 displayed drastically reduced antigen content at 3 and 6 months, suggesting that the protein was being degraded. Notably, liquid rA13 formulated with phosphate buffer showed significant activity at three weeks when stored at 37° C. (FIG. 1A; ○=phosphate buffer). Consistently, the antigen content of this formulation increased at a slower rate, suggesting that rA13 denaturation is retarded when formulated with phosphate buffer.

rA13 lyophilized formulations appeared to be stable for at least 6 months when stored at either 4° C. or 37° C. (FIG. 2). Lyophilized rA13 formulated with phosphate buffer displayed a gradual loss of activity (30% at 6 months) when stored at 37° C., but not at 4° C., however, this loss of activity was not accompanied by an increase in antigen availability by ELISA (FIG. 2; ○=phosphate buffer). No other lyophilized formulation showed a loss of activity or increase in antigen availability when stored at 4° C. or 37° C.

Figure 4A:
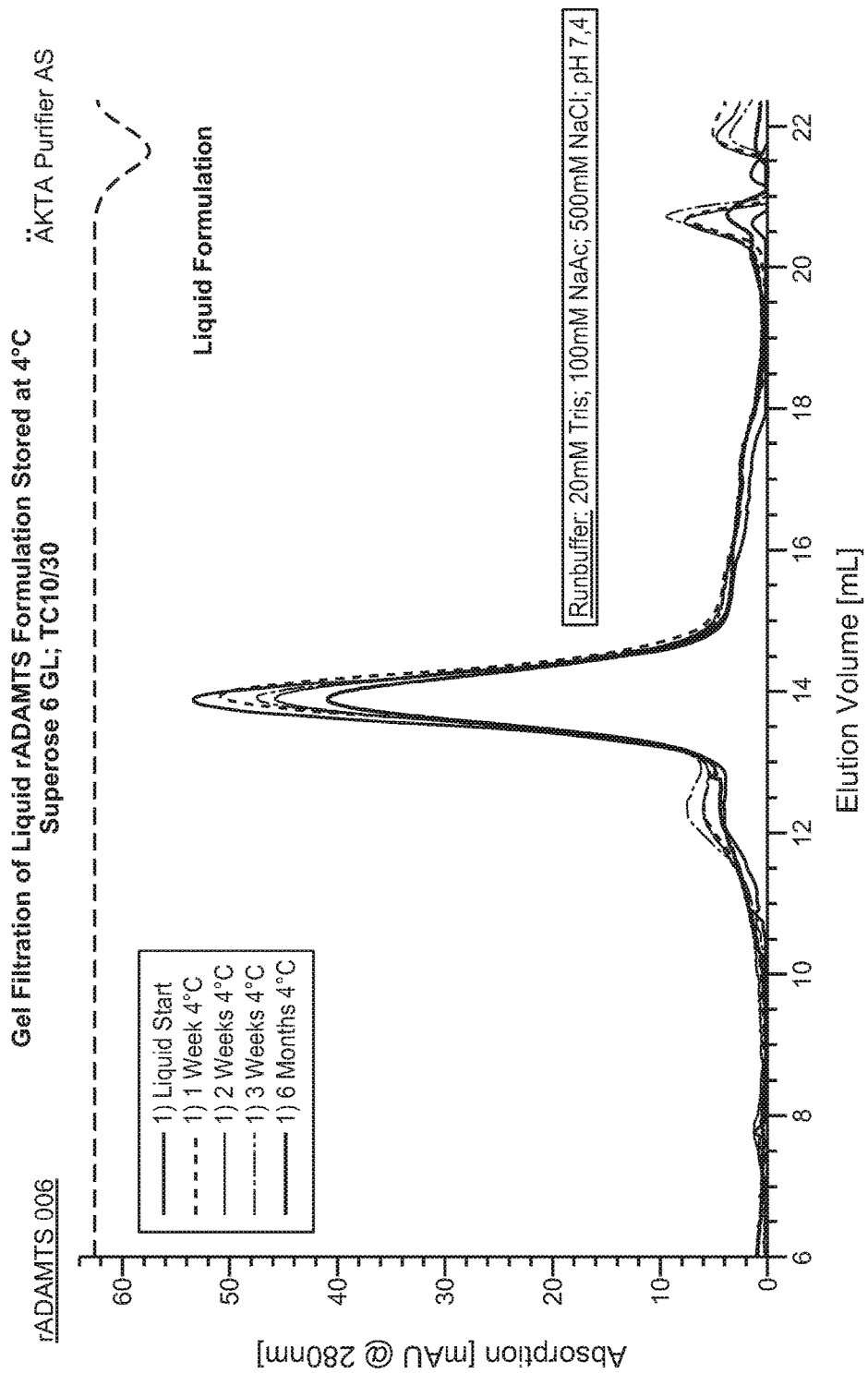
FIGS. 4A and 4B. Recombinant ADAMTS13 was formulated in buffer containing 150 mM NaCl, 2% sucrose, 0.05% polysorbate 80, and 20 mM histidine at pH 7.0. Solutions were stored at (A) 4° C. or (B) 37° C. for up to 6 months. ADAMTS13 formulations were then analyzed by gel filtration at the indicated time points.

D. Example 4: Conformational Stability of rA13 in Formulations Stored at 4° C. and 37° C.

rA13 samples formulated and aliquoted as in example 2 were stored at either 4° C. or 37° C. for up to 6 months time. The global conformations of rA13 formulated and stored in solution and lyophilized states was characterized by gel filtration at the time points described in example 3. Results of gel filtration experiments performed with the histidine formulated rA13 at 0, 1, 2, 3, and 24 weeks for the liquid formulations (FIG. 4) and 0, 2, 4, 8, 12, and 24 weeks for the lyophilized formulations (FIG. 5) are shown.

Figure 4B:
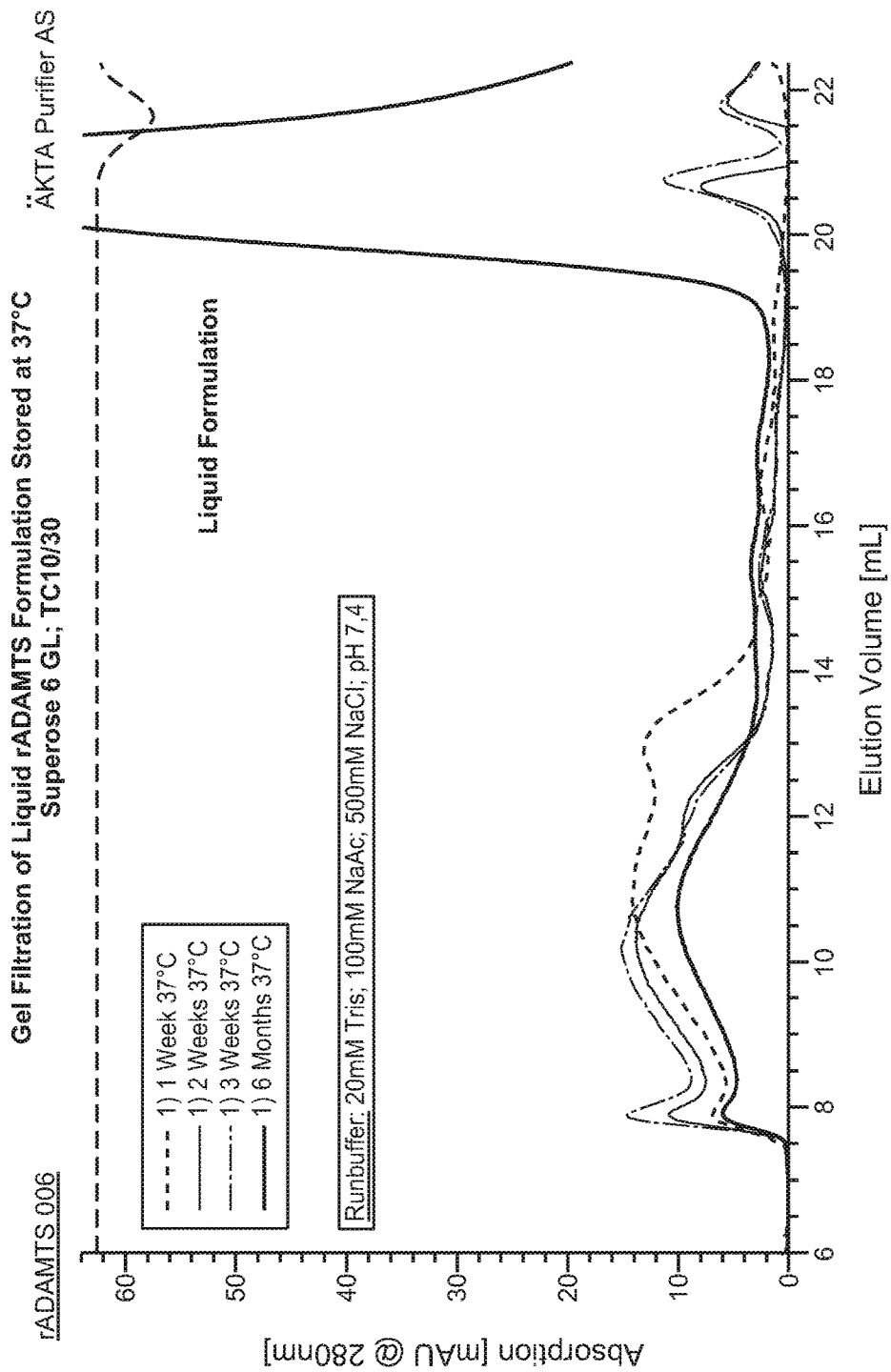
Figure 5A:
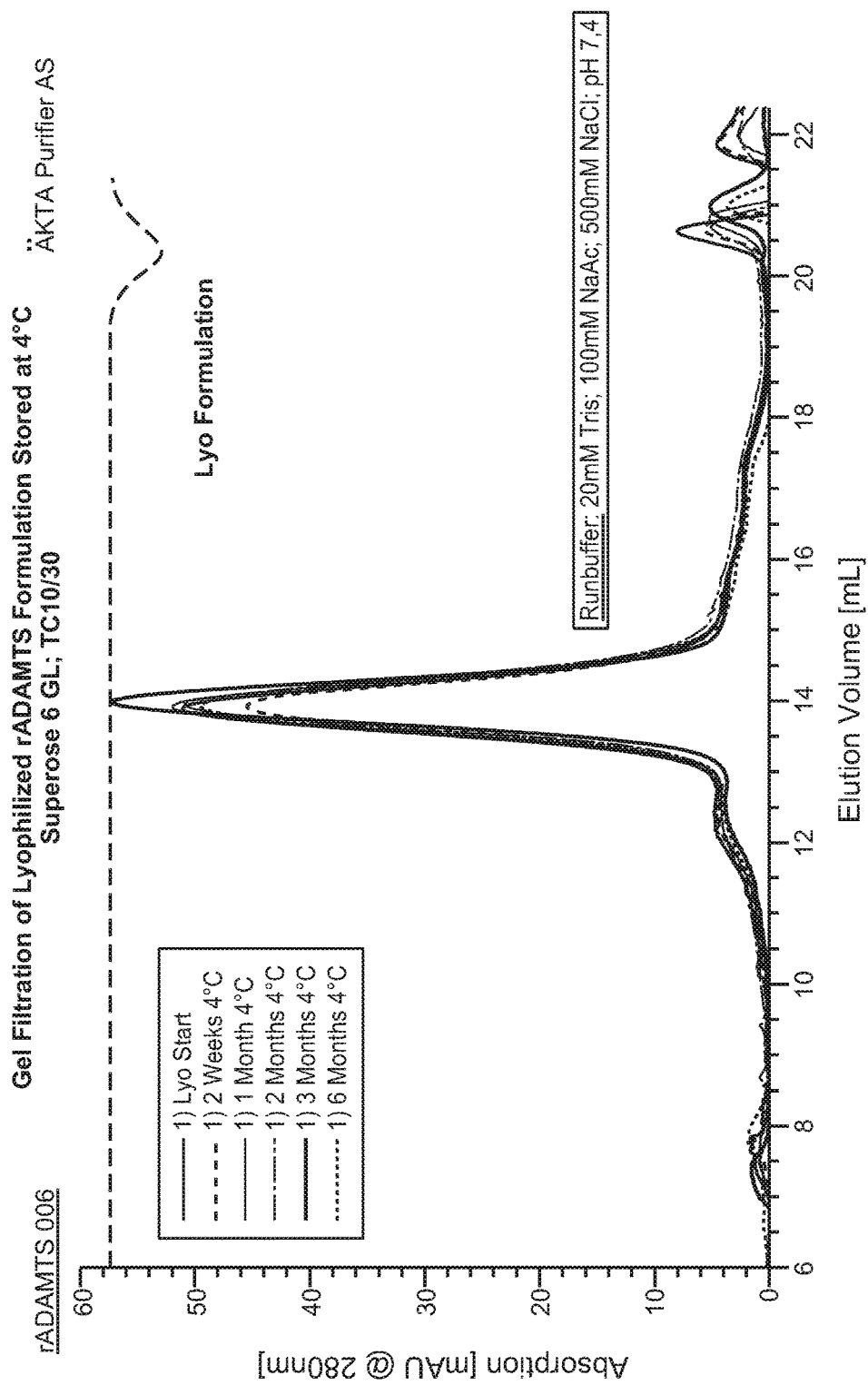
FIGS. 5A and 5B. Recombinant ADAMTS13 was formulated in buffer containing 150 mM NaCl, 2% sucrose, 0.05% polysorbate 80, and 20 mM histidine at pH 7.0 and then lyophilized. Lyophilized formulations were then stored at (A) 4° C. or (B) 37° C. for up to 6 months. ADAMTS13 formulations were reconstituted in sterile water at the indicated time points and analyzed by gel filtration.
Figure 5B:
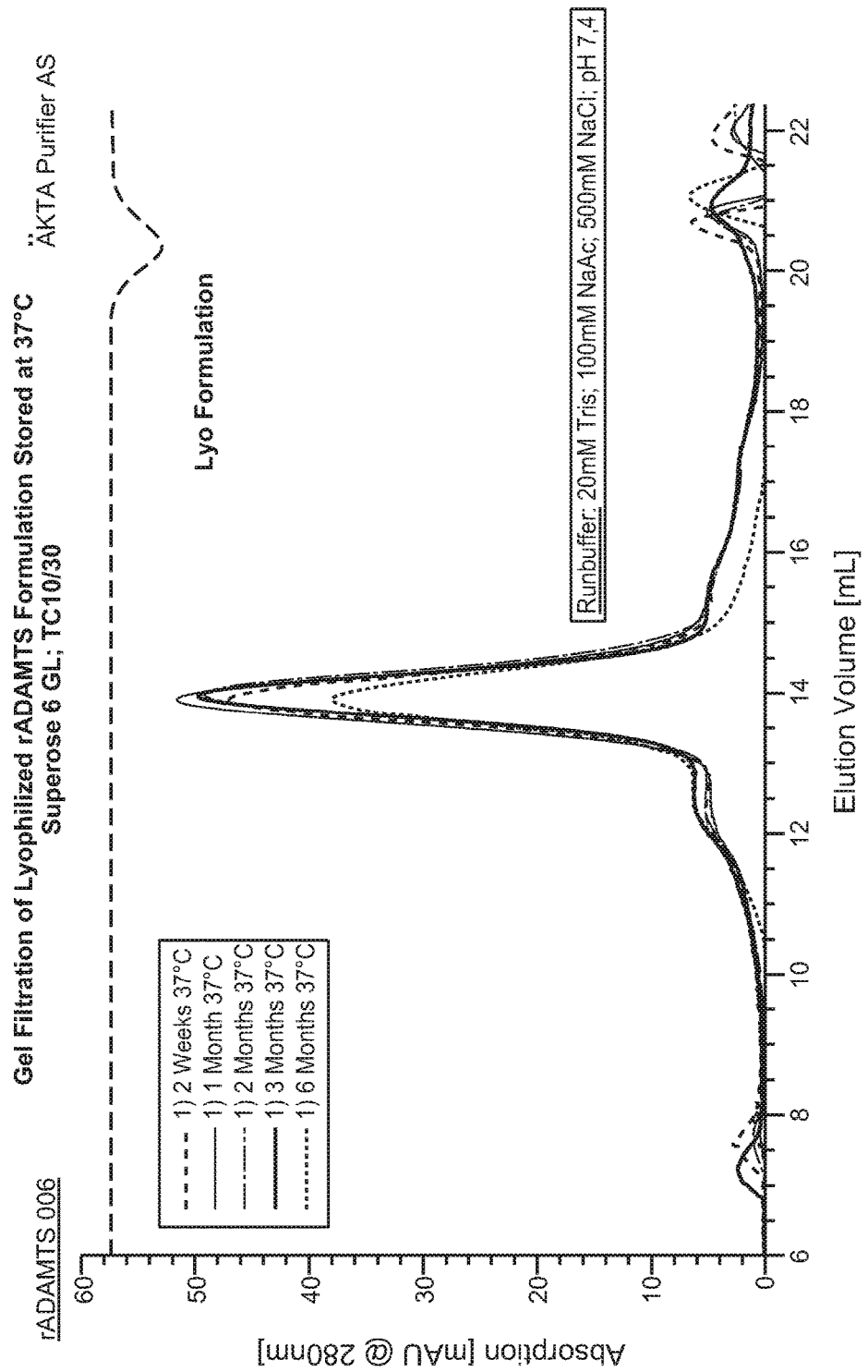

Liquid formulations with histidine, stored at 4° C. for up to 6 months, ran primarily as a monomer over gel filtration (FIG. 4A), suggesting that the protein is very stable in solution at 4° C. This result is consistent with those described in example 3, which showed that rA13 formulated with histidine and stored in solution at 4° C. for up to 6 months did not lose any FRETS-VWF73 activity. Conversely, rA13 formulated with histidine and stored at 37° C., ran as higher order/partially or wholly denatured species, as indicated by the reduced elution volumes/retention times (FIG. 4B). Consistent with the results seen in example 3, histidine formulated A13 stored at 37° C. for 6 months appeared to be mostly degraded.

Gel filtration experiments were repeated for each formulation, stored at 4° C. and 37° C., and relative areas under the eluted peaks were integrated in order to determine the relative populations of monomer rA13 (3), dimer rA13 (2), and aggregated/denatured rA13 (1) in the formulations. Results of the gel filtration experiments performed on the three lyophilized formulations stored at 4° C. and 37° C. for six months are given in Table 2. Lyophilized samples were reconstituted with sterile water to a final volume equal to that of the pre-lyophilized formulation prior to analysis via gel filtration.

TABLE 2

Relative area under the curve (AUC) for gel filtrations of reconstituted ADAMTS13 lyophilized formulations.

| | Relative peak area [%] | | |
|---|---|---|---|
| Peak No | Lyo start | Lyo 6 m 4° C. | Lyo 6 m 37° C. |
| Lyo__His (1) | | | |
| 1 (aggregate) | 2.8 | 3.2 | 2 |
| 2 (dimer") " | 11.7 | 10.7 | 16.9 |
| 3 (monomer) | 72.3 | 73.8 | 70.1 |
| 4 | 13.2 | 12.4 | 11.1 |
| Lyo__phosphate (2) | | | |
| 1 (aggregate) | 1.4 | 1.2 | 15.3 |
| 2 (dimer")" | 10.1 | 8.9 | 32.7 |
| 3 (monomer) | 74.7 | 78.4 | 43.9 |
| 4 | 13.9 | 11.6 | 8.1 |
| Lyo__citrate (3) | | | |
| 1 (aggregate) | 0.9 | 0.6 | 1 |
| 2 (dimer")" | 11.2 | 9.1 | 18.8 |
| 3 (monomer) | 74.2 | 77.9 | 70.3 |
| 4 | 13.8 | 12.4 | 9.9 |

Consistent with the results seen in example 3, lyophilized rA13 formulations displayed no increase in the amount of dimer or aggregate/denatured species after storage at 4° C. for at least 6 months. Similarly, rA13 formulated and lyophilized with histidine or sodium citrate showed only minor levels of dimerization when stored at 37° C. for at least 6 months. Furthermore, there was no indication that either of these formulations resulted increased levels of aggregation and/or denaturation. Conversely, rA13 formulated and lyophilized with phosphate buffer displayed significant levels of dimerization and aggregation and/or denaturation, when stored at 37° C. for at least 6 months.

Figure 6A:
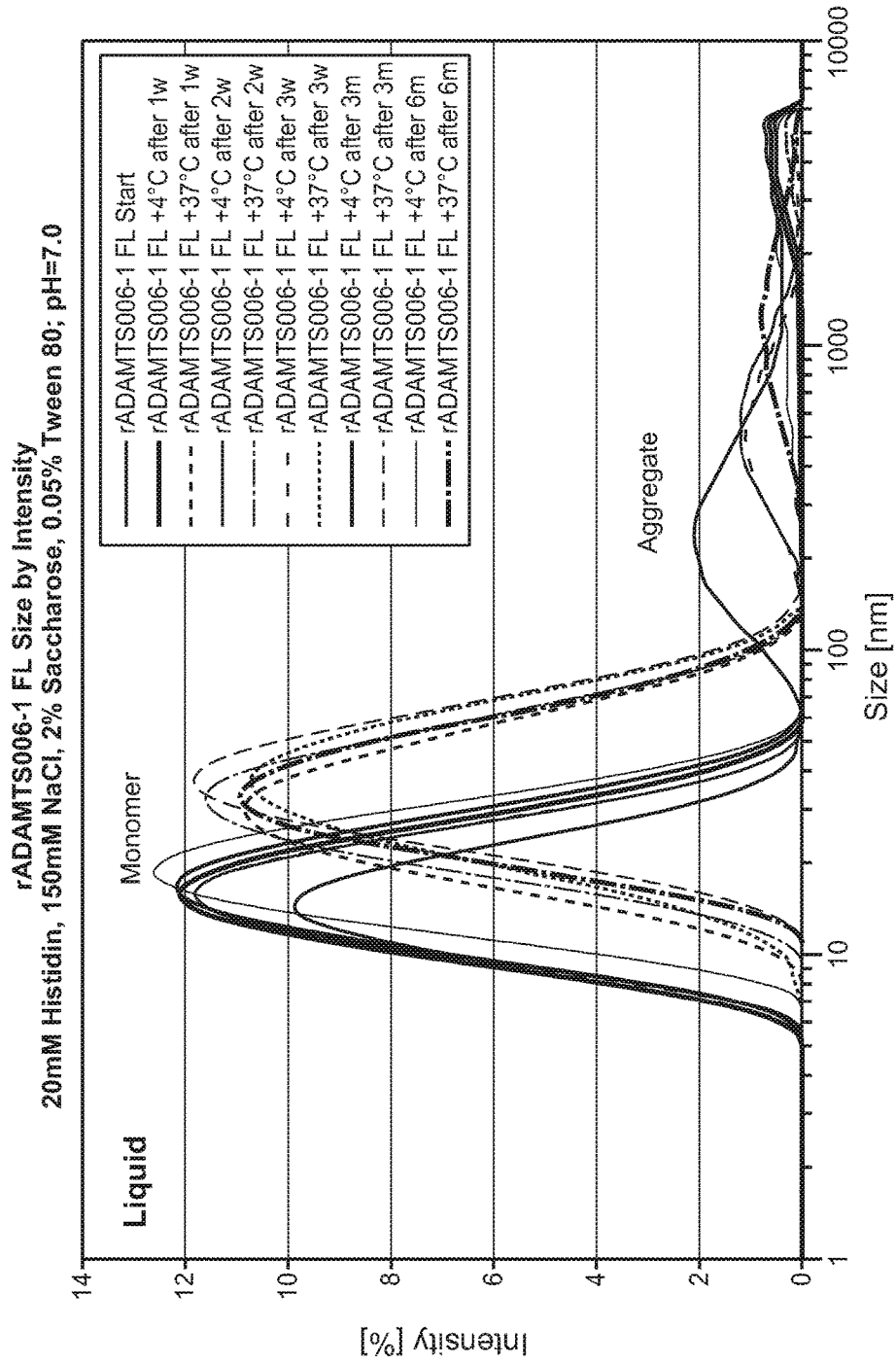
FIGS. 6A and 6B. Recombinant ADAMTS13 was formulated in buffer containing 150 mM NaCl, 2% sucrose, 0.05% polysorbate 80, and 20 mM histidine at pH 7.0 and then stored (A) in solution or (B) lyophilized at 4° C. or 37° C. for up to 6 months. Lyophilized formulations were reconstituted in sterile water and samples stored in solution and lyophilized formulations were characterized by dynamic light scattering analysis.
Figure 6B:
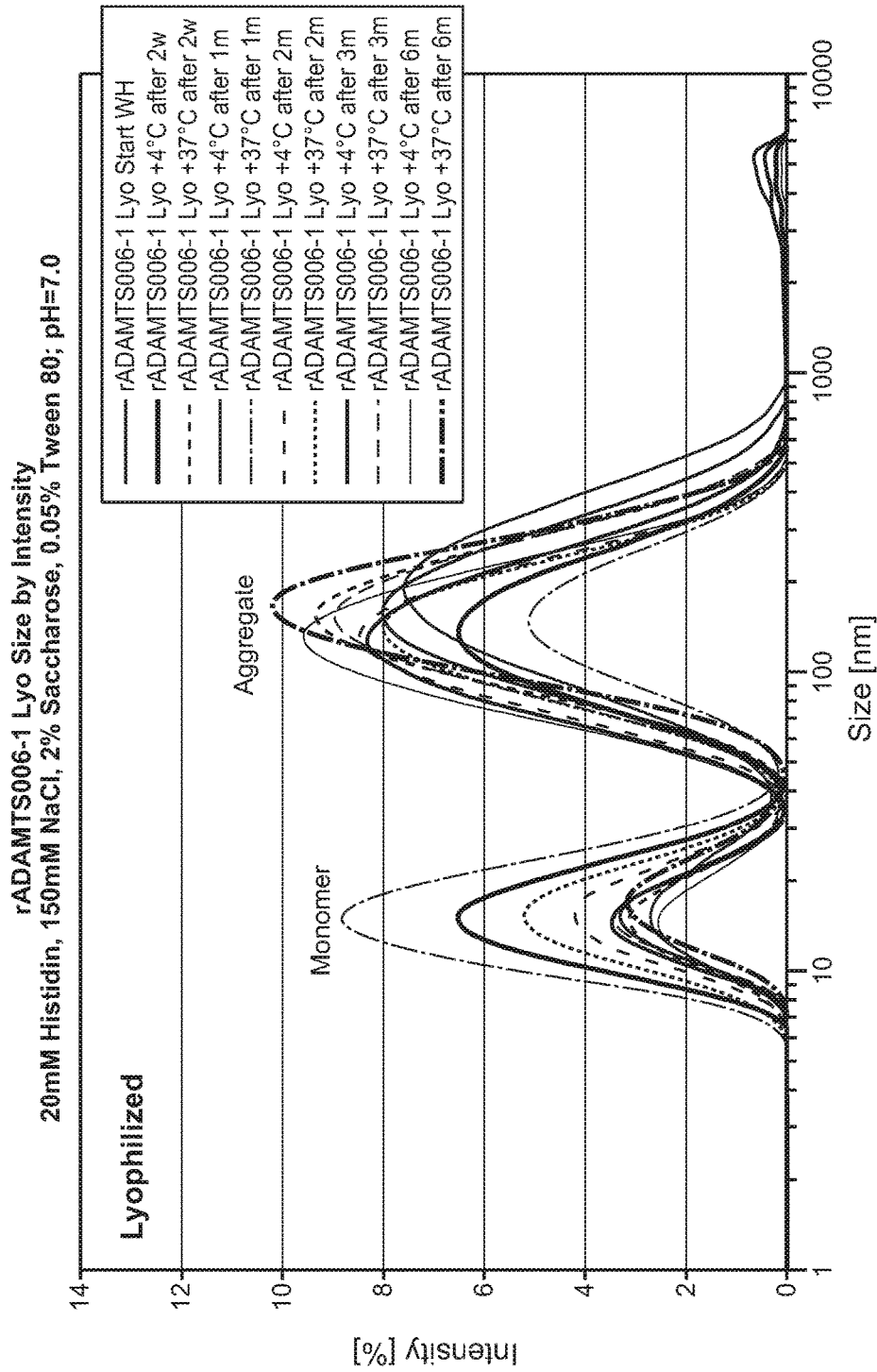
Figure 7A:
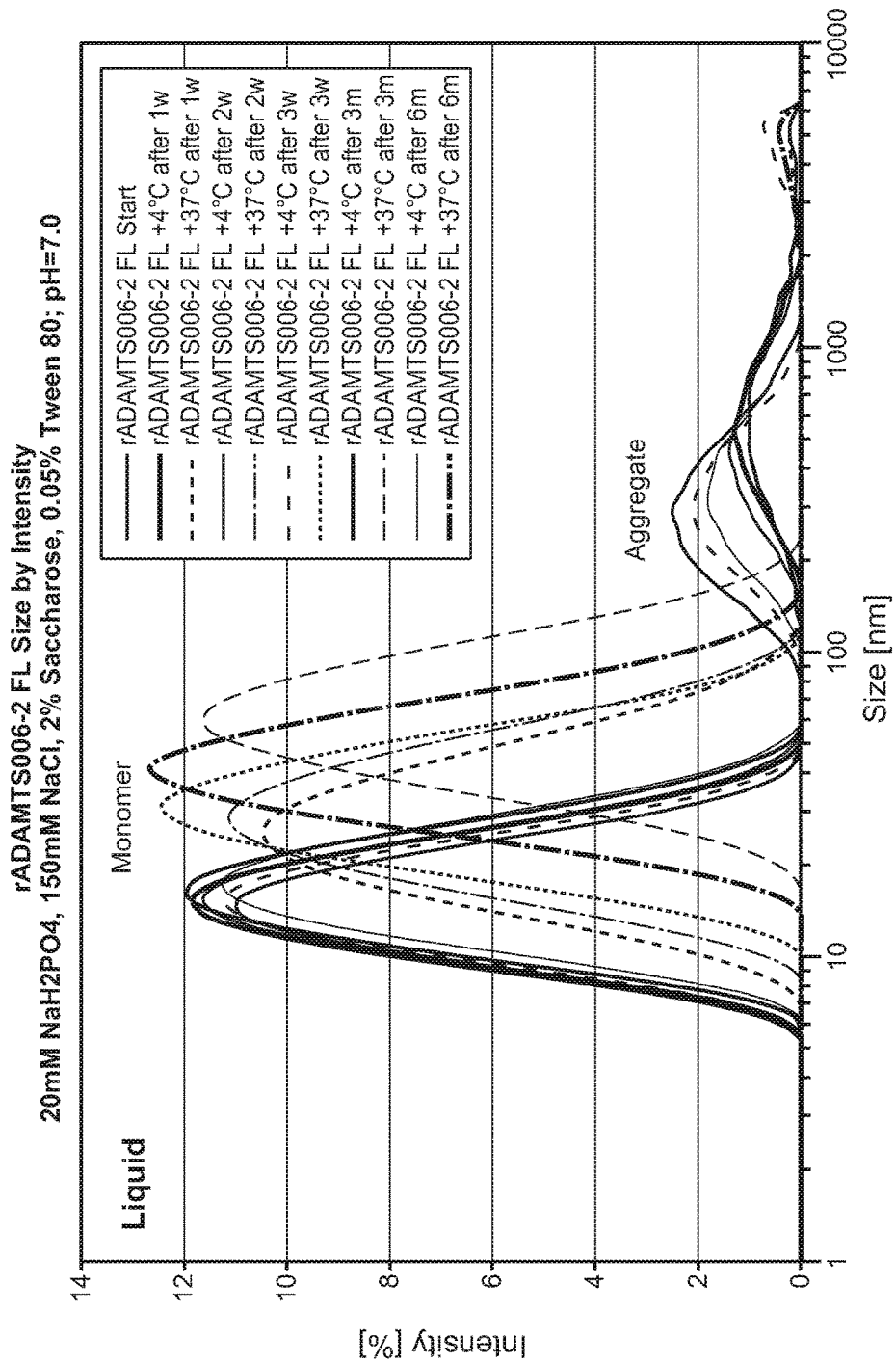
FIGS. 7A and 7B. Recombinant ADAMTS13 was formulated in buffer containing 150 mM NaCl, 2% sucrose, 0.05% polysorbate 80, and 20 mM sodium phosphate buffer at pH 7.0 and then stored (A) in solution or (B) lyophilized at 4° C. or 37° C. for up to 6 months. Lyophilized formulations were reconstituted in sterile water and samples stored in solution and lyophilized formulations were characterized by dynamic light scattering analysis.
Figure 7B:
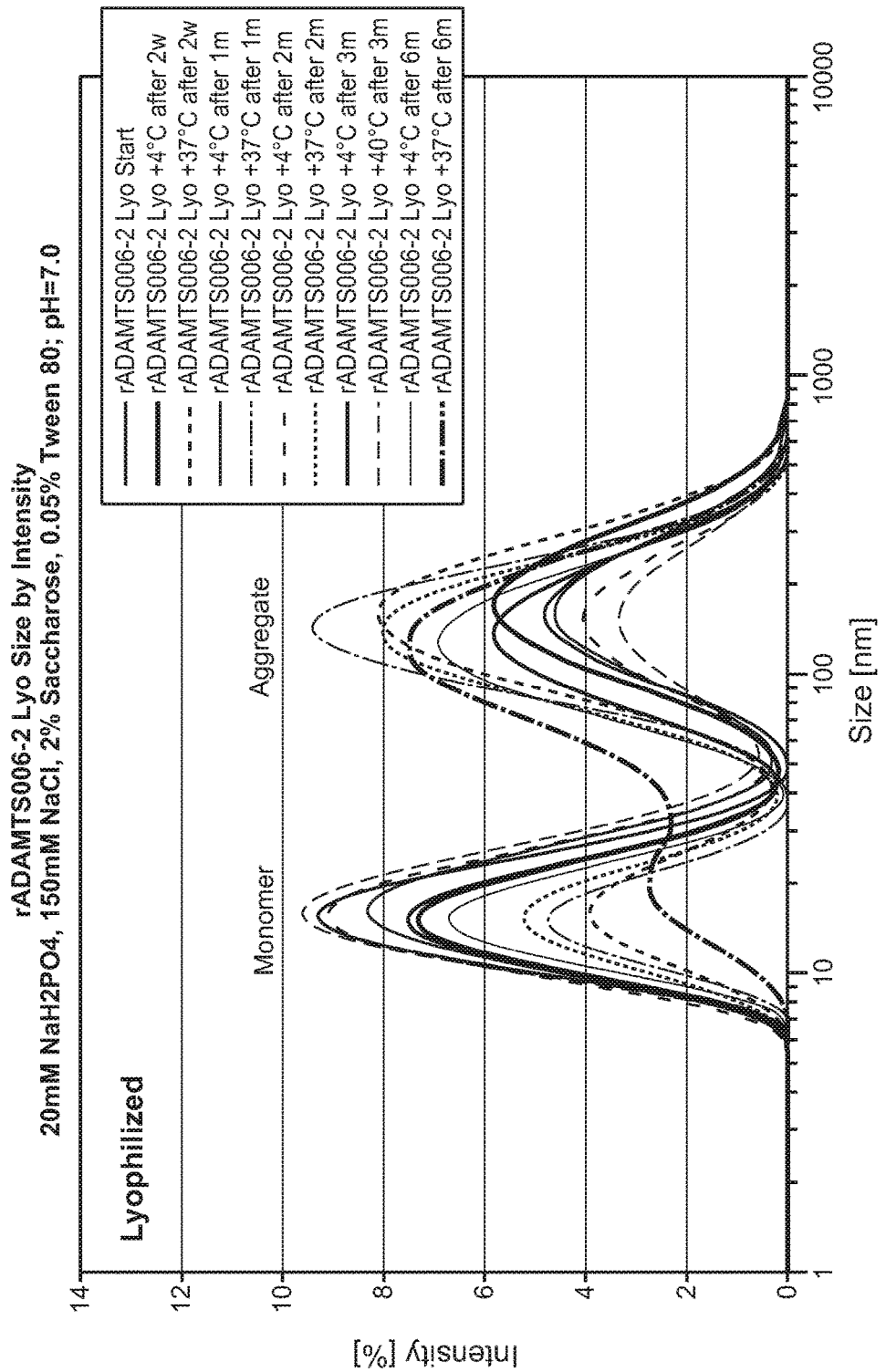
Figure 8A:
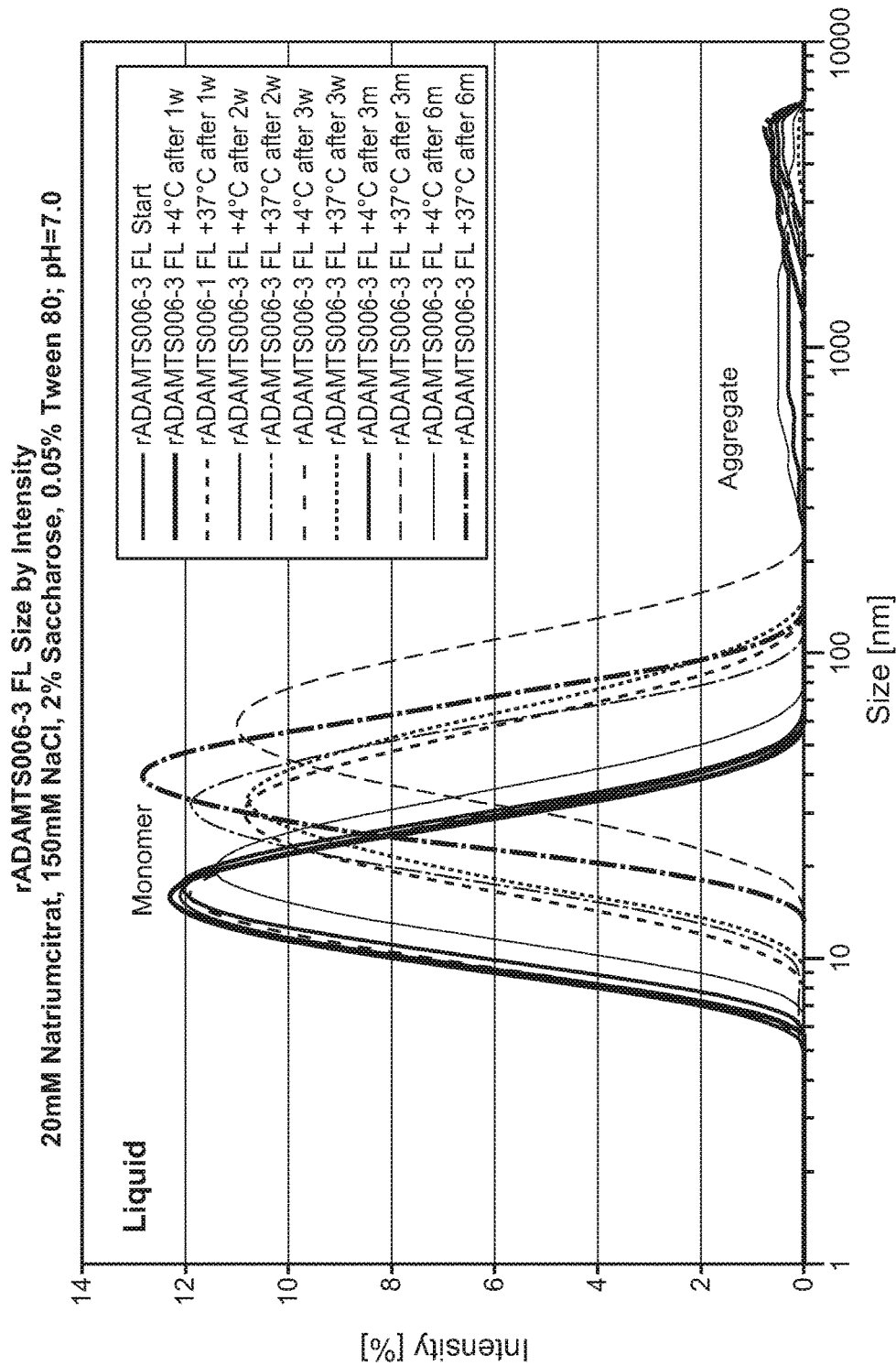
FIGS. 8A and 8B. Recombinant ADAMTS13 was formulated in buffer containing 150 mM NaCl, 2% sucrose, 0.05% polysorbate 80, and 20 mM tri-sodium citrate at pH 7.0 and then stored (A) in solution or (B) lyophilized at 4° C. or 37° C. for up to 6 months. Lyophilized formulations were reconstituted in sterile water and samples stored in solution and lyophilized formulations were characterized by dynamic light scattering analysis.
Figure 8B:
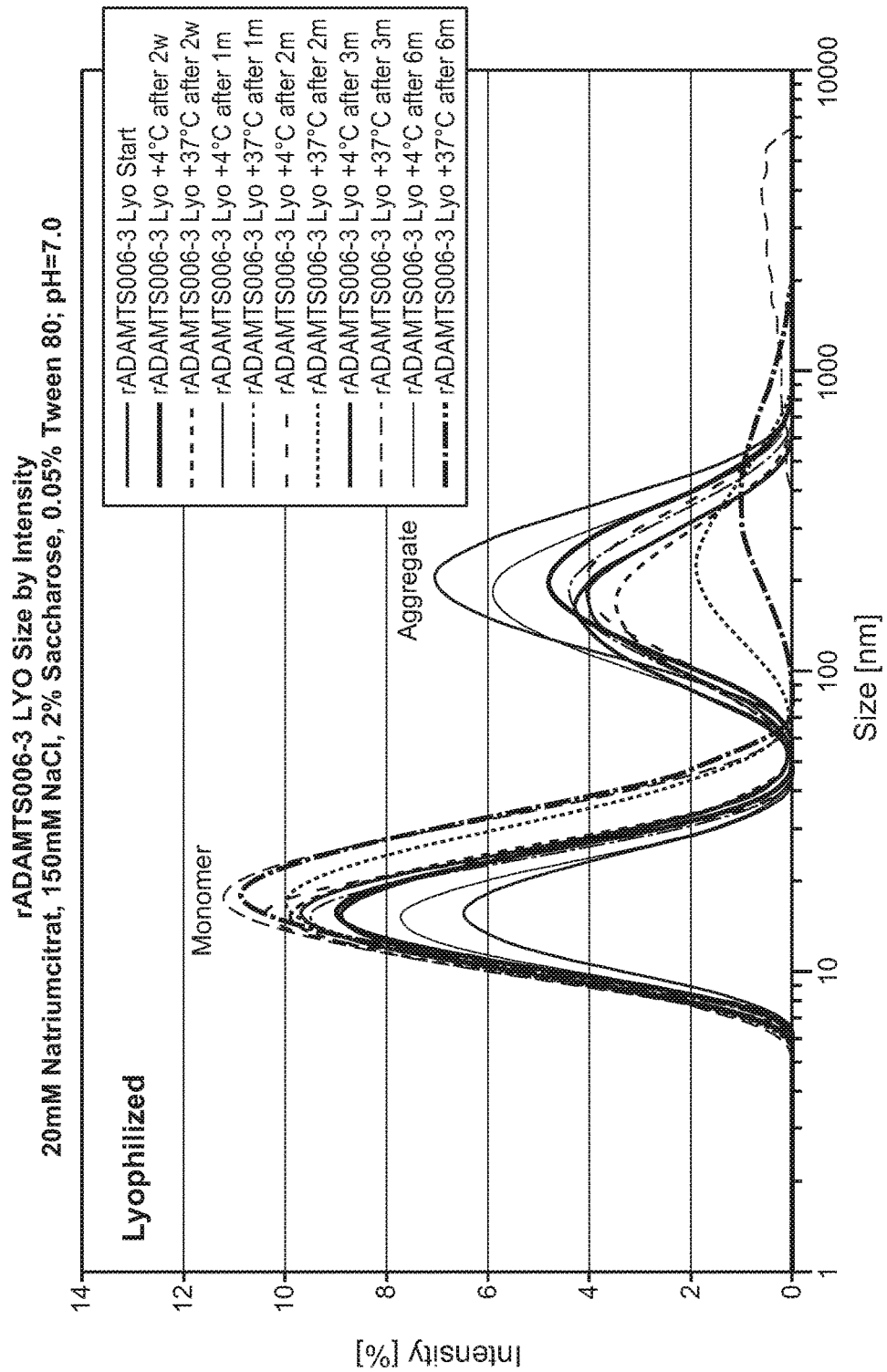

E. Example 5: Biophysical Characterization of rA13 Formulations Stored at 4° C. and 37° C.

rA13 samples formulated and aliquoted as in example 2 were stored at either 4° C. or 37° C. for up to 6 months time. As a measure of the conformational stability of rA13 protein formulated as described above, stokes radii were determined by dynamic light scattering for the solution (A) and lyophilized (B) rA13 formulations with histidine (FIG. 6), phosphate buffer (FIG. 7), and sodium citrate (FIG. 8), at each of the indicated time points.

Furthermore, derived count rates for each of the liquid formulation, before storage, were determined by dynamic light scattering. As can be seen in FIG. 12, there is a discontinuity in the change of the stokes radii, and thus rA13 stability, above about 35° C. for the histidine and sodium citrate formulations, and above about 40° C. for the phosphate formulation. Furthermore, although the phosphate formulation has a larger stokes radius than the histidine or sodium citrate formulations at temperatures below about 37° C., the phosphate formulation appears to be slightly more stable at temperatures between about 40° C. and 50° C.

Figure 9:
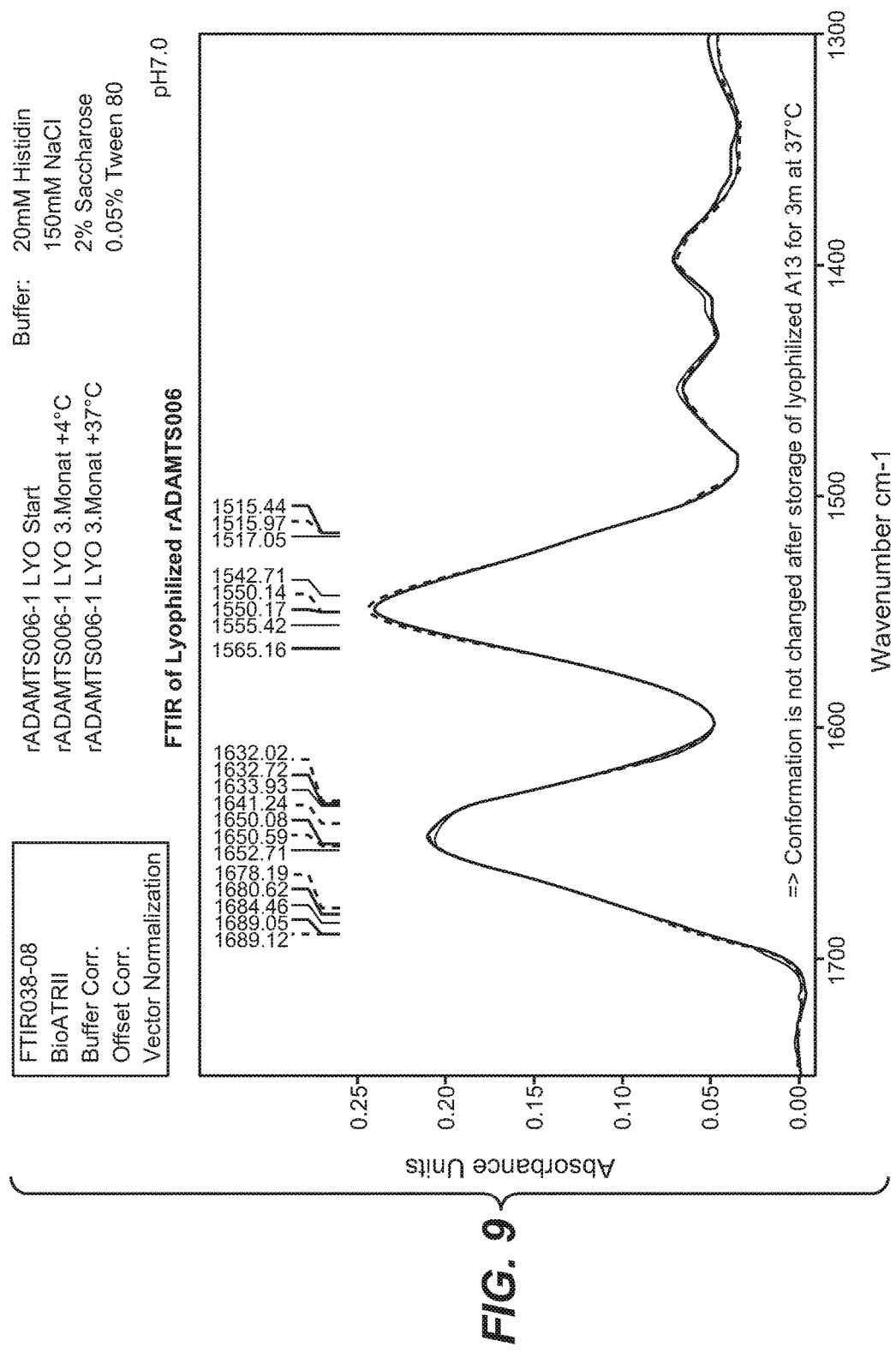
FIG. 9. Recombinant ADAMTS13 was formulated in buffer containing 150 mM NaCl, 2% sucrose, 0.05% polysorbate 80, and 20 mM histidine at pH 7.0 and then lyophilized. Lyophilized samples were stored at 4° C. or 37° C. for 3 months, and then reconstituted in sterile water. ADAMTS13 samples were then characterized by fourier transform infrared spectroscopy and the results were compared to freshly formulated and lyophilized sample.
Figure 10:
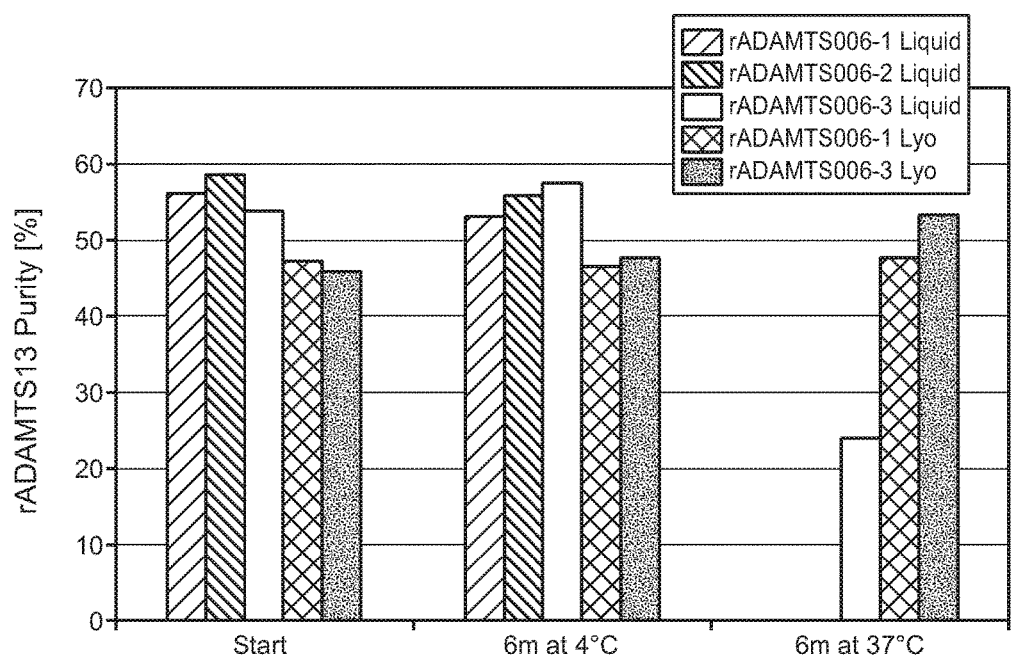
FIG. 10. Recombinant ADAMTS13 was formulated in buffer containing 150 mM NaCl, 2% sucrose, 0.05% polysorbate 80, at a pH of 7.0 with 20 mM of a buffering agent selected from (1) histidine, (2) phosphate buffer, or (3)

Lyophilized samples formulated with histidine were stored at 4° C. or 37° C. for 3 months, and then reconstituted in sterile water. In order to characterize whether or not local or global conformational changes occurred in reconstituted rA13, fourier transform infrared spectroscopy was performed for the samples stored at 4° C. and 37° C. for 3 months, and compared to freshly formulated and lyophilized A13. As can be seen in FIG. 9, the absorbance spectrums for all three samples overlay nearly perfectly, suggesting that no conformational transitions are occurring in rA13 stored as a lyophilized formulation in histidine at 4° C. or 37° C. for 3 months.

rA13 formulations stored at 4° C. or 37° C. for 6 months were also characterized by reverse phase-high-performance liquid chromatography (rp-HPLC). rp-HPLC allows for the separation of closely related protein molecules and thus in many instances can differentiate between modified versions of the same polypeptide, e.g. charge-modified, partially-degraded, or partially-unfolded. As can be seen in FIG. 10, all rA13 formulations appear to be stable for at least 6 months at 4° C., consistent with several results seen above.

rA13 samples formulated as in example 2 were next analyzed by differential scanning calorimetry to further characterize the stability of the rA13 protein in the various formulations. The bimodal nature of the heat capacity curve generated in FIG. 11, suggests that two domains of the protein may unfold separate of each other, with the first unfolding transition occurring at a temperature between about 54° C. and 55° C. The unfolding temperatures for rA13 are similar for the various formulations. However, the increased enthalpy of transition, as indicated by the larger area beneath the endotherm, for the phosphate formulation, and to a lesser extent the citrate formulation, suggest slightly stabilized formulations of A13.

F. Example 6: Characterization of Dimer Formation in rA13 Formulations

In order to determine the effect of stabilizing agents on the oligomeric state of rA13 in solution, rA13 was formulated in 20 mM histidine (pH 7.0), 150 mM NaCl, and 0.05% polysorbate 80 with different combinations of sucrose (0% to 2%), mannitol (0% to 3%), and calcium (0 mM or 2 mM). The various formulations were then analyzed by gel filtration over a Sepharose 6 GL column (GE Healthcare). As seen in FIG. 13, various combinations of the stabilizing agents were able to reduce the amount of A13 dimer formation by about 50%. The percentages of aggregates, dimers/oligos, and monomers for each formulation is provided in Table 14.

TABLE 14

Formulations used to determine the effect of various buffering agents of the formulation of ADAMTS13.

| Lot | $CaCl_2$ [mM] | Sucrose [g/l] | Mannitol [g/l] | Aggregate [%] | Dimer/Oligomer [%] | Monomer [%] |
|---|---|---|---|---|---|---|
| rADAMTS008-1 | — | 10 | 20 | 0.854 | 46.34 | 53.04 |
| rADAMTS008-2 | 2 | 10 | 20 | 1.664 | 42.08 | 56.94 |
| rADAMTS008-3 | — | 10 | — | 1.932 | 50.54 | 48.16 |
| rADAMTS008-4 | 2 | 10 | — | 1.979 | 41.57 | 57.14 |
| rADAMTS008-5 | — | 10 | 10 | 1.820 | 49.8 | 49.13 |
| rADAMTS008-6 | 2 | 10 | 10 | 1.748 | 40.98 | 58.01 |
| rADAMTS008-7 | — | 10 | 30 | 1.645 | 47.07 | 51.88 |
| rADAMTS008-8 | 2 | 10 | 30 | 2.242 | 41.23 | 57.33 |
| rADAMTS008-9 | — | — | — | 1.540 | 51.62 | 47.39 |
| rADAMTS008-10 | 2 | — | — | 1.429 | 39.49 | 59.62 |
| rADAMTS008-11 | — | — | 20 | 1.496 | 45.7 | 53.41 |
| rADAMTS008-12 | 2 | — | 20 | 1.428 | 39.93 | 59.18 |
| rADAMTS008-13 | — | 20 | — | 2.083 | 48.13 | 50.56 |
| rADAMTS008-14 | 2 | 20 | — | 1.997 | 41.43 | 57.34 |
| rADAMTS008-15 | — | 20 | 20 | 1.904 | 46.77 | 52.06 |
| rADAMTS008-16 | 2 | 20 | 20 | 1.866 | 41.66 | 57.2 |
| rADAMTS008-17 | — | 20 | 30 | 1.956 | 45.97 | 52.81 |
| rADAMTS008-18 | 2 | 20 | 30 | 2.126 | 41.68 | 57.07 |

G. Example 7: Effect of pH on ADAMTS13 Formulation Stability

In order to determine the effect of pH on the stability of rA13 in solution, rA13 was dialyzed into buffer containing 20 mM histidine and 150 mM NaCl, adjusted to a range of pH's between 5.5 and 9.5, and stored at either 4° C. or 40° C. for 24 hours. Stability was measured by rA13 antigen concentration, as determined by ELISA, and rA13 activity by FRETS-VWF73 assay, at 24 hours. As seen in Table 3 and FIG. 14, rADAMTS13 is relatively stable for 24 hours at 4° C. when formulated in a solution having a pH between 5.5 and 9.5.

TABLE 3

ADAMTS13 stability in liquid formulation when stored at 4° C. for 24 hours.

| rADAMTS003 | FRETS 5012-02-0552 | | ADAMTS:Antigen 5016-01-0351 | |
|---|---|---|---|---|
| | [U/ml] | [%] | [U/ml] | [%] |
| Starting material | 260792 | 100% | 2208 | 100% |
| pH 5.5 | 216356 | 83% | 1468 | 66% |
| pH 6.5 | 399216 | 153% | 2042 | 92% |
| pH 7.5 | 358512 | 137% | 2178 | 99% |
| pH 8.5 | 176649 | 68% | 2179 | 99% |
| pH 9.5 | 110622 | 51% | 1696 | 77% |

TABLE 4

ADAMTS13 stability in liquid formulation when stored at 40° C. for 24 hours.

| rADAMTS002 | FRETS Prot: 5012-02-0297 | | ADAMTS:Antigen 5016-01-0297 | |
|---|---|---|---|---|
| | [U/ml] | [%] | [U/ml] | [%] |
| Starting Material | 281855 | 100% | 1825 | 100% |
| pH 5.5 | 4264 | 2% | 1225 | 67% |
| pH 6.5 | 12111 | 4% | 1836 | 101% |
| pH 7.5 | 7190 | 3% | 2106 | 115% |
| pH 8.5 | 4729 | 2% | 1455 | 80% |
| pH 9.5 | <2500 | | 1437 | 79% |

H. Example 8: Effect of Low Levels of $CaCl_2$ on ADAMTS13 Formulation Stability In order to determine the effect of low levels of $CaCl_2$ on the stability of rA13 in solution, rA13 was formulated in buffer containing 150 mM NaCl, 2% sucrose, 0.05% polysorbate 80, and 20 mM histidine at pH 7.0 with (12B and D) and without (12A and C) 2 mM $CaCl_2$. The liquid formulations were stored at either 25° C. or 37° C. for three weeks. Stability of the formulation was then assessed by determining the relative FRETS-VWF73 activity at 0, 1, 2, and 3 weeks. As can be seen in FIG. 15, the addition of 2 mM $CaCl_2$ stabilized liquid rADAMTS13 formulations stored at both 25° C. and 37° C., to varying degrees. Notably, addition of low levels of $CaCl_2$ to rADAMTS13 liquid formulations stored at 25° C. conferred about 95% enzyme activity stability for three weeks, as compared to an 80% loss of activity seen in formulations without $CaCl_2$.

I. Example 9: FRETS-VWF73 Activity of Oligomeric Species of Recombinant ADAMTS13

In order to determine the enzymatic activity of the different oligomeric species of ADAMTS13 protein isolated during purification, rA13 was loaded onto a Superose 6 GL gel filtration column equilibrated with a buffer containing 20 mM $Na_2HPO_4$ (pH 7.5) and 500 mM NaCl. ADAMTS13 molecular species were then separated by size and shape. Fractions eluting from the column were pooled according to their apparent oligomeric state, e.g. aggregated A13 (Pool 1), dimeric A13 (Pool 2), and monomeric A13 (Pool 3) (FIG. 16A). Further confirmation of the oligomeric state of ADAMTS13 was obtained by determining the average stokes radius of the protein in each pool by dynamic light scattering (FIG. 16B).

The enzymatic activity of each pool was then determined by FRETS-VWF73 assay. As can be seen in FIG. 16, the volumetric activity of the aggregated A13 species was about 218 mU/ml, the activity of dimeric A13 was about 1.435 U/ml, and the activity of the monomeric A13 was about 97.905 U/ml. After standardizing the activities for the volume of the pools, greater than 99% of the total activity is found in the elution pool corresponding to the monomeric protein. When the activities are then standardized for the total amount of protein, it can be seen that the monomeric protein pool has a higher specific activity than both the dimeric protein pool and the aggregated protein pool.

Figure 17A:
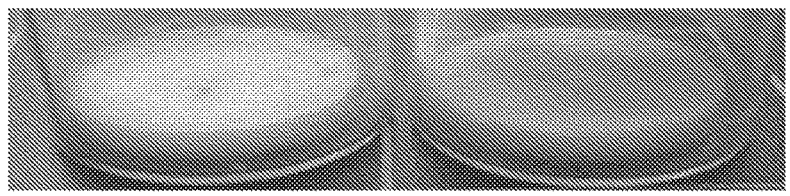
Figure 17B:
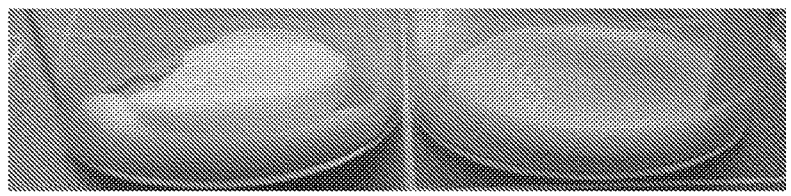
Figure 17C:
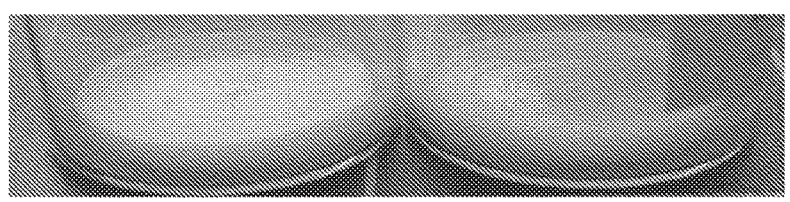
Figure 17D:
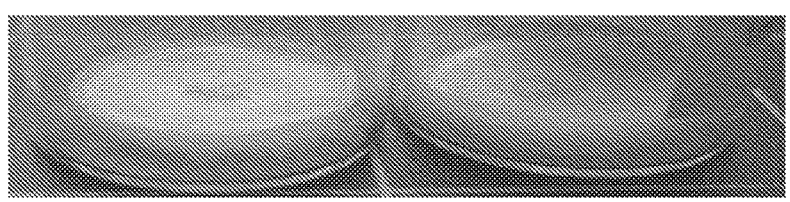
Figure 17E:
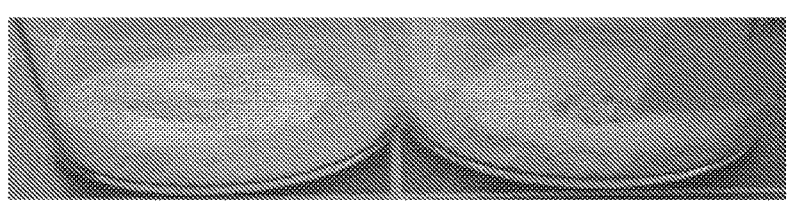
Figure 17F:
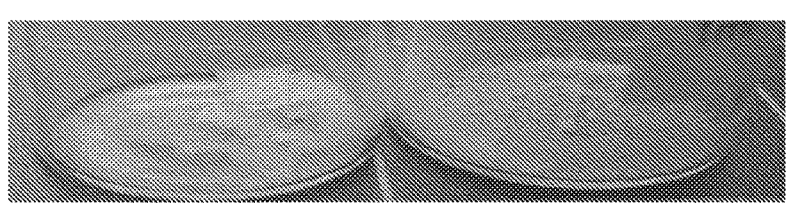

J. Example 10: Effect of NaCl Concentration on the Lyophilization of ADAMTS13 Formulations In order to determine the effect of NaCl concentration on the production of lyocakes, recombinant ADAMTS13 was formulated in buffer containing 2% sucrose, 0.05% polysorbate 80, and 20 mM histidine (pH 7.0) with varying amounts of NaCl (0 to 150 mM). The ADAMTS13 formulations were then lyophilized under standard conditions and visually inspected for the quality of the resulting lyocakes (FIG. 17). Lyocakes produced from ADAMTS13 formulations containing lower salt concentrations (0 to 60 mM; FIGS. 17A-C) had compact structures with smooth surfaces, while lyocakes produced from high salt formulations (120 mM and 150 mM NaCl; FIGS. 17 E and F) were porous and not compact, with a string-like or cracked appearance. ADAMTS13 formulations containing intermediate levels of NaCl (90 mM; FIG. 17D) were partially compact with a semi-porous or crater-like surface.

A porous, non-compact lyocake indicates melting during the lyophilization process. Generally, high salt concentrations are used to decrease the collapse temperature (or glass temperature) that can result in the partial melting of the frozen material during the primary drying process. This can have a negative impact on protein aggregation levels and/or the recovery of enzymatic activity. Therefore, a good lyocake appearance usually correlates with better recovery of activity and less aggregation of the respective formulated protein. Advantageously, the present invention provides ADAMTS13 formulations which allow for the production of high quality lyocakes. In certain embodiments, the inventive formulations provided herein allow for low salt formulations of ADAMTS13, that are particularly stable during lyophilization, resulting in the formation of high quality lyocakes.

One concern with the use of low salt protein formulations is that increased protein aggregation may occur. To determine if this was the case for the low salt ADAMTS13 formulations, the lyocakes produced above were reconstituted in de-ionized water and the aggregation states of the reconstituted ADAMTS13 proteins were analyzed by size exclusion chromatography. As can be seen in FIG. 18, the salt concentration of the lyophilized formulations had no effect on the aggregation state of reconstituted ADAMTS13 protein (compare 0 mM NaCl with 150 mM NaCl).

To further validate the use of low salt ADAMTS13 formulations, the FRETS-VWF73 activity of various formulations ranging from 0 to 150 mM NaCl was determined. As can be seen in FIG. 19, the salt concentration, as well as the sucrose concentration, of the ADAMTS13 formulations did not influence the activity of the recombinant ADAMTS13 protein. These results suggest that low salt (i.e. 0 to 100 mM NaCl) formulations of liquid and lyophilized recombinant ADAMTS13 proteins are well suited for pharmaceutical use.

K. Example 11: Lyophilized Formulation of ADAMTS13 in High Salt and Low Salt Buffers To compare lyophilized formulations of recombinant ADAMTS13, high salt (150 mM NaCl) and low salt (30 mM NaCl) formulations were prepared. Both the high salt and low salt formulations contained 20 mM histidine (pH 7.0), 150 mM NaCl, 0.05% polysorbate 80, and 2 mM $CaCl_2$. The high salt formulation further contained 2% sucrose and 150 mM NaCl, while the low salt formulation further contained 1% sucrose, 3% mannitol, and 30 mM NaCl. The two formulations were then lyophilized under standard conditions. The resulting lyocake produced from the high salt ADAMTS13 formulation was not compact, non-uniform, clumpy, and porous (FIG. 20A), while the lyocake produced from the low salt ADAMTS13 formulation was compact, fairly uniform, and had a smooth surface (FIG. 20B). These results suggest that low salt formulations of lyophilized ADAMTS13 are well suited for pharmaceutical use.

L. Example 12: Purification of rADAMTS13 for Lyophilized Formulations

Recombinant ADAMTS13 was expressed in recombinant CHO cells and purified from the resulting conditioned media by POROS HS cation exchange chromatography. Collected fractions of rADAMTS13 eluted off of the HS column were then analyzed, by size exclusion chromatography using a superose 6 GL: TC10/30 column, for dimerization and aggregation prior to and after gel filtration, by size exclusion chromatography (FIGS. 21A and B, respectively) and dynamic light scattering (FIGS. 22A and B, respectively). As can be seen in FIG. 21A, nearly 20% of the total rADAMTS13 in the HS-eluted fractions, prior to gel filtration, were in undesirable dimeric, monomeric, or aggregated states. In contrast, almost all of the rADAMTS13 pooled from the gel filtration step is monomeric (FIG. 21B). Similarly, the average hydrodynamic radius of the HS-eluted rADAMS13 (about 20.5 nm; FIG. 22A) was nearly twice that of the rADAMTS recovered after size exclusion chromatography (about 12-13 nm; FIG. 22B)

M. Example 13: Comparison of Standard and Extended Protocols for Lyophilization of rADAMTS13 Formulations In order to compare lyophilization of rADAMTS13 formulations containing variable low salt (30 mM and 60 mM NaCl), calcium (2 mM and 4 mM $CaCl_2$), and sugar (1% sucrose and 1% trehalose) concentrations, rADAMTS13 was purified by cation exchange chromatography and size exclusion chromatography, as above, and formulated in 20 mM histidine, 3% mannitol, 0.05% polysorbate 80, with all eight combinations of salt, calcium, and sugar given above. All vials had the same concentration of ADAMTS13 (190 μg/mL antigen). rA13 formulations 1 to 8 (Tables 5 and 6) were then lyophilized using either a standard (3 days; FIG. 23A) or extended (11 days; FIG. 23B) lyophilization protocol. After lyophilization, the lyocakes were visually inspected for desirable qualities (FIG. 24).

TABLE 5

Lyophilized rADAMTS13 formulations used in standard lyophilization protocol.

| rA13 Formulation (A LYO) | NaCl (mM) | Histidine (mM) | CaCl₂ (mM) | Mannitol (%) | Sucrose (%) | Trehalose (%) | Tween 80 (%) | Optical Evaluation |
|---|---|---|---|---|---|---|---|---|
| 1 | 30 mM | 20 mM | 2 mM | 3% | 1% | — | 0.050% | Beautiful, compact lyocake; smooth surface detached from wall |
| 2 | 30 mM | 20 mM | 2 mM | 3% | — | 1% | 0.050% | Same as variant 1 |
| 3 | 30 mM | 20 mM | 4 mM | 3% | 1% | — | 0.050% | Same as variant 1 |
| 4 | 30 mM | 20 mM | 4 mM | 3% | — | 1% | 0.050% | Same as variant 1 |
| 5 | 60 mM | 20 mM | 2 mM | 3% | 1% | — | 0.050% | Beautiful, compact lyocake; smooth surface, periphery porous and easily detached from wall |
| 6 | 60 mM | 20 mM | 2 mM | 3% | — | 1% | 0.050% | Same as variant 5; surface easily detached from lyocake |
| 7 | 60 mM | 20 mM | 4 mM | 3% | 1% | — | 0.050% | Same as variant 5; periphery pulverulent/flocculent |
| 8 | 60 mM | 20 mM | 4 mM | 3% | — | 1% | 0.050% | Same as variant 5; surface detached from lyocake; periphery pulverulent |

TABLE 6

Lyophilized rADAMTS13 formulations used in extended lyophilization protocol.

| rA13 Formulation (B LYO) | NaCl (mM) | Histidine (mM) | CaCl₂ (mM) | Mannitol (%) | Sucrose (%) | Trehalose (%) | Tween 80 (%) | Optical Evaluation |
|---|---|---|---|---|---|---|---|---|
| 1 | 30 mM | 20 mM | 2 mM | 3% | 1% | — | 0.050% | Beautiful, compact lyocake; smooth surface broken from periphery |
| 2 | 30 mM | 20 mM | 2 mM | 3% | — | 1% | 0.050% | Same as variant 1 |
| 3 | 30 mM | 20 mM | 4 mM | 3% | 1% | — | 0.050% | Same as variant 1 |
| 4 | 30 mM | 20 mM | 4 mM | 3% | — | 1% | 0.050% | Same as variant 1 |
| 5 | 60 mM | 20 mM | 2 mM | 3% | 1% | — | 0.050% | Same as variant 1 |
| 6 | 60 mM | 20 mM | 2 mM | 3% | — | 1% | 0.050% | Same as variant 1 |

TABLE 6-continued

Lyophilized rADAMTS13 formulations used in extended lyophilization protocol.

| rA13 Formulation (B LYO) | NaCl (mM) | Histidine (mM) | CaCl$_2$ (mM) | Mannitol (%) | Sucrose (%) | Trehalose (%) | Tween 80 (%) | Optical Evaluation |
|---|---|---|---|---|---|---|---|---|
| 7 | 60 mM | 20 mM | 4 mM | 3% | 1% | — | 0.050% | Beautiful, compact lyocake; porous surface broken from wall; periphery flocculent |
| 8 | 60 mM | 20 mM | 4 mM | 3% | — | 1% | 0.050% | Same as variant 1; surface broken |

To determine the multimeric state of ADAMTS13 in each of the formulations, lyophilized protein was reconstituted in deionized water and analyzed by dynamic light scattering. As can be seen in FIG. 25, lyophilized formulations prepared by using both standard and extended lyophilization protocols, yielded primarily monomeric ADAMTS13 molecules (peak at about 12-13 nm) after reconstitution. Although the ADAMTS13 peak corresponding to aggregated protein (between 100 and 110 nm) appears to be about half as high as the monomer peak, one of ordinary skill will recognize that the y-axis is measuring intensity, rather than total mass, and as such the graph greatly exaggerates the percentage of ADAMTS13 species that are aggregated. It is also seen that formulations prepared with extended lyophilization protocols (dashed lines) contain less aggregated ADAMTS13 than formulations prepared with standard lyophilization protocols (unbroken lines), after reconstitution in deionized water.

In order evaluate the stability of the lyophilized rADAMTS13 in each of the formulations presented above, the lyocakes produced by the standard and extended protocols were used to prepare a series of vials for storage under various temperatures for up to 36 months. As outlined in Table 7, vials containing either 5 mg or 10 mg lyophilized rADAMTS13 were prepared for storage at +2-+8° C. (i.e. under standard refrigeration conditions), 30° C. (room temperature), and 40° C. All vials were tested by FTIR, SE-HPLC and DLS. Also FRETS activity and ADAMTS13 antigen were tested for all samples. Lyophilized ADAMTS13 formulations can then be tested for FRETS-VWF73 activity and antigen stability, as outlined above, at the indicated time points to determine the stability of the protein in the various lyophilized formulations. Tables 8 and 9 provide the results of FRETS-VWF73 activity assays of reconstituted ADAMTS13 formulations generated by the standard and extended lyophilization protocols, respectively. Similarly, antigen recovery is given in tables 10 and 11, for samples generated with the standard and extended lyophilization protocols, respectively.

TABLE 7

Experimental set-up for testing the stability of lyophilized ADAMTS13 formulations. Set-up corresponds to both A and B type lyophilizations.

| | buffer | 0 M | 1 M | 2 M | 3 M | 4 M | 6 M | 9 M | 12 M | 15 M | 18 M | 24 M | 30 M | 36 M |
|---|---|---|---|---|---|---|---|---|---|---|---|---|---|---|
| -1B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |
| -2B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |
| -3B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |
| -4B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |
| -5B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |
| -6B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |
| -7B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |

TABLE 7-continued

Experimental set-up for testing the stability of lyophilized ADAMTS13 formulations.
Set-up corresponds to both A and B type lyophilizations.

| | buffer | Vial | | | | | | | | | | | | |
|---|---|---|---|---|---|---|---|---|---|---|---|---|---|---|
| | | 0 M | 1 M | 2 M | 3 M | 4 M | 6 M | 9 M | 12 M | 15 M | 18 M | 24 M | 30 M | 36 M |
| -8B | -80° C. | 30 | | | | | | | | | | | | |
| | +2-+8° C. | 20 | | | 10 | 5 | 5 | 5 | 5 | 5 | 5 | 5 | 5 | 5 |
| | RT | | | 5 | 10 | 5 | 5 | 5 | 5 | | | | | |
| | 40° C. | | 5 | 5 | 10 | 5 | 5 | | | | | | | |

TABLE 8

FRETS-VWF73 activity in lyophilized ADAMTS13 formulations prepared by standard lyophilization protocols.

| | | [U/ml] [%] 0 M | | | | [U/ml] [%] 1 M | | [U/ml] [%] 2 M | | [U/ml] [%] 3 M | | [U/ml] [%] 4 M | | [U/ml] [%] 6 M | | [U/ml] [%] 9 M | |
|---|---|---|---|---|---|---|---|---|---|---|---|---|---|---|---|---|---|
| | | | WH | | MW | WH | | | | | | | | | | | |
| -1A | 4° C. | 126 | 88 | 107 | 100% | — | — | — | — | 107.90 | 86% | 106.00 | 84% | 108.40 | 86% | 104.90 | 83% |
| | 30° C. | | | | | — | — | 105 | 83% | 100.70 | 80% | 95.30 | 76% | 95.70 | 76% | 99.10 | 79% |
| | 40° C. | | | | | 98 | 92% | 127 | 100% | 81.50 | 65% | 86.70 | 69% | 88.40 | 70% | — | — |
| -2A | 4° C. | 101 | 100 | 101 | 100% | — | — | — | — | 99.4 | 98% | 99.7 | 98% | 98.2 | 97% | 101.2 | 100% |
| | 30° C. | | | | | — | — | 98 | 97% | 100.1 | 99% | 93 | 92% | 92.1 | 91% | 99.3 | 98% |
| | 40° C. | | | | | 99 | 98% | 95 | 94% | 93.3 | 92% | 93.5 | 92% | 83.3 | 82% | — | — |
| -3A | 4° C. | 117 | 119 | 118 | 100% | — | — | — | — | 101.9 | 87% | 99.1 | 84% | 104.4 | 89% | 105.8 | 90% |
| | 30° C. | | | | | — | — | 105 | 90% | 97.9 | 83% | 94.1 | 80% | 93.5 | 80% | 98.5 | 84% |
| | 40° C. | | | | | 114 | 96% | 101 | 86% | 91.7 | 78% | 87.2 | 74% | 87 | 74% | — | — |
| -4A | 4° C. | 113 | 100 | 106 | 100% | — | — | — | — | 97.7 | 87% | 99.9 | 89% | 103 | 91% | 101.8 | 90% |
| | 30° C. | | | | | — | — | 107 | 95% | 97.9 | 87% | 91.9 | 82% | 90 | 80% | 96.5 | 86% |
| | 40° C. | | | | | 100 | 94% | 122 | 108% | 95.3 | 85% | 89.3 | 79% | 91.2 | 81% | — | — |
| -5A | 4° C. | 109 | 97 | 103 | 100% | — | — | — | — | 94.1 | 86% | 100.2 | 92% | 107.7 | 99% | 104.5 | 96% |
| | 30° C. | | | | | — | — | 125 | 115% | 93.9 | 86% | 91.6 | 84% | 89.2 | 82% | 98 | 90% |
| | 40° C. | | | | | 106 | 103% | 107 | 98% | 84.5 | 77% | 74.1 | 68% | 80.1 | 73% | — | — |
| -6A | 4° C. | 93 | 81 | 87 | 100% | — | — | — | — | 97.2 | 104% | 94.7 | 101% | 104.5 | 112% | 102.7 | 110% |
| | 30° C. | | | | | — | — | 103 | 111% | 94.4 | 101% | 91.5 | 98% | 91.6 | 98% | 97.3 | 104% |
| | 40° C. | | | | | 85 | 97% | 90 | 96% | 89.8 | 96% | 84.7 | 91% | 82 | 88% | — | — |
| -7A | 4° C. | 111 | 102 | 106 | 100% | — | — | — | — | 98.9 | 89% | 100.2 | 90% | 103 | 93% | 100.1 | 90% |
| | 30° C. | | | | | — | — | 105 | 94% | 90.6 | 82% | 89.4 | 81% | 85.2 | 77% | 94.4 | 85% |
| | 40° C. | | | | | 105 | 99% | 114 | 103% | 85.1 | 77% | 77.8 | 70% | 79.6 | 72% | — | — |
| -8A | 4° C. | 101 | 126 | 113 | 100% | — | — | — | — | 104 | 103% | 100.3 | 99% | 101.6 | 101% | 101.5 | 101% |
| | 30° C. | | | | | — | — | 126 | 125% | 89.6 | 89% | 92.9 | 92% | 94.2 | 93% | 92.8 | 92% |
| | 40° C. | | | | | 98 | 86% | 99 | 98% | 88.1 | 87% | 82.7 | 82% | 89.3 | 89% | — | — |

TABLE 9

FRETS-VWF73 activity in lyophilized ADAMTS13 formulations prepared by extended lyophilization protocols.

| | | [U/ml] [%] 0 M | | [U/ml] [%] 1 M | | [U/ml] [%] 2 M | | [U/ml] [%] 3 M | | [U/ml] [%] 4 M | | [U/ml] [%] 6 M | | [U/ml] [%] 9 M | |
|---|---|---|---|---|---|---|---|---|---|---|---|---|---|---|---|
| -1B | 4° C. | 112 | 100% | — | — | — | — | 101.70 | 91% | 102.40 | 92% | 105.60 | 95% | 100.70 | 90% |
| | 30° C. | | | | | 97 | 87% | 93.30 | 84% | 95.60 | 86% | 102.30 | 92% | 93.00 | 83% |
| | 40° C. | | | 108 | 97% | 97 | 87% | 101.40 | 91% | 96.80 | 87% | 86.10 | 77% | — | — |
| -2B | 4° C. | 104 | 100% | — | — | — | — | 93.9 | 91% | 99.1 | 96% | 107.3 | 104% | 98.8 | 95% |
| | 30° C. | | | | | 86 | 83% | 93.4 | 90% | 99.2 | 96% | 101.1 | 98% | 93.9 | 91% |
| | 40° C. | | | 106 | 102% | 87 | 84% | 104.2 | 101% | 94.2 | 91% | 92.5 | 89% | — | — |
| -3B | 4° C. | 111 | 100% | — | — | — | — | 91.7 | 83% | 101.2 | 92% | 105.1 | 95% | 103.8 | 94% |
| | 30° C. | | | | | 94 | 85% | 94.2 | 85% | 95 | 86% | 102.2 | 92% | 91.7 | 83% |
| | 40° C. | | | 98 | 88% | 108 | 98% | 102.6 | 93% | 92.7 | 84% | 94.6 | 86% | — | — |
| -4B | 4° C. | 135 | 100% | — | — | — | — | 91.8 | 68% | 97.6 | 72% | 102.9 | 76% | 100.5 | 74% |
| | 30° C. | | | | | 104 | 77% | 97.8 | 72% | 97.8 | 72% | 102.8 | 76% | 95.2 | 70% |
| | 40° C. | | | 87 | 64% | 100 | 74% | 98.6 | 73% | 92.6 | 68% | 83.8 | 62% | — | — |
| -5B | 4° C. | 111 | 100% | — | — | — | — | 86.2 | 78% | 97.8 | 88% | 107 | 97% | 95.5 | 86% |
| | 30° C. | | | | | 97 | 87% | 92.6 | 84% | 93.1 | 84% | 101 | 91% | 89.1 | 80% |
| | 40° C. | | | 85 | 77% | 82 | 74% | 98.2 | 89% | 82.6 | 75% | 78 | 70% | — | — |
| -6B | 4° C. | 116 | 100% | — | — | — | — | 88.8 | 77% | 99.2 | 86% | 105.2 | 91% | 101.5 | 88% |
| | 30° C. | | | | | 90 | 78% | 97.5 | 84% | 100.2 | 87% | 102.9 | 89% | 91.4 | 79% |
| | 40° C. | | | 95 | 83% | 93 | 80% | 100.8 | 87% | 85.8 | 74% | 81.4 | 70% | — | — |

TABLE 9-continued

FRETS-VWF73 activity in lyophilized ADAMTS13 formulations prepared by extended lyophilization protocols.

| | | [U/ml] 0 M | [%] | [U/ml] 1 M | [%] | [U/ml] 2 M | [%] | [U/ml] 3 M | [%] | [U/ml] 4 M | [%] | [U/ml] 6 M | [%] | [U/ml] 9 M | [%] |
|---|---|---|---|---|---|---|---|---|---|---|---|---|---|---|---|
| -7B | 4° C. | 136 | 100% | — | — | — | — | 85.8 | 63% | 96.6 | 71% | 102.6 | 76% | 98 | 72% |
| | 30° C. | | | — | — | 97 | 71% | 94.1 | 69% | 95.7 | 71% | 97.9 | 72% | 88.8 | 66% |
| | 40° C. | | | 90 | 66% | 93 | 69% | 98.8 | 73% | 84.4 | 62% | 79.8 | 59% | — | — |
| -8B | 4° C. | 119 | 100% | — | — | — | — | 88.3 | 74% | 93.1 | 78% | 100.1 | 84% | 98.8 | 83% |
| | 30° C. | | | — | — | 108 | 91% | 95.7 | 80% | 95.4 | 80% | 101 | 85% | 93.7 | 79% |
| | 40° C. | | | 106 | 89% | 88 | 74% | 102.5 | 86% | 89.4 | 75% | 80.5 | 67% | — | — |

TABLE 10

Recovery of A13 antigen in lyophilized ADAMTS13 formulations prepared by standard lyophilization protocols.

| | | [µg/ml] 0 M | [%] | [µg/ml] 1 M | [%] | [µg/ml] 2 M | [%] | [µg/ml] 3 M | [%] | [µg/ml] 4 M | [%] | [µg/ml] 6 M | [%] | [µg/ml] 9 M | [%] |
|---|---|---|---|---|---|---|---|---|---|---|---|---|---|---|---|
| -1A | 4° C. | 144 | 100% | — | — | — | — | 147 | 103% | 148 | 103% | 122 | 85% | 129 | 90% |
| | 30° C. | | | — | — | 131 | 91% | 139 | 97% | 132 | 92% | 136 | 95% | 136 | 95% |
| | 40° C. | | | 151 | 105% | 140 | 97% | 137 | 95% | 125 | 87% | 107 | 75% | — | — |
| -2A | 4° C. | 155 | 100% | — | — | — | — | 145 | 93% | 137 | 88% | 125 | 81% | 137 | 88% |
| | 30° C. | | | — | — | 142 | 91% | 137 | 88% | 133 | 86% | 154 | 99% | 133 | 86% |
| | 40° C. | | | 157 | 101% | 141 | 91% | 137 | 88% | 123 | 79% | 97 | 63% | — | — |
| -3A | 4° C. | 143 | 100% | — | — | — | — | 149 | 104% | 146 | 102% | 121 | 85% | 136 | 95% |
| | 30° C. | | | — | — | 141 | 99% | 132 | 92% | 134 | 94% | 132 | 93% | 136 | 95% |
| | 40° C. | | | 164 | 115% | 134 | 94% | 130 | 91% | 139 | 97% | 109 | 76% | — | — |
| -4A | 4° C. | 155 | 100% | — | — | — | — | 152 | 98% | 142 | 91% | 130 | 84% | 126 | 81% |
| | 30° C. | | | — | — | 142 | 92% | 133 | 85% | 125 | 80% | 129 | 83% | 143 | 92% |
| | 40° C. | | | 157 | 101% | 136 | 88% | 131 | 84% | 127 | 82% | 113 | 73% | — | — |
| -5A | 4° C. | 137 | 100% | — | — | — | — | 140 | 102% | 154 | 113% | 118 | 86% | 125 | 91% |
| | 30° C. | | | — | — | 143 | 105% | 121 | 88% | 126 | 92% | 141 | 103% | 132 | 97% |
| | 40° C. | | | 148 | 108% | 139 | 102% | 122 | 89% | 157 | 115% | 112 | 82% | — | — |
| -6A | 4° C. | 138 | 100% | — | — | — | — | 150 | 109% | 134 | 97% | 124 | 90% | 122 | 88% |
| | 30° C. | | | — | — | 145 | 105% | 137 | 99% | 125 | 90% | 143 | 103% | 139 | 101% |
| | 40° C. | | | 147 | 107% | 142 | 103% | 127 | 92% | 119 | 86% | 124 | 90% | — | — |
| -7A | 4° C. | 145 | 100% | — | — | — | — | 148 | 102% | 153 | 105% | 137 | 95% | 126 | 87% |
| | 30° C. | | | — | — | 137 | 95% | 130 | 90% | 125 | 86% | 148 | 102% | 140 | 97% |
| | 40° C. | | | 150 | 104% | 142 | 98% | 128 | 89% | 137 | 95% | 119 | 82% | — | — |
| -8A | 4° C. | 146 | 100% | — | — | — | — | 135 | 92% | 146 | 100% | 138 | 94% | 136 | 93% |
| | 30° C. | | | — | — | 131 | 89% | 137 | 94% | 122 | 84% | 170 | 117% | 139 | 95% |
| | 40° C. | | | 152 | 104% | 142 | 97% | 123 | 84% | 129 | 88% | 122 | 83% | — | — |

TABLE 11

Recovery of A13 antigen in lyophilized ADAMTS13 formulations prepared by extended lyophilization protocols.

| | | [µg/ml] 0 M | [%] | [µg/ml] 1 M | [%] | [µg/ml] 2 M | [%] | [µg/ml] 3 M | [%] | [µg/ml] 4 M | [%] | [µg/ml] 6 M | [%] | [µg/ml] 9 M | [%] |
|---|---|---|---|---|---|---|---|---|---|---|---|---|---|---|---|
| -1B | 4° C. | 112 | 100% | — | — | — | — | 133 | 118% | 137 | 122% | 129 | 115% | 158 | 141% |
| | 30° C. | | | — | — | 144 | 129% | 128 | 115% | 128 | 114% | 145 | 130% | | 0% |
| | 40° C. | | | 138 | 123% | 136 | 121% | 131 | 117% | 132 | 118% | 128 | 115% | — | — |
| -2B | 4° C. | 120 | 100% | — | — | — | — | 132 | 111% | 136 | 114% | 131 | 109% | 164 | 137% |
| | 30° C. | | | — | — | 137 | 115% | 128 | 107% | 124 | 103% | 142 | 119% | | 0% |
| | 40° C. | | | 130 | 109% | 143 | 120% | 147 | 123% | 137 | 115% | 134 | 112% | — | — |
| -3B | 4° C. | 134 | 100% | — | — | — | — | 132 | 99% | 138 | 103% | 133 | 99% | 170 | 126% |
| | 30° C. | | | — | — | 140 | 105% | 120 | 90% | 123 | 92% | 142 | 105% | | 0% |
| | 40° C. | | | 128 | 95% | 137 | 102% | 132 | 98% | 138 | 103% | 128 | 95% | — | — |
| -4B | 4° C. | 138 | 100% | — | — | — | — | 143 | 103% | 141 | 102% | 134 | 97% | 164 | 118% |
| | 30° C. | | | — | — | 153 | 111% | 142 | 103% | 126 | 91% | 156 | 112% | | 0% |
| | 40° C. | | | 123 | 89% | 135 | 98% | 137 | 99% | 142 | 103% | 138 | 99% | — | — |
| -5B | 4° C. | 109 | 100% | — | — | — | — | 139 | 128% | 135 | 124% | 132 | 121% | 171 | 157% |
| | 30° C. | | | — | — | 137 | 125% | 121 | 111% | 126 | 116% | 140 | 128% | | 0% |
| | 40° C. | | | 122 | 112% | 132 | 121% | 135 | 123% | 129 | 118% | 125 | 114% | — | — |
| -6B | 4° C. | 112 | 100% | — | — | — | — | 146 | 130% | 140 | 126% | 127 | 113% | 174 | 156% |
| | 30° C. | | | — | — | 140 | 126% | 124 | 111% | 126 | 113% | 142 | 127% | | 0% |
| | 40° C. | | | 129 | 115% | 144 | 129% | 135 | 120% | 142 | 127% | 131 | 117% | — | — |
| -7B | 4° C. | 123 | 100% | — | — | — | — | 144 | 117% | 146 | 118% | 131 | 106% | 171 | 138% |
| | 30° C. | | | — | — | 149 | 121% | 127 | 103% | 129 | 105% | 136 | 110% | | 0% |
| | 40° C. | | | 128 | 103% | 135 | 110% | 143 | 116% | 136 | 110% | 130 | 106% | — | — |

TABLE 11-continued

Recovery of A13 antigen in lyophilized ADAMTS13 formulations prepared by extended lyophilization protocols.

|  |  | [µg/ml] [%] 0 M | | [µg/ml] [%] 1 M | | [µg/ml] [%] 2 M | | [µg/ml] [%] 3 M | | [µg/ml] [%] 4 M | | [µg/ml] [%] 6 M | | [µg/ml] [%] 9 M | |
|---|---|---|---|---|---|---|---|---|---|---|---|---|---|---|---|
| -8B | 4° C. | 115 | 100% | — | — | — | — | 120 | 104% | 130 | 113% | 131 | 114% | 172 | 149% |
|  | 30° C. |  |  | — | — | 132 | 114% | 126 | 109% | 127 | 110% | 137 | 119% |  | 0% |
|  | 40° C. | 124 | 107% | 141 | 123% | 136 | 118% | 134 | 116% | 128 | 111% | — | — |  |  |

Tables 17 and 18 summarizes the FTIR results of the different lyo programs for rADAMTS022-1 formulations. Neither time nor temperature had a major influence on secondary structures. Also the lyo program did not change structural elements, apart from the apparent decrease of alpha helix at 40° C. for the standard program A which was not seen for the longer lyo program B.

TABLE 17

Secondary structure of lyophilized rADAMTS13 formulation 22-1A evaluated by FTIR.

|  | Prediction α-helix [%] | | | Prediction β-sheet [%] | | |
|---|---|---|---|---|---|---|
| rADAMTS022-1A | 4° C. | 30° C. | 40° C. | 4° C. | 30° C. | 40° C. |
| start |  | 6.7 |  |  | 37.7 |  |
| 1 month |  | 11.7 |  |  |  | 36.6 |
| 2 months |  | 11.7 | 11.3 |  | 37.9 | 36.4 |
| 3 months | 10.9 | 10.7 | 8.9 | 36.8 | 38.4 | 35.7 |
| 4 months | 14.6 | 12.2 | 7.4 | 37.9 | 39.1 | 36.1 |

TABLE 18

Secondary structure of lyophilized rADAMTS13 formulation 22-1B evaluated by FTIR.

|  | Prediction α-helix [%] | | | Prediction β-sheet [%] | | |
|---|---|---|---|---|---|---|
| rADAMTS022-1B | 4° C. | 30° C. | 40° C. | 4° C. | 30° C. | 40° C. |
| start |  | 10.8 |  |  | 36.6 |  |
| 1 month |  | 11.7 |  |  |  | 38.6 |
| 2 months |  | 9.3 | 8.9 |  | 37.8 | 38.4 |
| 3 months | 11.2 | 13.7 | 12.6 | 38.9 | 38.4 | 34.3 |
| 4 months | 6.6 | 12.8 | 10.5 | 35.9 | 39.5 | 37.1 |

The oligomeric state of ADAMTS13 in the 1A and 1B lyophilized formulations was analyzed by dynamic light scattering over the course of 6 months of storage at 4° C., 30° C., and 40° C. As seen in FIGS. 37 and 38, higher aggregate levels were observed in the samples prepared with the extended lyophilization program. However, aggregation levels did not substantially increase over the storage time.

Similarly, size exclusion HPLC did not show no major changes between the different lyo programs for rADAMTS022 formulations after 6 months (data not shown). The analysis show that no aggregates were induced after storage at 4° C., 30° C., and 40° C. over the course of 3 months.

N. Example 14: Expression and Purification of Recombinant Human ADAMTS13

Recombinant ADAMTS-13 is generated by a recombinant Chinese Hamster Ovary (CHO) cell clone in a fermentation process in suspension culture. The growth medium, developed by Baxter and is both free of human or animal derived substances and recombinant proteins. Examples of these types of growth mediums useful for the expression of ADAMTS13 can be found, for example, in U.S. patent application Ser. No. 12/847,999. The manufacturing process utilizes a continuous (chemostat) cell culture method. The purification process starts with an initial cell removal step by filtration. The cell free product of up to 4 subsequent days is combined to produce one downstream batch. The pooled, filtered harvests are concentrated by an ultra/diafiltration and then subjected to a solvent detergent virus inactivation step. Further purification includes a chromatographic capture step (Anion Exchange), a nanofiltration step (second virus reduction step), a negative chromatography step (hydroxyapatite) followed by a mixed mode chromatography (Capto MMC) and a final chromatographic concentration and pre-formulation step (Cation Exchange). The pre-formulated bulk drug substance (BDS) is frozen at −60° C. in a temperature-controlled freezer.

O. Example 15: FRETS-VWF73 Assay for ADAMTS13 Activity

The proteolytic activity of ADAMTS 13 was measured against a fluorescence-quenching substrate (FRETS-VWF73, Peptides Institute, Inc; Osaka, Japan) according to the assay description of the manufacturer. Briefly, rADAMTS13 samples were diluted (in 100 µL total volume) in buffer containing 5 mM Bis-Tris, 25 mM $CaCl_2$, and 0.005% Tween20 and transferred into a black microtiter plate. Samples were measured against a reference curve of diluted human plasma samples (from 80 to 5 mU/mL plasma). The reaction was started by adding the substrate (100 µL, FRETS-VWF73; 2 µM final concentration) and fluorescence was measured every two minutes for 45 minutes in a fluorescence spectrophotometer with lex=360 nm and lem=460 at 30° C. (FLx800, Bio Tek). The activity results were read off a reference curve of human plasma. Data are expressed as Unit/mL. Normal human plasma was regarded as 1 Unit/mL.

P. Example 16: ADAMTS13 Antigen ELISA

ADAMTS13 containing samples are analyzed in an ELISA assay using polyclonal rabbit IgG directed against human ADAMTS13 both as capture and in its labeled form as detection antibody. ADAMTS13 antigen present in the sample is captured by the ADAMTS13-specific antibody coated on a 96-well microtiter plate. Samples were diluted in buffer (250 mM Tris, 350 mM NaCl, 0.5% BSA, 0.1% Tween 20) and transferred to the coated microtiter wells. Bound ADAMTS13 antigen is detected with HRP-conjugated rabbit anti-ADAMTS13 IgG using TMB as substrate (Thermo Art: #34021). Absorbance was measured in a spectrophotometer (TECAN SpectraFluorPlus, Tecan Sales Austria, Gröding, Austria) at 1=450 nm. ADAMTS13 antigen concentrations (expressed in μg/mL) were calculated from a reference standard using dilutions ranging from 250 to 7.81 ng/mL of recombinant ADAMTS13 that was purified from stably transfected HEK293 cell culture harvests.

Q. Example 17: Size Exclusion High Performance Liquid Chromatography (SE-HPLC) Analysis of ADAMTS13

SE-HPLC was performed using an ÄKTA Purifier "900-series" (GE Healthcare). The system was equipped with a Superose 12 GL column (GE Healthcare, TC10/30) which was run at a constant flow rate of 0.3 mL per minute at room temperature. As running buffer 20 mM Tris, 100 mM sodium acetate, 500 mM sodium chloride, pH 7.4 was used. The sample was centrifuged (Centrifuge 5415C, Eppendorf, Vienna, Austria) for 5 min at 10,000 rpm and 100 μL were applied automatically by an autosampler. The absorbance of the column effluent was measured continuously at 280 nm.

R. Example 18: Dynamic Light Scattering (DLS) Analysis of ADAMTS13

Dynamic light scattering (DLS) was performed using a Malvern Nano Zetasizer ZS (Malvern Instruments Ltd Enigma Business Park, Grovewood Road, Malvern, Worcestershire, UK. WR14 1XZ) and a Haake Rheostress 1 (Thermo Fisher Scientific, Karlsruhe, Germany) equipped with a cone with 60 mm diameter/0.5° angle for buffer viscosity measurements.

All samples were centrifuged (Centrifuge 5415C, Eppendorf, Vienna, Austria) for 5 min at 10.000 rpm to determine the hydrodynamic diameter of a protein. 60 μL of sample were filled into a ZEN0040 disposable micro cuvette and viscosity of buffer was determined by Rheostress 1. This parameter is used for analyzing effective size of proteins by DLS. Operation temperature was 25° C. with an equilibration time of 2 minutes. The proteins angle was set to 173° backscatter to measure the size of and 3 runs per sample were performed to average the results.

Samples were measured by increasing temperature mode to monitor the influence of temperature on a protein. Measurement procedure was similar to a normal size measurement, except for different temperatures with an increasing value of 1° C./min from 15° C. to 80° C. and an equilibration time of 2 min. A DTS2145 low volume glass cuvette was used for these temperature ramps.

S. Example 19: Fourier-Transformed Infrared Spectroscopy (FTIR) Analysis of ADAMTS13

Fourier-transformed infrared spectroscopy was performed using the FTIR spectroscope TENSOR 27 (Bruker Optik GmbH, 76275 Ettlingen, Germany) equipped with a Bio-ATR II cell working in attenuated total reflection mode. This instrument configuration can be used to analyze the conformation of protein formulations.

During an operating temperature of 20° C., 20 μL of water were filled into the cell and were measured for background scan. Afterwards 20 μL buffer were filled into the cell and measured against background scan, to subtract water from buffer. This procedure was repeated with buffer as background scan for measuring the sample (measurement range of frequency: 4000-650 cm$^{-1}$). An interferogram was generated and translated into a transmission spectrum. Different spectra were corrected for same offset and were normalized to the same protein concentration. Additionally secondary structure (% α-helix, % β-sheet) of the protein was calculated by the evaluation software (OPUS 6.0/Bruker) which contained a database of ~40 proteins of known secondary structure.

T. Example 20: Photoirradiation Analysis of ADAMTS13 Stability

Photostability testing was performed using the Atlas Suntest CPS+ Photostability Chamber (Chicago, Ill., USA), according to SOP VN-09-45058 TB. The CPS+ monitors and controls irradiance, black standard temperature and chamber air temperature.

Photostability was tested in the same formulation as was used for shear and freeze-thaw experiments (Table 12). The samples and controls were tested by DLS and SE-HPLC. The results are shown in FIG. 31 and FIG. 32. Both formulations (liquid and Lyo) showed the same results by SE-HPLC. The monomer ADAMTS13 peak decreased and the dimer peak increased with irradiation time. Hydrodynamic diameter of liquid and lyophilized formulation also slightly increased with time (FIG. 32). The lyophilized formulation irradiated for 10 h (as recommended by ICH Q1B) did not show any difference to the light-protected control. FRETS activity monitored during photo-irradiation rapidly decreased in liquid but less in lyophilized formulations as shown in FIG. 33. Even after four-fold photoirradiation dose, as recommended by ICH guideline Q1B which corresponds to 4.8M lux hours, more than 50% of FRETS activity remained.

The "control" vials were wrapped in aluminium foil to eliminate exposure to light and placed in the photostability chamber along with the test samples. All samples were placed horizontally. An irradiation time of 10 h corresponded to 1.2 to 1.8 million lux h and 765 W/m$^2$ UV light. Samples were removed from the photostability chamber after 10 h and the spectrum (190-800 nm) and pH value were measured.

U. Example 21: Mechanical Stress Analysis of ADAMTS13 Stability

Shear stress was applied with a Haake Rheostress1 (Thermo Electron Karlsruhe GmbH, Karlsruhe, Germany) using a cone with 60 mm diameter and a 0.5° angle. Temperature was set to 25.0° C.

Briefly, recombinant human ADAMTS13, prepared as described above, was formulated as in Table 12. 500 μL of ADAMTS13 sample per run were applied and stressed at 50, 100, 150, 200, 250, 300, 350, 500 and 600 rpm for 15 min. Then the sample was transferred to an Eppendorf vial. DLS measurements were applied to monitor potential shear stress induced partial unfolding or aggregation. As shown in FIG. 28, aggregates were formed at a shear stress of 200 rpm.

TABLE 12

Formulation used for mechanical stress analysis of ADAMTS13 stability.

| Buffer substances | BAX930 FL |
|---|---|
| NaCl [mM] | 150 |
| Histidine [mM] | 20 |
| Saccharose [%] | 2 |
| Polysorbate 80 [%] | 0.05 |
| pH | 7.0 |

V. Example 22: Effects of Various Buffering Agents on ADAMT13 Formulations

To determine the effect various buffers had on the stability and conformation of ADAMTS13 formulations, recombinant human ADAMTS13, expressed and purified as described above, was dialyzed against different buffers (Table 13) and analyzed by Dynamic light scattering (DLS) to identify basic buffer preferences of ADAMTS13. As can be seen in FIG. 27, the smallest hydrodynamic diameters of ADAMTS13 were found when the protein was formulated in either histidine or HEPES buffers.

TABLE 13

Formulations used to determine the effect of various buffering agents of the formulation of ADAMTS13.

| Buffer substances | -1 | -2 | -3 | -4 | -5 |
|---|---|---|---|---|---|
| NaCl [mM] | 150 | 150 | 150 | 150 | 150 |
| Histidine [mM] | 20 | — | — | — | — |
| Hepes [mM] | — | 20 | — | — | — |
| Sodium phosphate [mM] | — | — | 20 | — | — |
| Citrate [mM] | — | — | — | 20 | — |
| EDTA [mM] | — | — | — | — | 20 |
| pH | 7.5 | 7.5 | 7.5 | 7.5 | 7.5 |

*All formulations contained 2% sucrose and 0.05% polysorbate 80.

W. Example 23: Freeze-Thaw Analysis of ADAMTS13 Stability

The same formulation (Table 12) as used for shear stress experiments was again used to investigate the behavior of the protein during freeze-thaw stress. Two freeze-thaw conditions—20° C./RT and −80° C./+37° C. were chosen. FIG. 29 summarizes the results of the FRETS activity measurements. All samples are stable within the range of the assay's variation (25% relative standard deviation). No FRETS activity loss was seen even after a 5-fold freeze-thaw cycle.

The stability of BAX930 in this liquid formulation is confirmed by the results of the DLS and SE-HPLC measurements. No increase in the intensity of the aggregation peaks (between 100 and 1000 nm) by DLS was observed independent of freeze-thaw conditions (FIG. 30). Similarly, SE-HPLC did not show an increase of the aggregation level after repeated freeze thaw cycles at −80° C./+37° C. but some increase at −20° C./RT (data not shown).

X. Example 24: Effect of Calcium and Zinc on the FRETS Activity of ADAMTS13

Recombinant human ADAMTS13, prepared as described above, was treated with 10 mM EDTA and then dialyzed against buffer containing 20 mM histidine and 190 mM NaCl (pH 7.5). After dialysis, $CaCl_2$ and $ZnCl_2$ were added back to the formulations at different concentrations. The activity of ADAMTS13 formulations containing different concentrations of calcium and zinc were then tested for FRET activity as described above. As can be seen in FIG. 34, increasing levels of calcium increased the recovery of FRETS activity. Near maximum activity was achieved with the inclusion of 4 mM $CaCl_2$, both in the presence and absence of zinc. At intermediate concentrations of calcium (2 mM and 4 mM), the addition of zinc provided a modest increase in FRETS activity.

Y. Example 25: Influence of Salt and Sugar Concentration on Aggregation in Lyophilized ADAMTS13 Formulations To further investigate the effect that salt and sugar concentrations have on lyophilized formulations of ADAMTS13, the oligomeric state of several lyophilized formulations was determined after reconstitution with deionized water. Briefly, recombinant human ADAMTS13 was produced as described above. Protein samples were then formulated with 20 mM histidine (pH 7.0), 2 mM calcium chloride, and 0.05% polysorbate 80 with the sodium chloride and sucrose levels given in Table 15. The formulations were then lyophilized, as described above, and reconstituted with deionized water. Oligomeric characteristics were then determined by SE-HPLC analysis, the results of which are shown in Table 15 and FIG. 35. As can been seen in formulations containing low sugar concentrations, high salt levels (150 mM) increase ADAMTS13 aggregation and reduce the monomeric content of the formulation.

TABLE 15

Influence of salt and sugar concentration on aggregation in lyophilized ADAMTS13 formulations measured by SE-HPLC peak area.

| Lot | NaCl [mM] | Sucrose [g/l] | Osmolarity [mOsmol] | Aggregate [%] | Dimer/Oligomer [%] | Monomer [%] |
|---|---|---|---|---|---|---|
| rADAMTS016-1 | — | 20 | 80.5 | — | 8.3 | 91.9 |
| rADAMTS016-2 | 30 | 20 | 141.0 | — | 10.8 | 89.2 |
| rADAMTS016-3 | 60 | 20 | 196.5 | — | 9.4 | 90.6 |
| rADAMTS016-4 | 90 | 20 | 258.0 | — | 9.2 | 90.8 |
| rADAMTS016-5 | 120 | 20 | 307.5 | — | 9.9 | 90.1 |
| rADAMTS016-6 | 150 | 20 | 359.5 | — | 9.5 | 90.5 |
| rADAMTS016-7 | 60 | 15 | 175.5 | — | 10.0 | 90.0 |
| rADAMTS016-8 | 150 | 15 | 341.0 | — | 9.6 | 90.4 |
| rADAMTS016-9 | 60 | 10 | 163.5 | — | 9.1 | 90.9 |
| rADAMTS016-10 | 150 | 10 | 328.5 | 1.1 | 9.8 | 89.0 |
| rADAMTS016-11 | 60 | 5 | 147.0 | — | 10.0 | 90.0 |
| rADAMTS016-12 | 150 | 5 | 314.5 | 0.7 | 10.4 | 88.8 |

The same formulation shown in Table 15 were then used to evaluate the quality of lyocake produced after lyophilization of ADAMTS13 formulations. As summarized in Table 16, and shown in FIG. 36, the presence of high concentrations of sodium chloride (150 mM) resulted in no lyocake. Conversely, the best lyocakes were obtained with formulations containing between 0 mM and 60 mM sodium chloride in the presence of 2% sucrose.

TABLE 16

Quality of lyocake produced for various formulations of recombinant human ADAMTS13.

| Lot | Lyocake quantification |
|---|---|
| rADAMTS016-1 | compact lyocake, smooth surface and detached off from glass wall |
| rADAMTS016-2 | compact lyocake, smooth surface and detached off from glass wall |
| rADAMTS016-3 | compact lyocake, smooth surface and detached off from glass wall |
| rADAMTS016-4 | compact, porous lyocake, rough surface, partially detached from glass wall |
| rADAMTS016-5 | porous lyocake, rough surface, partially detached from glass wall |
| rADAMTS016-6 | no lyocake, only airy film |
| rADAMTS016-7 | compact, porous lyocake, rough surface, partially detached from glass wall |
| rADAMTS016-8 | no lyocake, only airy film |
| rADAMTS016-9 | airy, smooth film |
| rADAMTS016-10 | powdery, smooth surface |
| rADAMTS016-11 | no lyocake, only airy film |
| rADAMTS016-12 | powdery, smooth surface |

Z. Example 26: Long Term Temperature Stress Test

To further characterize the stability of lyophilized formulations of ADAMTS13, a second long term stress test was initiated. For this test, recombinant human ADAMTS13 was formulated at three final protein concentrations according to Table 19. A second sugar (mannitol) was included in the formulation as it was found to stabilize the protein during lyophilization and provided a compact lyocake with a smooth surface. All stress test samples were characterized by DLS (FIG. 39), SE-HPLC (Table 20), and FTIR. FRETS activity (Table 21) and A13 antigen ELISA (Table 22) were also measured over time for all of the formulations.

TABLE 19

His-Buffer rADAMTS13 formulation for stress test (rADAMTS025)

| | rADAMTS025-1 | rADAMTS025-2 | rADAMTS025-3 |
|---|---|---|---|
| Concentration [U FRETS/mL] | 600 | 300 | 150 |
| NaCl [mM] | 30 | 30 | 30 |
| Histidine [mM] | 20 | 20 | 20 |
| CaCl$_2$ [mM] | 2 | 2 | 2 |
| Polysorbate 80 [%] | 0.05 | 0.05 | 0.05 |
| Sucrose [%] | 1 | 1 | 1 |
| Mannitol [%] | 3 | 3 | 3 |
| pH | 7.0 | 7.0 | 7.0 |

TABLE 20

Influence of high ADAMTS13 concentration on the aggregate level as determined by SE-HPLC (rADAMTS025).

| Lot | Aggregate [%] | Dimer/Oligomer [%] | Monomer [%] |
|---|---|---|---|
| rADAMTS025-1 start | 0.15 | 4.40 | 95.45 |
| rADAMTS025-1 3 months + 4° C. | 0.29 | 4.60 | 95.10 |
| rADAMTS025-1 2 months 30° C. | 0.36 | 4.44 | 95.20 |
| rADAMTS025-1 3 months 30° C. | 0.31 | 5.22 | 94.47 |
| rADAMTS025-1 1 months 40° C. | 0.19 | 5.30 | 94.51 |
| rADAMTS025-1 2 months 40° C. | 0.23 | 5.34 | 94.43 |
| rADAMTS025-1 3 months 40° C. | 0.43 | 5.67 | 93.90 |

TABLE 21

FRETS-VWF73 activity in lyophilized ADAMTS13 formulations.

| | | [U/ml] Preformulation | [U/ml] Before Filtration | [U/ml] Before LYO | [U/ml] 0 M | [%] 0 M | [U/ml] 1 M | [%] 1 M | [U/ml] 2 M | [%] 2 M | [U/ml] 3 M | [%] 3 M | [U/ml] 4 M | [%] 4 M | [U/ml] 6 M | [%] 6 M |
|---|---|---|---|---|---|---|---|---|---|---|---|---|---|---|---|---|
| -1A | 4° C. | 685.6 | 559 | 528 | 522 | 100% | — | — | — | — | 482.20 | 92% | 462.40 | 89% | 411.80 | 79% |
| | 30° C. | | | | | | — | — | 441 | 84% | 471.20 | 90% | 458.30 | 88% | 386.70 | 74% |
| | 40° C. | | | | | | 475 | 91% | 402 | 77% | 441.80 | 85% | 416.30 | 80% | 367.50 | 70% |
| -2A | 4° C. | | 278 | 258 | 252 | 100% | — | — | — | — | 236.6 | 94% | 229.9 | 91% | 210.7 | 84% |
| | 30° C. | | | | | | — | — | 227 | 90% | 231.6 | 92% | 220.7 | 88% | 198.2 | 79% |
| | 40° C. | | | | | | 243 | 96% | 209 | 83% | 212 | 84% | 205.8 | 82% | 181.2 | 72% |
| -3A | 4° C. | | 129 | 122 | 117 | 100% | — | — | — | — | 115 | 98% | 112.4 | 96% | 107.1 | 92% |
| | 30° C. | | | | | | — | — | 106 | 91% | 114 | 97% | 103.1 | 88% | 98.2 | 84% |
| | 40° C. | | | | | | 111 | 95% | 98 | 84% | 99.1 | 85% | 95.5 | 82% | 84.4 | 72% |

TABLE 22

Recovery of A13 antigen in lyophilized ADAMTS13 formulations.

| | | [μg/ml] Preformulation | 8 μg/ml] Before Filtration | [μg/ml] Before LYO | [μg/ml] 0 M | [%] 0 M | [μg/ml] 1 M | [%] 1 M | [μg/ml] 2 M | [%] 2 M | [μg/ml] 3 M | [%] 3 M | [μg/ml] 4 M | [%] 4 M |
|---|---|---|---|---|---|---|---|---|---|---|---|---|---|---|
| -1A | 4° C. | 1044.898 | 602 | 590 | 586 | 100% | — | — | — | — | 671 | 114% | 588 | 100% |
| | 30° C. | | | | | | — | — | 600 | 102% | 689 | 118% | 582 | 99% |
| | 40° C. | | | | | | 574 | 98% | 630 | 107% | 682 | 116% | 562 | 96% |
| -2A | 4° C. | | 324 | 339 | 321 | 100% | — | — | — | — | 355 | 111% | 344 | 107% |
| | 30° C. | | | | | | — | — | 348 | 108% | 323 | 101% | 336 | 105% |
| | 40° C. | | | | | | 321 | 100% | 347 | 108% | 351 | 110% | 353 | 110% |
| -3A | 4° C. | | 150 | 152 | 127 | 100% | — | — | — | — | 166 | 131% | 162 | 128% |
| | 30° C. | | | | | | — | — | 169 | 133% | 177 | 139% | 166 | 131% |
| | 40° C. | | | | | | 147 | 116% | 165 | 130% | 176 | 139% | 168 | 133% |

What is claimed is:

1. A method of treating or preventing thrombotic thrombocytopenic purpura (TTP), the method comprising administering to a subject in need thereof a therapeutically effective dose of an ADAMTS13 formulation, wherein said subject is deficient in ADAMTS13 or suffers from hyperactive VWF and said formulation comprises:
   (a) 0.05 mg/ml to 10.0 mg/ml ADAMTS13;
   (b) 0 mM to 100 mM of a pharmaceutically acceptable salt
   (c) 0.5 mM to 20 mM calcium;
   (d) a sugar and/or sugar alcohol;
   (e) a nonionic surfactant; and
   (f) a buffering agent for maintaining a pH between 6.0 and 8.0.

2. The method of treating or preventing of claim 1, wherein said formulation comprises between about 50 units and about 1000 units of ADAMTS13 activity per mL.

3. The method of treating or preventing of claim 1, wherein said pharmaceutically acceptable salt is sodium chloride (NaCl).

4. The method of treating or preventing of claim 1, wherein said formulation comprises between 1.0 and 10.0 mM calcium.

5. The method of treating or preventing of claim 1, wherein said formulation comprises between 2% and 6% of a sugar and/or sugar alcohol.

6. The method of treating or preventing of claim 1, wherein said sugar and/or sugar alcohol is selected from the group consisting of sucrose, trehalose, mannitol, and a combination thereof.

7. The method of treating or preventing of claim 1, wherein said sugar and/or sugar alcohol is a combination of sucrose and mannitol.

8. The method of treating or preventing of claim 1, wherein said formulation comprises between 0.01% and 0.1% of a non-ionic surfactant.

9. The method of treating or preventing of claim 1, wherein said surfactant is selected from the group consisting of Polysorbate 20, Polysorbate 80, Pluronic F-68, and BRIJ 35.

10. The method of treating or preventing of claim 1, wherein said formulation comprises between 5 mM and 100 mM of a buffering agent.

11. The method of treating or preventing of claim 1, wherein said formulation comprises between 10 mM and 50 mM of a buffering agent.

12. The method of treating or preventing of claim 1, wherein said buffering agent is histidine or HEPES.

13. The method of treating or preventing of claim 1, wherein said formulation has a pH between 6.5 and 7.5.

14. The method of treating or preventing of claim 1, wherein said pH of the formulation is 7.0±0.2.

15. The method of treating or preventing of claim 1, wherein said formulation further comprises between 0.5 µM and 20 µM zinc.

16. The method of treating or preventing of claim 1, wherein said formulation comprises between 0 mM and 90 mM of a pharmaceutically acceptable salt.

17. The method of treating or preventing of claim 1, wherein said formulation comprises between 0 mM and 60 mM of a pharmaceutically acceptable salt.

18. The method of treating or preventing of claim 1, wherein said formulation comprises between 0 mM and 30 mM of a pharmaceutically acceptable salt.

19. The method of treating or preventing of claim 1, wherein said formulation comprises between 30 mM and 60 mM of a pharmaceutically acceptable salt.

20. The method of treating or preventing of claim 1, wherein said formulation comprises between 30 mM and 90 mM of a pharmaceutically acceptable salt.

21. The method of treating or preventing of claim 1, wherein said formulation comprises between 60 mM and 90 mM of a pharmaceutically acceptable salt.

22. The method of treating or preventing of claim 1, wherein said formulation comprises monomeric ADAMTS13 protein and a content of ADAMTS13 aggregates of less than 5% total protein.

23. The method of treating or preventing of claim 1, wherein the specific activity of the ADAMTS13 protein is at least about 600 U of FRETS-VWF73 activity per mg ADAMTS13 protein.

24. The method of treating or preventing of claim 1, wherein said formulation comprises:
   (a) 0.05 mg/ml to 10.0 mg/ml ADAMTS13;
   (b) 0 mM to 60 mM NaCl;
   (c) 2 mM to 4 mM calcium;
   (d) 2% to 4% mannitol;
   (e) 0.5% to 2% sucrose;
   (f) 0.025% to 0.1% Polysorbate 80;
   (g) 10 mM to 50 mM histidine; and
   (h) a pH of 7.0+−0.0.2.

25. The method of treating or preventing of claim 1, wherein said formulation comprises:
   (a) 0.05 mg/ml to 10.0 mg/ml ADAMTS13;
   (b) 0 mM to 100 mM of a pharmaceutically acceptable salt;
   (c) 0.5 mM to 20 mM calcium;
   (d) a sugar and/or sugar alcohol;
   (e) a nonionic surfactant;
   (f) 5 mM to 100 mM of a buffering agent selected from the group consisting of histidine and HEPES; and
   (g) a pH between 6.0 and 8.0.

26. The method of treating or preventing of claim 1, wherein said formulation comprises:
   (a) 0.05 mg/ml to 10.0 mg/ml ADAMTS13;
   (b) 0 mM to 100 mM of a pharmaceutically acceptable salt;
   (c) 0.5 mM to 20 mM calcium;
   (d) 2% to 6% of a sugar and/or sugar alcohol;
   (e) a nonionic surfactant;
   (f) 5 mM to 100 mM of a buffering agent selected from the group consisting of histidine and HEPES; and
   (g) a pH between 6.0 and 8.0.

27. The method of treating or preventing of claim 1, wherein the TTP is acquired TTP.

28. The method of treating or preventing of claim 1, wherein the TTP is hereditary TTP.

29. The method of treating or preventing of claim 1, wherein said subject is deficient in ADAMTS13.

30. The method of treating or preventing of claim 1, wherein said subject suffers from hyperactive VWF.

* * * * *